(12) United States Patent
Certa et al.

(10) Patent No.: US 7,319,933 B2
(45) Date of Patent: Jan. 15, 2008

(54) GENE TRANSCRIPTION ASSAY METHOD

(75) Inventors: Ulrich Certa, Allschwil (CH); Stefan Foser, Grenzach-Wyhlen (DE); Karl Weyer, Bad Bellingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 431 days.

(21) Appl. No.: 10/802,432

(22) Filed: Mar. 17, 2004

(65) Prior Publication Data

US 2004/0185489 A1 Sep. 23, 2004

(30) Foreign Application Priority Data

Mar. 21, 2003 (EP) .................. 03006263

(51) Int. Cl.
- *G06F 19/00* (2006.01)
- *C12Q 1/68* (2006.01)
- *G01N 33/53* (2006.01)

(52) U.S. Cl. .............. 702/19; 435/6; 435/7.1

(58) Field of Classification Search ............ None
See application file for complete search history.

(56) References Cited

U.S. PATENT DOCUMENTS

| | | |
|---|---|---|
| 5,837,832 A | 11/1998 | Chee et al. |
| 2002/0174096 A1 | 11/2002 | O'Reilly et al. |

FOREIGN PATENT DOCUMENTS

| | | |
|---|---|---|
| EP | 0593868 | 4/1998 |
| EP | 0510356 | 1/1999 |
| EP | 0834575 | 11/2001 |
| EP | 0834576 | 1/2002 |
| EP | 0809996 | 4/2003 |
| EP | 1 333 036 | 8/2003 |
| WO | WO96/31622 | 10/1996 |
| WO | WO97/10365 | 3/1997 |
| WO | WO98/30883 | 7/1998 |
| WO | WO02/18633 | 3/2002 |
| WO | WO 02/50306 | 6/2002 |
| WO | WO 02/090927 | 11/2002 |
| WO | WO 2004/045545 | 6/2004 |

OTHER PUBLICATIONS

Kumar-Sinha Molecular Cross-tlak between the TRAIL and Interferon Signalling Pathways. Journal of Biological Chemistry, vol. 277, pp. 575-585 (2002).*
Turri et al. Characterisation of a novel minisatellite that provides multiple splice donor sites in an interferon-induced transcript. Nucleic Acids Research vol. 23, pp. 1854-1861 (1995).*
Certa et al. High density oligonucleotide array analysis of interferon-alpha2a sensitivity and transcriptional response in melanoma cells. British Journal of Cancer vol. 85, pp. 107-114 (2001).*
GenBank Accession No. U22970 [online] [retrieved on Sep. 16, 2006]. Retrieved from the Internet : http://ncbi.nlm.nih.gov/entrez/viewer.fcg?db=nucleotide&val-881920.*
Komor et al. Transcriptional Profiling of Human Hematopoiesis During In Vitro Lineage-Specific Differentiation. Stem Cells vol. 23, pp. 1154-1169 (2005).*
P. Bailon et al., Rational design of a potent, long-lasting form of interferon: A 40 kDa branched polyethylene glycol0conjugated Interferon-2a for the treatment of hepatitis C, Bioconjugate Chem. 12 (2001), 195-202.
Z.Z. Chong, et al., Hematopoietic factor erythropoietin foster neuroprotection through novel signal transduction cascades, J. Cereb.Blood Flow Metab., 22 (2002), 503-514.
CK Glass: Some new twists in the regulation of gene expression by throid hormone and retinoic acid receptors, J. Endorinol, 150 (1996), 349-357.
T. Hanada and A. Yoshimura: Regulation of cytokine signaling and inflammation, Cytokine Growth Factor Rev., 13 (2002), 413-421.
J.M. Harris, et al., Pegylation: A novel process for modifying pharmacokinetics, Clin. Pharmacokinet. 40 (2001), 539-551.
Klaus, et al., J. Mol. Biol. 274 (1997) 661-675.
R. Mandler et al., Modification in syntheses strategy . . . , Bioconjugate Chemistry, 13 (2002), 786-791.
G.S. McKnight: Cyclic AMP second messenger systems, Curr. Opin. Cell Biol., 3 (1991) 213-217.
L. Mulcahy: the erythropoietin receptor, Semin. Oncol. 28 (2001), 19-23.
Y. Nishio, et al., Cilostazol, a cAMP phosphodiesterase inhibitor . . . , Hormone & Metabolic Research, 29 (1997) 491-495.
A. Rowe, Retinoid X Receptors, *Int. J. Biochem. Cell Biol.* 29 (1997), 275-278.
Y. Sato et al., Properties of two VEGF receptors, Flt-1 and KDR, in signal transduction, Ann. N.Y. Acad. Sci., 902 (2000), 201-207.
J.L. Spivak: The mechanism of action of erythropoietin, Int. J. Cell Cloning, 4 (1986) 139-166.
A.H. Talukder et al, Antihuman epidermal growth factor . . . , Clin. Cancer Res. 8 (2002), 3285-3289.
B. Wagner, et al., 7-Benzylamino-6chloro-2piperazino-4-pyrrolidino-pteridine . . . Biochemical Pharmacology, 63 (2002) 659-668.
D.M. Wojchowski and T.C. He: Signal transduction in the erythropoietin receptor system, Stem. Cells, 11 (1993), 381-392.
Andrew R. Pachner, et al., *MxA Gene Expression Analysis an an Interferon-β Bioactivity Measurement in Patients with Multiple Sclerosis and the Identification of Antibody-Mediated Decreased Bioactivity*, Molecular Diagnosis, Mar. 2003, pp. 17-25, vol. 7 (1).
Seth P. Monkarsh, et al., *Positional Isomers of Monopegylated Interferon α-2α: Isolation, Characterization, and Biological Activity*, Analytical Biochemistry, May 1, 1997, p. 434-440, vol. 247(2).
S. Foser, et al., *Improved biological and transcriptional activity of monopegylated interferon-α-2α isomers*, The Pharmacogenomics Journal, 2003, p. 312-319, vol. 3(6).
Jobst, J., et al., Hepatology, vol. 36, No. 4 (Pt.2), p. 289A, (503) (2002).
Der, S.D., et al., Proc. Natl. Acad. Sci. USA., vol. 95 (26), p. 15623-8 (1998).

* cited by examiner

*Primary Examiner*—John S Brusca
(74) *Attorney, Agent, or Firm*—George W. Johnston; Dennis P. Tramaloni

(57) ABSTRACT

The present invention provides a novel method for determining the biological activity of a compound comprising the steps of a) contacting a host with a compound; b) determining the general transcriptional gene response of the host; and c) quantitating the general transcriptional gene response induced by said compound.

4 Claims, 6 Drawing Sheets

GENE TRANSCRIPTION ASSAY METHOD

BACKGROUND OF THE INVENTION

The present invention relates to a novel method for determining the biological activity of compounds which can modulate gene transcription, and based on this method, a method for the determination of the relative biological activity of a compound and a method for the identification of compounds which modulate gene transcription. The methods of this invention are particularly useful for identifying compounds that may be of use in the treatment of diseases which depend on the modulation of gene transcription within affected cells and tissues.

The biological activity of compounds that regulate cellular functions such as cell proliferation or viral protection is commonly determined by measuring increases or decreases of binding activities of these factors and/or compounds either to native or recombinant receptors in vitro, or in cell-based binding assays. A disadvantage of these assays for the evaluation of the biological activity of compounds resides in the fact that the binding affinity does not necessarily correlate with the biological activity of a compound.

A more direct and, therefore, more reliable determination of the biological activity of compounds can be achieved by well known assays such a cell proliferation, cell survival or cell migration assays. Such assays are, however, more cumbersome, especially for larger scale screenings. In many cases, compounds which regulate such cellular activities also modulate gene transcription. Thus, the biological activity of such compounds may be determined by measuring the modulation of gene transcription, which is commonly done by reporter assays, which necessitate the generation of recombinant cells expressing a suitable reporter construct. Alternatively, the biological activity of such compounds may be determined by measuring the expression of suitable target genes, eg. by Northern Blot analysis or quantitative PCR, which is, however, not efficient.

There is accordingly a need to provide a reliable and easy method for the determination of the biological activity of a modulator of transcriptional activity which lacks the disadvantages of binding assays, but is more efficient than the commonly used activity assays.

SUMMARY OF THE INVENTION

In accordance with the present invention, the biological activity of a compound can be determined more reliably by using a novel method based on the determination of the general transcriptional gene response induced by said compound comprising quantitation of signal intensities of genes which are transcriptionally regulated by said compound. The present invention accordingly comprises the steps of a) contacting a host with a compound; b) determining the general transcriptional gene response of the host; and c) quantitating the general transcriptional gene response induced by said compound.

Figure 1:
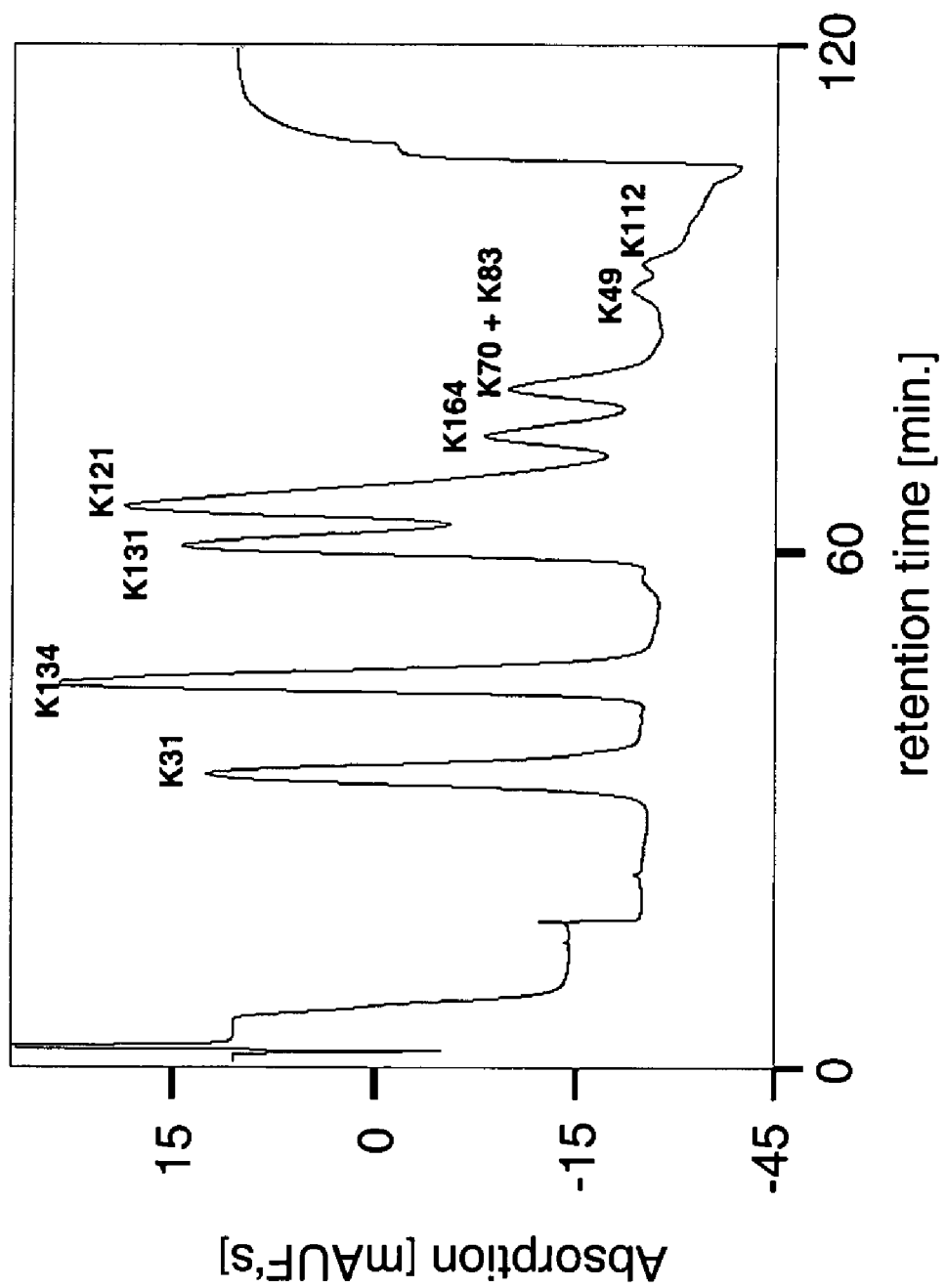
FIG. 1.

Analytical IEC-HPLC of 180 µg of PEG-IFN. An analytical strong-cation exchange column was used to separate the positional isomers (TOSOH-BIOSEP, SP-5PW, 10 µm particle size, 7.5 mm diameter and 7.5 cm length).

FIG. 2:

(A) Specific antiviral activity of the 9 positional isomers and PEG-IFN The figure shows the specific antiviral activity [U/µg] of the positional isomers. The antiviral activity was determined in MDBK cells infected with vesicular stomatitis virus.

(B) Specific anti-proliferative activity of the isomers and PEG-IFN This figure indicates the specific inhibition of proliferation [$OD_{490nm}$/µg] on the ME15 cells with 100 U/ml of the each positional isomer and PEG-IFN.

The results present the averages of three assays performed independently. The specific antiviral activity and specific anti-proliferative activity of PEG-IFN is given for comparison (hatched line).

FIG. 3:

Time dependent inhibition of proliferation in a melanoma cell line (ME15). The ME15 cell line was cultured in presence of different concentrations (500, 125, and 15 U/ml) IFN, PEG-IFN and isomers over 5 days. The cell proliferation was measured every 24 h. The control cell density after 5 days was set as 100% as references. The data are derived from three independent culture replicates.

FIG. 4:

Correlation of the kinetic dissociation constant and specific antiviral activity of the PEG-IFN and isomers with high (K134), intermediate (K131, K164) and low (K121) specific antiviral activity.

FIG. 5:

Correlation of specific antiviral activity, specific anti-proliferative activity and specific transcriptional response of each isomer. The PEG-IFN was set as 100% value reference. The hatched line indicates the biological and transcriptional activity of PEG-IFN. The sum Σ relative mRNA abundance (AD) is illustrated as the sum of all inducible genes for each isomer.

Hierarchical clustering of AD of the different general transcriptional gene response from 100 U/ml IFN, PEG-IFN and the isomers. The incubation time of the IFN and the pegylated variants was 48 h; the cell line used is an IFN-sensitive melanoma cell line (ME15). The conditions for the data analysis are described in the text. The data of the different expression profiles of the genes are reported in Table 3.

FIG. 6:

3D-Structure based Model for PEG-IFN mediated interferon responses. Arrangement of the positional PEG-IFN isomers in four groups according to the specific antiviral and anti-proliferation activity. The high resolution structure of human interferon alpha-2a was determined with NMR spectroscopy (Klaus et al.: The three-dimensional high resolution structure of human interferon alpha-2a determined by heteronuclear NMR spectroscopy in solution. *J. Mol. Biol.* 274 (1997); 661-675). The pegylation sites of interferon alpha-2a are colored red.

DETAILED DESCRIPTION OF THE INVENTION

The present invention provides a novel method for determining the biological activity of a compound which can modulate gene transcription, comprising the steps of a) contacting a host with a compound; b) determining the general transcriptional gene response of the host; and c) quantitating the general transcriptional gene response induced by said compound. Preferably, the biological activity of said compound is given by the sum of the normalized average difference of signal intensities quantitated in step c). In a more preferred embodiment of the present invention the general transcriptional gene response is determined by an DNA array technology. In an even more preferred embodiment, the array technology is an oligonucleotide array technology. Preferably the DNA or oligonucleotide arrays are high density DNA or oligonucleotide arrays. Such arrays, and methods of analyzing DNA or RNA using such arrays have been described previously, eg. in EP0834575, EP0834576, WO96/31622, U.S. Pat. No. 5,837,832 or WO98/30883. WO97/10365 provides methods for monitoring of expression levels of a multiplicity of genes using high density oligonucleotide arrays. In a most preferred embodiment, the oligonucleotide arrays are GeneChip arrays.

The term "general transcriptional gene response" as used herein refers to the biological activity of a compound given by the sum of the normalized average difference of signal intensities of genes regulated by said compound in a responsive host. The determination of the general transcriptional gene response is achieved by hybridizing labeled cDNA from the treated hosts with DNA or more preferably oligonucleotide arrays. The raw data of the arrays is then measured, eg. with a confocal laser scanner (Hewlett Packard, U.S.) as a non-limiting example, and pixel levels are analyzed using commonly known methods. The expression level for each gene is calculated as a normalized average difference of intensity as compared to hybridization to mismatched oligonucleotides, and expressed in arbitrary units (AD). Four criteria are applied to select differentially expressed genes: (1) The intensity value of treated cells was at least two fold higher than the intensity value of untreated cells. (2) The intensity value in the treated cells should be higher or at least 50 arbitrary units (AD). (3) The intensity value of the untreated cells should be lower than 50 AD. (4) The standard deviation has to be significantly lower than the absolute change in average difference and the calculated confidence level of a gene is set to greater than 97% (p value <0.03). The general transcriptional gene response of the host induced by a compound is then quantitated by obtaining the sum of the normalized average difference of signal intensities (sum of arbitrary units, Σ AD).

The non-limiting examples described hereinafter demonstrate that the results obtained with this novel method more reliably correlate with biological activity than do binding assays, with the additional advantage of being efficient. They also show that determining the general transcriptional gene response by the method of the present invention is more reliable than the determination of the transcriptional expression levels of an individual gene or a small selection of genes.

The host used for the method of the present invention may be a whole non-human organism, which includes, but is not limited to a transgenic or a knockout animal; specific types of tissue from any species, which includes, but is not limited to liver, heart, kidney, or primary cell isolates, such as blood cells or primary cells isolated from a tissue, or cell lines. The host or hosts used to determine the biological activity of a compound by the present invention has to be responsive to a compound of interest. The term "responsive" as used herein refers to the ability of a host to exhibit elevated or reduced transcription of genes in response to a compound. As a non-limiting example, a melanoma cell line ME15 (CNCM I-2546 in WO02/18633) can be used to determine the biological activity of PEG-IFN or PEG-IFN isoforms by the method of the present invention.

Figure 4:
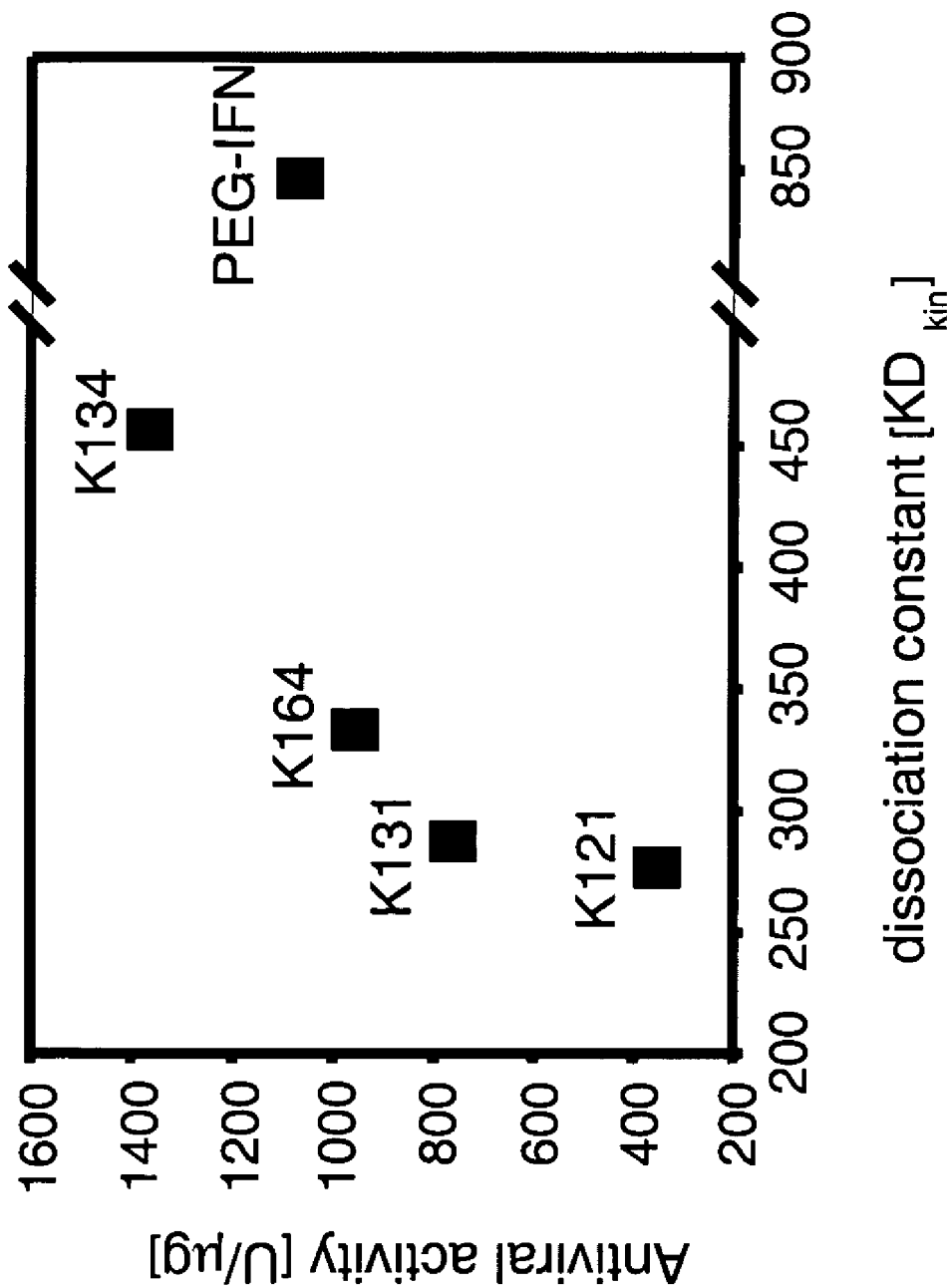
Figure 5:
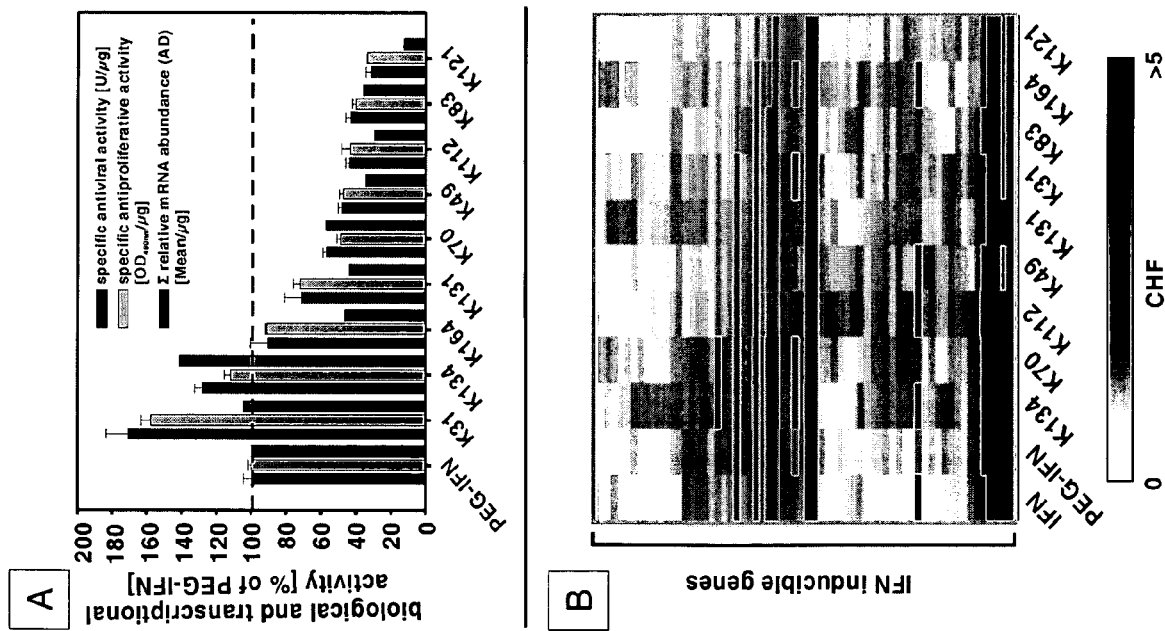
Figure 6:
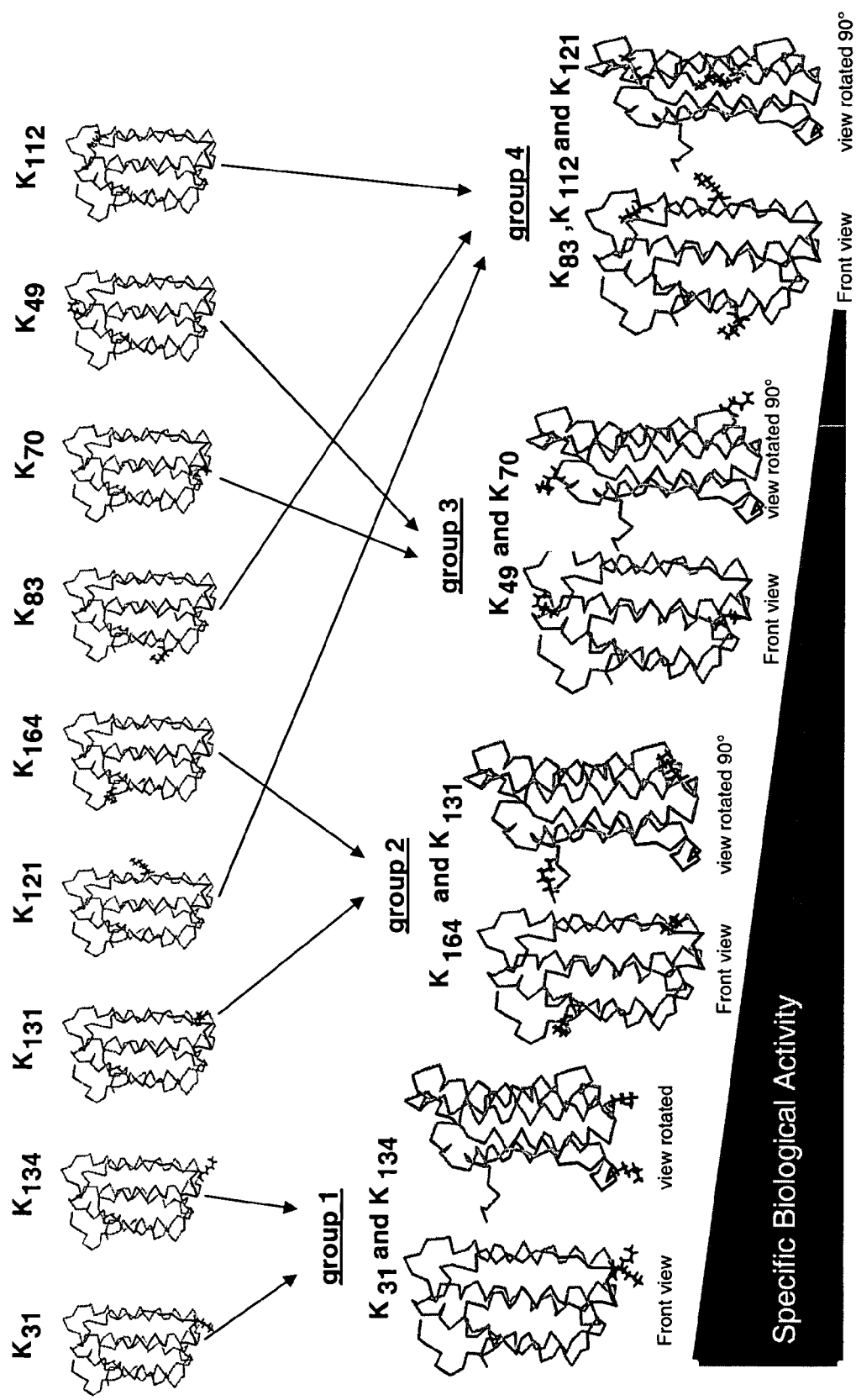

The major advantages of the present invention, as compared to the commonly used activity assays or methods for determining gene transcription such as reporter assays or Northern Blotting are that the method does not require the preparation of any cell lines transfected with reporter constructs, and it allows for an easy and efficient analysis of a multitude of genes that are transcriptionally regulated, thus rendering the activity assays more efficient and reliable. Furthermore, as shown in FIG. 4, binding activities do not always correlate with biological activity, while the determination of the transcriptional activity of compounds based on the determination of the general transcriptional gene response does correlate. Thus, the method of the present invention allows a more accurate determination of the biological activity of compounds than do binding assays.

In one embodiment, the compound of the method hereinbefore described is a modified compound, more preferably a modified protein, even more preferably a pegylated protein, or most preferably, a specific isolated isoform of a pegylated protein. Preferably, the pegylated protein is erythropoietin (EPO) or interferon (IFN).

The term "PEG-IFN" as used herein includes IFN-αs derived from any natural material (e.g., leukocytes, fibroblasts, lymphocytes) or material derived therefrom (e.g. cell lines), or those prepared with recombinant DNA technology. Details of the cloning of IFNα and the direct expression thereof, especially in E. coli, have been the subject of many publications. The preparation of recombinant IFNαs is known, for example from Goeddel et al. (1980) Nature 284, 316-320 and (1981), Nature 290, 20-26, and European Patents Nos. 32134, 43980 and 211148. There are many types of IFNα such as IFNαI, IFNα2; and further their subtypes including but not limited to IFNα2A, IFNα2B, IFNα2C and IFNαII (also designated IFNαII or ω-IFN). The term "IFNα" also includes consensus IFNα available from Amgen or mixtures of natural and/or recombinant IFNαs. The use of IFNα2A is preferred. The manufacture of IFNα2A is described in European Patents Nos. 43980 and 211148.

The IFN-α is conjugated to a polymer such as a polyalkylene glycol (substituted or unsubstituted), for example, polyethylene glycol, to form PEG-IFN-α conjugate. Conjugation may be accomplished by means of various linkers known in the art, in particular by linkers such as those disclosed in European Patent Applications, Publication Nos. 0510356, 0593868 and 0809996. The molecular weight of the polymer, which is preferably polyethylene glycol, may range from 300 to 70.000 daltons, and one or more, preferably one to three, polymers may be conjugated to the IFN-α. A preferred PEG-IFN-α conjugate has the formula:

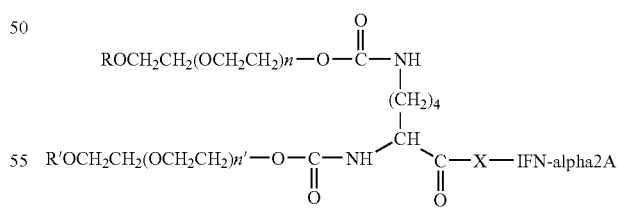

where R and R' are methyl, X is NH, and n and n' are individually or both either 420 or 520.

In another preferred embodiment of the method hereinbefore described, the transcriptionally regulated genes are one or more genes selected from the group consisting of Seq ID No. 1 to 29, which are also listed in Table 1.

The method of the present invention is suitable for the analysis of any compound that modulates gene transcription in any type of host. Modulation of gene transcription includes both upregulation or downregulation of gene transcription.

The method hereinbefore described is the basis for a method for determining the relative biological activity of a modified compound, comprising measuring the biological activity of the modified compound and the respective unmodified compound by the method hereinbefore described, wherein the relative transcriptional activity of the modified protein is determined by calculating the ratio of the biological activity of the modified compound and the biological activity of the unmodified compound. Preferably, the modified compound is a chemically or enzymatically modifed compound. More preferably, the modified compound is a pegylated protein. Thus, this method provides an easy assay to compare the biological activity of modified compounds with their unmodified counterparts. In a preferred embodiment, the present invention allows to select the isoform of a compound with the highest biological activity isolated from a mixture of isoforms, most preferably from pegylated proteins.

The compounds whose biological activity can be determined by the method of this invention include any compound that can modulate gene transcription. These compounds can be proteins, polypeptides, nucleic acids, polymers or small molecules. Many proteins, polypeptides, nucleic acids, polymers or small molecules can modulate gene transcription, either directly, by acting as transcription factors, or indirectly, by inducing signaling cascades that ultimately up- or down-regulate gene transcription or alternatively, by interfering with other compounds that modulate gene transcription. The following list of compounds whose biological activity can be determined by the method of the present invention exemplifies in a non-limiting way the kinds of compounds, including proteins and polypeptides, for which the method of the present invention can be used.

Among these non-limiting examples are hormones, such as retinoid acic, that induce nuclear hormone receptors, which are transcription factors (A. Rowe: Retinoid X receptors, *Int. J. Biochem. Cell Biol.*, 29 (1997), 275-278; and CK. Glass: Some new twists in the regulation of gene expression by thyroid hormone and retinoic acid receptors, *J. Endorinol*, 150 (1996), 349-357). The method of the present invention maybe used to determine the biological activity of such hormones and their nuclear hormone receptors, and it may also be used to identify compounds that interfere with the transcriptional activity of such nuclear hormone receptors. Thus, the present invention may, for example, be useful for identifying and analyzing inhibitors of nuclear hormone receptors such as RXR or LXR.

Further to hormones that activate nuclear hormone receptors, the method of this invention may also be used to determine the biological activity of other hormones which activate signaling cascades that lead up to the modulation of gene transcription. As a non-limiting example, such hormones include erythropoietin (Epo), which is known to modulate gene transcription (Z. Z.Chong et al: Hematopoietic factor erythropoietin foster neuroprotection through novel signal transduction cascades, *J. Cereb. Blood Flow Metab.*, 22 (2002), 503-514; D. M. Wojchowski and T. C. He: Signal transduction in the erythropoietin receptor system, *Stem. Cells*, 11 (1993), 381-392; J. L. Spivak: The mechanism of action of erythropoietin, *Int. J. Cell Cloning*, 4 (1986), 139-166; and L. Mulcahy: The erythropoietin receptor, *Semin. Oncol*. 28 (2001), 19-23).

Cytokines and growth factors are known to induce signaling cascades that lead to a modulation of gene transcription. Thus, as a non-limiting example, the method of the present invention may also be used to identify agonists or antagonists of cytokines and growth factors, and to determine their biological activity. Such cytokines and growth factors include, but are not limited to, Interferons, Tumor Necrosis Factor, Vascular Endothelial Growth Factor (T. Hanada and A. Yoshimura: Regulation of cytokine signaling and inflammation, *Cytokine Growth Factor Rev.*, 13 (2002), 413-421; and Y. Sato et al.: Properties of two VEGF receptors, Flt-1 and KDR, in signal transduction, *Ann. N Y. Acad. Sci.*, 902 (2000), 201-207).

Further to this, the method of the present invention may be used to determine the biological activity of modified or mutated proteins or polypeptides. Modification may be achieved either chemically or enzymatically. A non-limiting example for this application is the determination of the biological activity of different isoforms of pegylated Interferon, which is shown in the Figures attached to this application. Thus, the present invention provides for determining the relative biological activity of a modified compound, comprising measuring the biological activity of the modified compound and the respective unmodified compound by the method hereinbefore described, wherein the relative transcriptional activity of the modified protein is determined by calculating the ratio of the biological activity of the modified compound and the biological activity of the unmodified compound. Preferably, the modified compound is a chemically or enzymatically modifed compound. Most preferably, the modified compound is a pegylated protein.

The method of the present invention may also be used for identifying and characterizing modulators of enzymes which, as a downstream event, can cause a modulation of gene transcription. A non-limiting example for such enzymes are phosphodiesterases (PDE), preferably PDE4, most preferably PDE4D isoenzymes. The PDE4D isoenzymes are preferably selected from the group consisting of PDE4D1, PDE4D2, PDE4D3, PDE4D4, PDE4D5, PDE4D6, PDE4D7 and PDE4D8. PDEs degrade cyclic AMP, a second messenger which can modulate gene transcription (G. S. McKnight: Cyclic AMP second messenger systems, *Curr. Opin.Cell Biol.*, 3 (1991) 213-7), and potent PDE inhibitors were found to modulate gene transcription (B. Wagner et al.: 7-Benzylamino-6chloro-2piperazino-4-pyrrolidino-pteridine, a potent inhibitor of cAMP-specific phosphodiesterase, enhancing nuclear protein binding to the CRE consensus sequence in human tumour cells, *Biochemcial Pharmacology*, 63 (2002) 659-668; Y. Nishio et al.: Cilostazol, a cAMP phosphodiesterase inhibitor, attenuates the production of monocyte chemoattractant protein-1 in response to tumor necrosis factor-alpha in vascular endothelial cells, *Hormone & Metabolic Research*, 29 (1997) 491-495). Thus, the method of the present invention may be used for screening of modulators of such enzymes.

Among the compounds that can be identified and analyzed are also functional antibodies. Functional antibodies are antibodies that either inhibit or stimulate the function(s) of the protein that they bind to. This type of antibodies has been raised against numerous target proteins, and some of these antibodies are also of therapeutic value. Amongst these are, as a non-limiting example, anti-Her2/ErbB2 antibodies, also called Herceptin antibodies. These antibodies are being successfully used in the treatment of breast cancer. They function by inhibiting the activation of human epidermal growth factor receptor Her2/ErbB2, which plays a pivotal role in many types of cancer, including breast cancer. Like many other growth factor receptors, Her2, when bound by its ligand(s), mediates signaling including modulation of gene transcription. It has been shown that Herceptin is capable of modulating gene transcription in cells that express Her2/ErbB2 (A. H. Talukder et al.: Antihuman epidermal growth factor receptor 2 antibody herceptin inhibits autocrine motility factor (AMF) expression and potentiates antitumor effects of AMF inhibitors, *Clin. Cancer Res*.8 (2002), 3285-3289; and R. Mandler et al.: Modification in synthesis strategy improve the yield and efficacy of geldanamycin-herceptin immunoconjugates, *Bioconjugate Chemistry*, 13 (2002), 786-791). Currently, eight different Herceptin antibodies exist, and more may still be produced. Generally, in the case of functional antibodies, the method of the present invention may be used in determining which antibody displays the highest biological activity and would be the most suited for therapeutic use. Thus, the method of the present invention is also suitable for determining the biological activity of antibodies, eg. for the identification of inhibitory or stimulating antibodies. In a preferred embodiment, the antibody is an antibody of therapeutic value. In a more preferred embodiment, the antibody is a Herceptin antibody.

For the identification and analysis of a compound that acts indirectly by inhibiting or stimulating the biological activity of a second compound, such as a hormone, cytokine, growth factor, enzyme etc., the present invention provides a method for identifying compounds that indirectly modulate gene transcription comprising determining the biological activity of a first compound which is a known modulator of gene transcription by the methods hereinbefore described in the presence or absence of a second compound, wherein a compound which indirectly modulates gene transcription is identified if the biological activity of the first compound measured in the presence of said second compound is significantly different from the biological activity of the first compound measured in the absence of said second compound.

The present invention provides a compound identified by the methods hereinbefore described which modulates gene transcription. A use of the methods hereinbefore described for identifying a compound which modulates gene transcription is provided as well. The present invention also provides a kit comprising components for carrying out the methods hereinbefore described. Preferably, said components comprise a DNA array, more preferably an oligonucleotide array.

Furthermore, a pharmaceutical composition comprising a compound identified by the methods hereinbefore described and a pharmaceutically acceptable carrier is provided. Any conventional carrier material can be utilized. The carrier material can be an organic or inorganic one suitable for eteral, percutaneous or parenteral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may contain other pharmaceutically active agents. Additional additives such as flavoring agents, stabilizers, emulsifying agents, buffers and the like may be added in accordance with accepted practices of pharmaceutical compounding.

Additionally, the present invention provides a method for the production of a pharmaceutical composition comprising the steps of identifying a compound by the method of the present invention, modifying the identified compound and formulating the compound obtained with a pharmaceutically acceptable carrier or diluent.

The present invention also provides a use of a compound identified by the methods hereinbefore described or a pharmaceutically acceptable salt thereof for the preparation of a medicament for the treatment of a disease, preferably of a viral disease or of a cancer.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the identified agents wherein the parent agent is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, benzenesulfonic, toluenesulfonic, methanesulfonic, ethane disulfonic, oxalic, isethionic, and the like.

Also claimed are the methods, compounds, kits and uses as hereinbefore described, especially with reference to the foregoing examples.

Having now generally described this invention, the same will become better understood by reference to the specific examples, which are included herein for purpose of illustration only and are not intended to be limiting unless otherwise specified, in connection with the following figures.

EXAMPLES

Antiviral and Anti-proliferative Roles of IFN

Interferon alpha-2a (IFN) plays an important role in mediating antiviral and anti-proliferative responses and in modulating immune responses (G. R. Stark: How cells respond to interferons, *Annu. Rev. Biochem.* 67 (1998), 227-264). These biological activities make IFN important as an inhibitor of disease pathogenesis and useful in the treatment of viral infection and some cancers (S. Zeuzem, et al.: Peginterferon alfa-2a in patients with chronic hepatitis C, *New England Journal of Medicine* 343 (2000), 1666-1172). Since 1986 recombinant human IFN (ROFERON-A) has become an important therapeutic agent to treat patients with viral and oncological diseases (S. Zeuzem et al.: Peginterferon alfa-2a (40 kDa) monotherapy: a novel agent for chronic hepatitis C therapy, *Expert Opinion on Investigational Drugs* 10 (2001), 2201-2213).

The success of IFN treatment in the clinic is partly limited due to its short serum half-life (4-6 h). Peak concentrations of IFN occur 3-8 h following iv. or sc. administration and large fluctuations in serum concentrations can occur after each dose. After 24 h, the amount of exogenous IFN remaining in the body is negligible such that the thrice-weekly regimen used is unlikely to maintain concentrations required for antiviral activity (J. M. Harris et al.: Pegylation:

A novel process for modifying pharmacokinetics, *Clin. Pharmacokinet.* 40 (2001), 539-551; P. Bailon et al.: Rational design of a potent, long-lasting form of interferon: A 40 kDa branched polyethylene glycol-conjugated Interferon-2a for the treatment of hepatitis C *Bioconjugate Chem.* 12 (2001), 195-202).

Administration frequency of IFN is dependent on the disease. For example, the standard therapeutic application of IFN consists of 3 million international units administered subcutaneously three times per week for up to 48 weeks (J. M. Harris et al.: Pegylation: A novel process for modifying pharmacokinetics, *Clin. Pharmacokinet.* 40 (2001), 539-551), while certain oncological indications may require daily administration (P. Bailon et al.: Rational design of a potent, long-lasting form of interferon: A 40 kDa branched polyethylene glycol-conjugated Interferon-2a for the treatment of hepatitis C, *Bioconjugate Chem.* 12 (2001), 195-202). In order to improve the pharmacokinetic and pharmacodynamic properties of IFN, it was conjugated with poly (ethylene glycol) (PEG).

Since several years, studies have been carried out to assess the influence of the various PEG sizes and PEG types on in vitro and in vivo bioactivity. These results showed the important correlation of the PEG characteristics and the biological activity. For example, branched PEG moieties may more effectively cloak and protect IFN from proteolytic degradation than the linear PEG attachments and may also enhance the absorption and distribution properties of protein. Another effect is that increasing the molecular weight of the PEG moiety, decreases the clearance of the therapeutic molecule, thereby producing sustained exposure to the virus (J. M. Harris et al.: Pegylation: A novel process for modifying pharmacokinetics, *Clin. Pharmacokinet.* 40 (2001), 539-551). Based on this knowledge coupled with the latest advancements in pegylation procedures, a long-lasting, branched monopegylated IFN was developed (P. Bailon et al.: Rational design of a potent, long-lasting form of interferon: A 40 kDa branched polyethylene glycol-conjugated Interferon-2a for the treatment of hepatitis C, *Bioconjugate Chem.* 12 (2001), 195-202).

An interferon alpha-2a conjugated via an amide linkage with a branched 40 kDa PEG (PEG-IFN), exhibits sustained adsorption and reduced renal clearance, resulting in strong antiviral pressure throughout a once-weekly dosing schedule (M. C. Perry and B. Jarvis: Peginterferon-α-2a (40 kD): A review of its use in the management of chronic hepatitis C, *Drugs* 15 (2001), 2263-2288; and M. W. Lamb and E. N. Martin: Weight-Based versus fixed dosing of peginterferon (40 kDa) alfa-2a, *The Annals of Pharmacotherapy* 36 (2002), 933-938). The characterization of this PEG-IFN mixture indicated 9 positional isomers which are monopegylated on lysines: $K_{31}$, $K_{49}$, $K_{70}$, $K_{80}$, $K_{112}$, $K_{121}$, $K_{131}$, $K_{134}$ $K_{164}$. All positional isomers induced viral protection of MDBK cells in the Anti-Viral Assay.

Example 1

Preparation of PEG-IFN

The PEG-IFN was manufactured by Hoffmann-La Roche Inc. The pegylated interferon alpha-2a was prepared by the conjugation of lysine ε-amino groups at the surface of the interferon molecule with an activated branched polyethylene glycol derivative of molecular weight 40000 Da (Bailon, P. et al.: Rational design of a potent, long-lasting form of interferon: A 40 kDa branched polyethylene glycol-conjugated Interferon-2a for the treatment of hepatitis C. *Bioconjugate Chem.* 12 (2001); 195-202; EP809996). The isolation and characterization of the isomers of PEG-IFN is described below. All other reagents and chemicals were of the highest purity available.

PEG-IFN consists of a mixture of monopegylated IFN molecules. In each molecule one single lysine is chemically modified by the attachment of a PEG moiety resulting in a mixture of several species. Due to the presence of eleven lysines and a free N-terminal amino group twelve monopegylated species are expected, but only nine lysine-modified species could be found (K31, K49, K70, K83, K112, K121, K131, K134 and K164).

Example 2

Purification and Characterization of Positional PEG-IFN Isomers

We developed a preparative two step chromatography method allowing efficient separation of these species. The purity of the prepared positional isomers could be checked by an analytical ion exchange method, see an example for an elution profile in FIG. 1. Separation is based on local charge differences of the isomers resulting from the different pegylation sites on the protein moiety. The decrease of the baseline absorption towards the end of the chromatogram suggests that there were no other monopegylated species of IFN eluting at higher retention time. By two step separation nine positional isomers were purified, the characterization of the isomers indicate the pegylation sides are all on lysines: K31, K49, K70, K83, K112, K121, K131, K134 and K164.

Example 3

Separation of the Positional Isomers

A two-step isolation and purification scheme was used to prepare the monopegylated isoforms of PEG-interferon alpha 2a.
a) The first step was a separation of the positional isomers on a preparative low pressure liquid chromatography column with a weak-cation exchange matrix (TOSOH-BIOSEP, Toyopearl CM-650S, Resin Batch no. 82A having a ion exchange capacity of 123 mEq/ml, the diameter of the column being 16 mm, the length 120 cm). A linear pH-gradient of increasing sodium acetate concentration (25 mM, pH 4.0 up 75 mM to pH 7.8) was applied at a flow rate of 0.7 mL/min. Detection was at 280 nm. With this chromatographic step species 1, 2, 5, 6 and a mixture of 3, 4, 4a, 7 and 8 could be collected, see Table 1.
b) The fractions were further separated and purified in the second preparation step. A preparative column with the same matrix as the analytical strong-cation exchange column as described above but larger dimensions (30 mm i.d. and 70 mm length), further a higher flow rate and an extended run time was used. As for the analytical method the column was pre-equilibrated with 3.4 mM sodium acetate, 10% ethanol and 1% diethylene glycol, adjusted to pH 4.4 (buffer A). After loading the PEG-IFN samples, the column was washed with buffer A, followed by an ascending linear gradient to 10 mM dibasic potassium phosphate, 10% ethanol and 1% diethylene glycol, adjusted to pH 6.6 (buffer B). The flow rate was 1.0 mL/min and the detection at 218 nm.

The protein concentration of the PEG-IFN alpha 2a isomer was determined by spectrophotometry, based on the 280 nm absorption of the protein moiety of the PEG-IFN alpha 2a.

An analytical elution profile of 180 μg of PEG-IFN alpha 2a is shown in FIG. 1. The result of this method is a separation into 8 peaks, 2 peaks with baseline separation and 6 with partial separation. The decrease of the baseline absorption towards the end of the chromatogram suggests that there were no other monopegylated species of IFN alpha 2a eluting at higher retention time.

In addition, looking carefully at the IEC-chromatogram a further peak close to the detection limit is visible between peaks 2 and 3 indicating the presence of additional positional isomers that should also contribute to the specific activity of the PEG-IFN alpha 2a mixture. Additional species were expected as the interferon alpha-2a molecule exhibits 12 sites for pegylation (11 lysines and the N-terminus). However, given the low abundance of the these species, they were not isolated and characterized.

Isomer samples derived from IEC optimization runs were investigated directly after the isolation (t=0) and after 2 weeks of storage at 5° C. No significant differences were observed for the protein derived from IEC-peaks with regard to the protein content as determined by spectrometric methods; nor were any changes to be detected in the monopegylation site, the content of oligo-PEG-IFN alpha 2a, the amount of aggregates and the bioassay activity. Taking into account the relative abundance of the individual isomers—as determined by the IEC method—as well as the specific activities—as determined in the anti-viral assay—almost the total specific bioactivity of the PEG-IFN alpha 2a mixture used for their isolation is recovered (approximately 93%).

The analytical IE-HPLC was used to check the purity of the individual isomers with respect to contamination with other positional isomers in the IEC fractions. The peaks 2, 3, 4, 4a, 5 and 7 had more than 98%, the peaks 1 and 8 had 93% and peak 6 had 88% purity.

TABLE 1

PEG-peptides identified by comparison of the Lys-C digest spectra of the isomers and the reference standard.
Identified PEG Sites in the separated PEG-IFN Species

| PEG-IFN Peak | PEG site | missing peaks in peptide map M$_r$ (DA) | Sequence |
|---|---|---|---|
| Peak 1 | K$^{31}$ | A, E | 24-49 |
| Peak 2 | K$^{134}$ | I, I' | 134-164 |
| Peak 3 | K$^{131}$ | C | 122-131[a] |
| Peak 4 | K$^{121}$ | B, C | 113-131 |
| Peak 4a | K$^{164}$ | b | 134-164[a,b] |
| Peak 5 | K$^{70}$ | D, F | 50-83 |
| Peak 6 | K$^{83}$ | D, H | 71-112 |
| Peak 7 | K$^{49}$ | E, F | 32-70 |
| Peak 8 | K$^{112}$ | B, H | 84-121 |

[a]132-133 too small to detect.
[a,b]RP-HPLC.
The fractions were characterized by the methods described herein.

Example 4

Analysis of the Fractions by Mass Spectrometry Peptide Mapping

Mass spectra were recorded on a MALDI-TOF MS instrument (PerSeptive Biosystems Voyager-DE STR with delayed extraction). Each IEC fraction (Ion Exchange Chromatography) was desalted by dialysis, reduced with 0.02 M 1,4-dithio-DL-threitol (DTT) and alkylated with 0.2 M 4-vinyl pyridine. Then the proteins were digested with endoproteinase Lys-C (Wako Biochemicals) in 0.25 M Tris (tris(hydroxymethyl)-aminoethane) at pH 8.5 with an approximate enzyme to protein ratio of 1:30. The reaction was carried out over night at 37° C.

A solution of 20 mg/ml α-cyano-4-hydroxycinnamic acid and 12 mg/ml nitrocellulose in acetone/isopropanol 40/60 (v/v) was used as matrix (thick-layer application). First, 0.5 μL of matrix was placed on the target and allowed to dry. Then, 1.0 μL of sample was added. The spectra were obtained in linear positive ionization mode with an accelerating voltage of 20.000 V and a grid voltage of 95%. At least 190 laser shots covering the complete spot were accumulated for each spectrum. Des-Arg$^1$-bradykinin and bovine insulin were used for internal calibration.

Example 5

High-performance Liquid Chromatography (RP-HPLC) Peptide Mapping

The peptides were characterized by reverse-phase high-performance liquid chromatography (RP-HPLC) Peptide Mapping. The IEC fractions were reduced, alkylated and digested with endoproteinase Lys-C as described for the MALDI-TOF MS peptide mapping. The analysis of the digested isomers was carried out on a Waters Alliance HPLC system with a Vydac RP-C18 analytical column (5 μm, 2.1×250 mm) and a precolumn with the same packing material. Elution was performed with an acetonitrile gradient from 1% to 95% for 105 min in water with a flow rate of 0.2 mL/min. Both solvents contained 0.1% (v/v) TFA. 100 μL of each digested sample were injected and monitored at 215 nm.

Example 6

MALDI-TOF Spectra of Undigested Protein

An 18 mg/ml solution of trans-3-indoleacrylic acid in acetonitrile/0.1% trifluoro-acetic acid 70/30 (v/v) was premixed with the same volume of sample solution. Then 1.0 μL of the mixture was applied to the target surface. Typically 150-200 laser shots were averaged in linear positive ionization mode. The accelerating voltage was set to 25.000 V and the grid voltage to 90%. Bovine albumin M$^+$ and M$^{2+}$ were used for external calibration.

Example 7

SE-HPLC (Size Exclusion HPLC)

SE-HPLC was performed with a Waters Alliance 2690 HPLC system equipped with a TosoHaas TSK gel G 4000 SWXL column (7.8×300 mm). Proteins were eluted using a mobile phase containing 0.02 M NaH$_2$PO$_4$, 0.15 M NaCl, 1% (v/v) diethylene glycol and 10% (v/v) ethanol (pH 6.8) at a flow rate of 0.4 mL/min and detected at 210 nm. The injection amounts were 20 μg of each isomers.

Size Exclusion HPLC and SDS-PAGE were used to determine the amount of oligo-PEG-IFN alpha 2a forms and aggregates in the different IEC fractions. The reference material contains 2.3% aggregates and 2.2% oligomers.

Peaks 1, 4, 4a, 5, 6 and 8 contain <0.7% of the oligopegylated IFN alpha 2a forms, whereas in peaks 2, 3, and 7 the percentage of the oligopegylated IFN alpha 2a forms are under the detection limit (<0.2%). In the case of the aggregates a different trend could be seen. In all peaks the amount of aggregates is below 0.9%.

Example 8

SDS-PAGE

SDS-PAGE was carried out both under non-reducing and under reducing conditions using Tris-Glycine gels of 16% (1.5 mm, 10 well). Novex Mark 12 molecular weight markers with a mass range from 2.5 to 200 kDa were used for calibration, bovine serum albumin (BSA) was used as sensitivity standard (2 ng). Approximately 1 µg of all the samples and 0.5 µg of standard were applied to the gel. The running conditions were 125 V and 6 W for 120 min. The proteins were fixed and stained using the silver staining kit SilverXpress from Novex.

The gels that were recorded under non-reducing conditions for the IEC fractions 1-8 show a pattern that is comparable to that of the PEG-IFN alpha 2a reference standard.

Under reducing conditions, the gels show an increase in intensity of the minor bands at about 90 kDa as compared to the standard. Between 6 and 10 kDa protein fragments appear for peaks 6, 7 and 8. Both bands together correspond to approximately 1% of clipped material. In the lanes of isomer 1, 5, 6, 7, 8 additional bands with more than 100 kDa can be seen which are also present in the standard. These can be assigned to oligomers. Thus SDS-PAGE confirms the results of the SE-HPLC analysis.

Overall, RP-HPLC and SDS-PAGE experiments indicate that the purity of the IEC fractions can be considered comparable to the PEG-IFN alpha 2a reference standard.

The structure of the PEG-IFN alpha 2a species derived from the 9 IEC-fractions were identified based on the results of the methods described above using the strategy mentioned above.

Example 9

In Vitro Antiviral Protection Activity

The antiviral activities of the isolated isomers were determined by the reduction of the cytopathic effect of vesicular stomatitis virus (VSV) on Madin-Darby bovine kidney (MDBK) cells. The cell lines were cultured in MEM-medium containing 10% fetal bovine serum. The isomers and PEG-IFN were diluted to a final concentration of 10 ng/ml (assay starting concentration) for the detection of the effective concentration. This effective concentration ($EC_{50}$) was determined as the concentration needed for 50% protection of the cells against the VSV. In all measurements, the cell culture was challenged with VSV 4 hours after addition of the PEG-IFN isomers. After 18 hours growth at 37° C. the cells were stained with crystal violet® to determine the number of intact cells.

To determine the antiviral activity of the 9 positional isomers the $EC_{50}$-values were measured. PEG-IFN was tested in this assay as a reference.

FIG. 2A shows the specific activities (U/µg, grey columns) of the isomers. In this assay all positional isomers had activity, however at a different level. The isomers K31 with 170% and K134 with 125% display higher values than PEG-IFN. K164 was equal to the mixture whereas the activities of K49, K70, K83, K112, K121 and K131 were lower.

Example 10

Anti-proliferative Activity Assay

For this assay, a primary cell culture of human melanoma metastases cells (ME15) was used. This cell line was deposited on Aug. 17, 2000 under the terms of the Budapest Treaty at the Collection Nationale de Cultures de Microorganismes, Institut Pasteur, Paris under the registration number CNCM I-2546. The cell line was cultured in RPMI medium supplemented with 10% FCS, 2 mM glutamine, 1 mM sodium pyruvate, 10 mM non-essential amino acids and HEPES buffer (all from Gibco Life Sciences, UK). When confluent, the cells were passaged by trypsinization. Approximately 5000-6000 cells per well in a flat bottom 96 well plate were used as a start point for the cell proliferation assay in the presence or in the absence of the individual concentrations of IFN, PEG-IFN and the isomers over a period of a 5 day period. The number of living cells was then determined using a cell staining kit (Promega, Madison, USA) based on the colorimetric detection of the cleavage of the tetrazolium salt MTS into formazan. The MTS reaction solution was added according to the manufacturer's recommendation for a period of 4 hours at 37° C., after this period the absorption at 490 nm was recorded in a spectrophotometer.

The specific anti-proliferative activity of the isomers was determined by using an IFN- sensitive melanoma cell line (ME15) and a commercial assay. Positional isomers and PEG-IFN as references were used at a concentration of 100 U/ml (FIG. 2B). The biological unit (U) for the isomers which was used for the experiments was defined and determined in the antiviral assay hereinbefore described, with PEG-IFN as standard reference.

In this assay all isomers were active with the isomer K31 at 159% and K134 at 115% relative to PEG-IFN. K164 displayed the same activity as PEG-IFN; all other isomers were less active than the reference.

The results rank the activity essentially in the same order as in the antiviral assay indicating that same activities are derived from a common trigger or signaling event.

Figure 3:
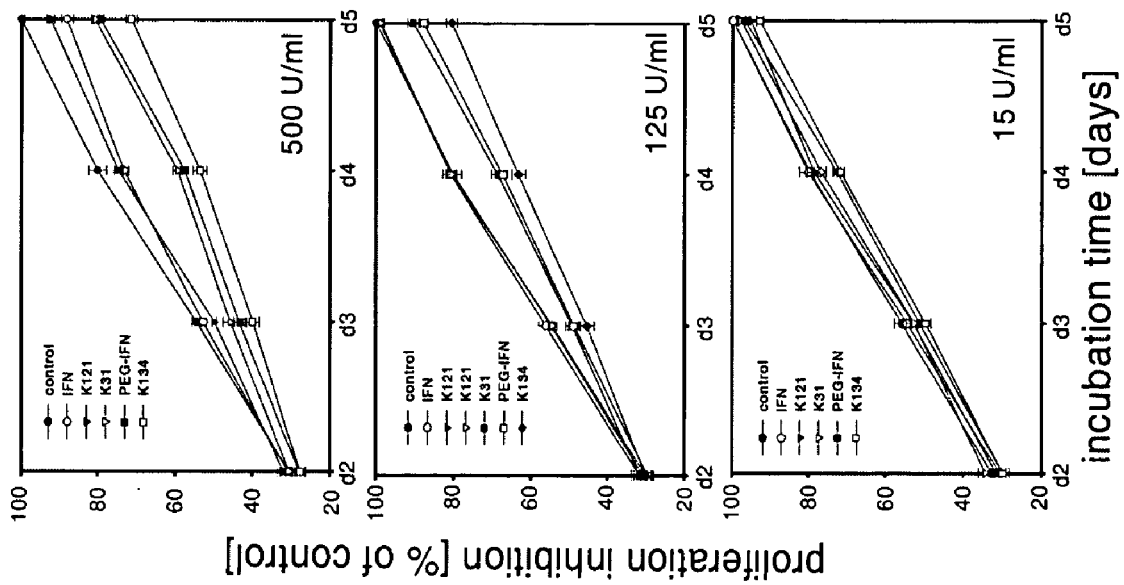

One explanation for the different specific activities of the nine positional isomers in the two previous experiments could be their different protein stability. To find this out we tested some isomers at different concentrations in a time course experiment using the ME15 cell line. We selected isomers K31 and K134 which have the highest activity, and K121, which is the isomer with the lowest activity, together with IFN and PEG-IFN as references (see FIG. 3). Different concentrations of IFN, PEG-IFN and positional isomers (500, 125 and 15 U/ml) were used for the treatment of the ME15 cells over a period of 5 days. Every 24 h the number of cells was measured.

Again we found a striking correlation to the anti-proliferative activity described above with K134 being most active followed by K31 and PEG-IFN. As expected the lowest activity was found for K121 and IFN.

It can be observed that the inhibition of proliferation is decreased by diminishing concentration. Interestingly, PEG-IFN used at a concentration of 500 U/ml exhibits identical anti-proliferative activity as compared to the isomer K134 used at 125 U/ml after 5 days, while IFN and K121 exhibit lower or no anti-proliferative activity after 5 days when used at a concentration of at least 125 U/ml.

In three independent biological assays we established a correlation between the intramolecular attachment site of the PEG moiety and the biological activity. In summary, the isomers K31 and K134 showed consistently higher specific activities than the commercial mixture, while the remaining seven isomers had a similar specific activity compared to the commercial mixture (K164). Activities range between 170% and 20% indicating that the difference in specific activities of the protein between the positional isomers is significant.

Example 11

Expression and Purification of the Recombinant Extracellular Domain of the Interferon Receptor 2 from E.coli The extracellular domain of the Interferon Receptor 2 (IFNR2-EC) was cloned into a pET15b-vector (Invitrogen, US) with an N-terminal His-Tag®. This vector construct was used to express IFNR2-EC in E.coli. The target protein precipitated in the cells in the form of inclusion bodies. The E.coli pellet after the fermentation in full medium was resuspended in lysis buffer containing 50 mM Tris, 10% saccharose, 0.02% sodium azide, 10 mM magnesium chloride and EDTA-free protease inhibitor. After the homogenization in a French Press and centrifugation (13000 rpm) the inclusion bodies were solubilized in 8 M urea. The first chromatography step was a nickel chelate chromatography with a linear gradient from 0-500 mM imidazol over 10 column volumes. The pooled peak of IFNR2 was dialyzed against 8 M urea to remove the imidazol. After this dialysis the sample was diluted to 0.1 $A_{280}$ with 8 M urea containing 150 mM Tris/HCL pH 8.0 and stored at room temperature until the Ellman assays were negative. The oxidized IFNR2-EC was dialyzed against 50 mM Tris pH 8.4 for refolding. 50 mM Tris pH 8.4 was also the starting buffer for the second chromatography. The second chromatography step was with an anion ion-exchange resin (HiTrap Q HP, 5×5 ml, Amersham Biosciences) with a gradient of 0-500 mM NaCl.

All purification steps were analyzed by SDS-PAGE under reduced and non-reduced conditions. The protein purity was monitored by analytical size-exclusion chromatography using Superdex® 75 and 200 HR (PC 3.2/30, Amersham Biosciences). This chromatography method was also used to determine both the binding activity and capacity (data not shown).

Example 12

Characterization of the Interaction of IFN and the PEG-IFN Isomers with the IFNR2-EC Using an Optical Biosensor System The immobilization of the IFNR2-EC was achieved by labeling with biotin. The biotinylated protein was anchored to a streptavidin sensor surface (SA Sensor, BIAcore).

Biotinylation was performed by diluting the protein stock solution (10 mM acetate, pH 7.5) with Hepes (10 mM, pH=8.4) to a final protein concentration of 0.23 mg/ml protein (8.65 µM). A 8.65 mM solution of biotinamidocaproate-n-hydroxysuccinimide ester (Fluka) in DMSO was added to the solution to give a final concentration of the fractions were characterized by the methods described herein. biotinylating reagent of 86.5 µM. The mixture was allowed to react for 1 h before it was dialyzed over night against a Hepes buffer (10 mM, pH 8.4, 150 mM NaCl) to remove low molecular weight reaction products. This solution was used in the immobilization procedure. Immobilization was achieved by contacting the solution of the biotinylated protein with the SA sensor surface. The amount of immobilized protein was controlled via the contact time. For the binding experiments 4000 RU, corresponding to approximately 4 ng/mm² of protein were immobilized.

Binding experiments were performed in Hepes buffer (10 mM Hepes, 150 mM NaCl, 3 mM EDTA, 0.005% polysorbate 20, pH 7.4) as the running buffer. Interferon solution was prepared by diluting stock solutions of the proteins with running buffer. The flow velocity was set to 5 µl/min for all binding experiments. The interferon solutions were contacted for a time interval of 5 min with the immobilized IFNR2-EC.

Calculation of binding data: dissociation constant ($K_D$) values were determined by fitting the time dependent response curves with a mathematical fit based on the simple kinetic model of the formation of a 1/1 complex. $k_{on}$ and $k_{off}$ values were obtained from this fit. $K_D$ represents the ratio $k_{off}/k_{on}$ Investigation of the interaction of proteins by label-free solid phase detection such as surface plasmon resonance (SPR) requires the immobilization of one of the interacting compounds.

We used two different coupling strategies to immobilize IFN or IFNR2-EC to the sensor surface. The IFN was immobilized via free amino groups on a carboxylated dextran sensor surface, the IFNR2-EC was labeled with biotin and anchored to a streptavidin sensor surface. With these two sensors and the corresponding IFN respectively IFNR2-EC binding test were done. Consistent values of rate constants and binding affinities were obtained. The results indicate that the binding affinity is independent of the immobilization technique and the immobilized protein (data not shown). These preliminary tests were necessary to increase the accuracy for the measurements with the isomers and to verify the simple kinetic model of 1/1 complex formation.

Figure 2:
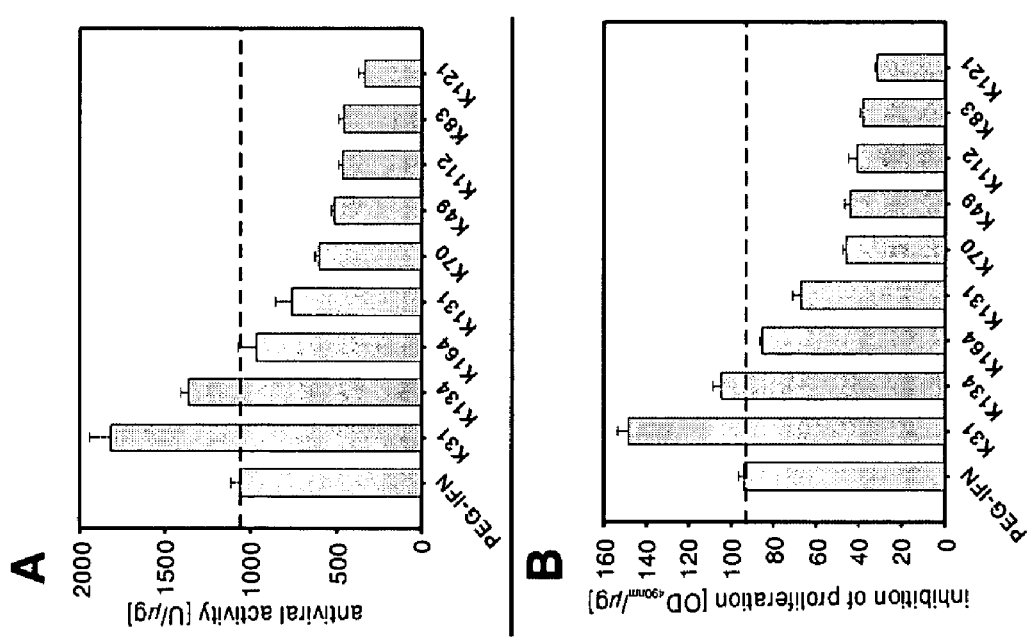

For the determination of the affinity and kinetic constants we selected five isomers (K31, K121, K131, K134 and K164) to cover the whole activity range of the specific biological activity (see FIG. 2 A,B). To increase the significance of the kinetic and equilibrium parameters, we performed binding studies on the immobilized IFNR2-EC with different concentrations of the isomers. The IFN and PEG-IFN were used as a reference. The result of the binding curve fits based on a kinetic model for a formation of a 1/1 complex are given in Table 2.

TABLE 2

Kinetic constants for the interaction of wild-type IFN; PEG-IFN and several positional isomers

| | $k_{on}$ [$10^5$ M-1xs-1] | $k_{off}$ [$10^{-2}$ s-1] | $K_{Dkin}$ [nM] |
|---|---|---|---|
| IFN | 12.5 | 1.14 | 9.12 |
| PEG-IFN | 0.27 | 2.3 | 851 |
| $K_{31}$ | n.d. | n.d. | n.d. (>1 mM) |
| $K_{134}$ | 0.87 | 3.96 | 455 |
| $K_{131}$ | 0.96 | 2.8 | 289 |
| $K_{121}$ | 0.83 | 2.33 | 279 |
| $K_{164}$ | 0.652 | 2.19 | 335 |

The table shows the measured affinity and kinetic data. The calculation for the kinetic constant is based on the kinetic model of a 1/1 complex formation. The IFNR2-EC was labeled with biotin. This biotinylated protein was anchored to a streptavidin sensor surface (SA Sensor, Biacor). Binding experiments were performed in Hepes buffer (10 mM Hepes, 150 mM NaCl, 3 mM EDTA, 0.005% polysorbate 20, pH 7.4) as the running buffer.

The obtained $K_D$-values indicate that the pegylation of IFN causes a decrease in the affinity towards the INFR2-EC. The affinity deficit is dependent on the position of pegylation. The affinity change is generally due to a change in the association constants ($k_{on}$) For instance, isomer K134 changes the affinity roughly by a factor of 15. $k_{on}$ is reduced by a factor of more than 10, whereas $k_{off}$ is increased only by a factor of approximately 4.

For the isomer K31 only an estimation of the $K_D$ was possible because the protein concentrations were too low.

Combining the data from the specific antiviral or specific anti-proliferative activity with the IFNR2-EC affinity study an interesting correlation was observed as seen in FIG. 4. It indicates that the higher the IFNR2-EC affinity (low $K_D$) of a given isomer, the lower the specific biological activity. This correlation is opposed to the common drug screening dogma which is principally used to search ligands which have a low $K_D$ and a high biological activity.

Example 13

Transcriptional Response of the Isomers Compared to IFN

DNA microarrays which permit simultaneous measurement of the expression levels of thousands of genes, provide a comprehensive frame-work to determine how the positional isomers affect cellular metabolism and regulation on a genomic scale.

To estimate the influence of the pegylation site on the transcriptional activity of IFN we measured the IFN-induced gene expression pattern of the melanoma cell line ME15 via the oligonucleotide array technology.

ME15 cells were incubated for 48 h with 100 U/ml of IFN, PEG-IFN or PEG-IFN isoforms. After 48 h the cultured cells were harvested by scraping and the total cellular RNA was extracted with RNA-Bee™. From each sample 10 μg of the total cellular RNA were reverse transcribed (Invitrogen, U.S.), labeled (Ambion, U.S.) and processed by using commercial kits according to the supplier's instructions. The methods of the alkaline heat fragmentation and the following hybridization of the cDNA with the U95Av2 GeneChip arrays were standard procedure provided by the manufacturer of the microchips (Affymetrix, U.S.). A further example for a procedure for performing oligonucleotide array analysis can be found in Fambrough et al., Diverse signaling pathways activated by growth factor receptors induce broadly overlapping, rather than independent, sets of genes, *Cell* 97 (1999), 727-741.

The raw data of the arrays were measured with a confocal laser scanner (Hewlett Packard, U.S.) and pixel levels were analyzed using GeneChip v3.1 software (Affymetrix, U.S.). The expression level for each gene was calculated as normalized average difference of fluorescence intensity as compared to hybridization to mismatched oligonucleotides, expressed in arbitrary units (AD). Each investigation of the samples was measured in triplicate with labeled cRNA from three different cell plates.

The following four criteria were chosen for differential expression of a gene after treatments with IFN, PEG-IFN or the PEG-IFN isoforms compared to the untreated cells were: (1) The intensity value of the treated cells is at least two fold higher than the untreated cells. (2) The intensity value in the treated cells should be higher or at least 50 AD. (3) The intensity value of the untreated cells should be lower than 50 AD. (4) The standard deviation has to be significantly smaller than the absolute change in average difference and the calculated confidence level of a gene is set greater than 97% (p value <0.03).

For these experiments we used the same cell line (ME15) as for the anti-proliferative assay. We treated the cells for 48 h with 100 U/ml of each isomer or with IFN and PEG-IFN. IFN was used as the reference. After this treatment total RNA was isolated from the ME-15 cells. The methods for preparation of cRNA and subsequent steps leading to hybridization and scanning of the U95Av2 GeneChip Array are described above. Visual inspection of total RNA samples before processing by agarose gel electrophoresis did not reveal any signs of degradation or yield in the samples. The number of biological replicates for each isomer, IFN and PEG-IFN (n=3) allows the application of statistical algorithms for data analysis in order to account for experimental variation. The data analysis focused on genes which were lower than 50 AD in the untreated cells but at least 2-fold up-regulated with an AD value of at least 50 in the treated cells.

The standard deviation had to be significantly smaller than the absolute change in average difference and the calculated confidence level of a gene was set to greater than 97% (p value <0.03).

By applying these criteria, an expression profile of 29 up-regulated genes was observed. In this expression pattern 13 known IFN-inducible genes which are involved in the anti-proliferative and antiviral pathway were highly up-regulated as compared to IFN (Table 3). The hierarchical cluster (FIG. 5B) illustrates that all isomers have transcriptional activity but generate different intensities.

The sum of AD (Σ AD) of the induced genes was determined for each isoform and IFN, and the transcriptional, antiviral and proliferative activities compared with IFN as a reference. FIG. 5 A shows that isoforms with an increased biological activity, as determined by their antiviral and anti-proliferative activities as compared to PEG-IFN, also have an increased transcriptional activity, while isoforms with a lower biological activity display a lower transcriptional activity, and that thus, in contrast to biological activity vs. binding assays, a positive correlation exists between biological and transcriptional activity.

Beside the effect of the isomers on the general transcriptional gene response, a varied up-regulation of individual genes was also observed. For example, the gene for interferon-induced nuclear phosphoprotein shows higher expression upon exposure to K49 and K31 than with K134 or K131. K49 and K31 isomers have a lower general transcriptional gene response than K134 or K131. This observation emphasizes the necessity of analyzing the general transcriptional gene response, as determined by the method of this invention, rather than to measure transcriptional expression levels of an individual gene, or a small selection of genes, for the determination of the transcriptional activity of a compound of interest.

The data of the microarray chips were also analyzed for transcriptional-specific side-effects which may indicate undesirable effects on the metabolism or vitality of cells by any isomer. The criteria for these analyses were similar to those described before, the only difference was that the data for each isomer were cross-compared. The result of this analysis showed no specific side-effect of any positional isomer.

Table 3: IFN Modulated Genes Dependent on the Pegylation Side To identify induced genes the ME15 cell line were cultured 48 hours in absence (untreated cell) or in presence of 100 U/ml IFN or a PEG-IFN sample. The expression level for each gene was calculated as normalised average difference of fluorescence intensity as compared to hybridisation to mismatched oligonucleotide, expressed in arbitrary units. Each investigation of the samples were measured in triplicate with labelled cRNA from three different cell plates. The criteria for a differentially expression of a gene by treatments with IFN or a PEG-IFN sample compared to the untreated cells were: if the mean value increase was at least twofold higher as in the untreated cells and the main value in the treated cells should be higher or at least 50 units. The mean value of the untreated cells should be lower than 50 units. In addition, the standard deviation had to be significantly smaller than the absolute change in average difference and the calculated confidence level of a gene was set greater than 97% (p value <0.03). By applying these criteria, 29 genes were found to be modulated.

TABLE 3

IFN modulated genes dependent on the pegylation side

| Gene discription | Seq ID No. | Untreated Intensity | IFN | PEG-IFN | K134 | K70 | K112 | K49 | K131 | K31 | K83 | K164 | K121 |
|---|---|---|---|---|---|---|---|---|---|---|---|---|---|
| Interferon-alpha induced 11.5 kDa protein (p27). | 1 | 4 | 609 | 921 | 876 | 705 | 639 | 514 | 481 | 344 | 444 | 284 | 202 |
| Bone marrow stromal antigen 2 (BST-2). | 2 | 11 | 554 | 714 | 681 | 701 | 507 | 544 | 542 | 463 | 476 | 390 | 362 |
| Interferon-induced protein 6-16 precursor (Ifi-6-16). | 3 | 42 | 783 | 863 | 890 | 795 | 875 | 594 | 499 | 607 | 580 | 547 | 437 |
| Interferon-induced17/15-kDa protein | 4 | 27 | 367 | 503 | 750 | 681 | 492 | 469 | 461 | 352 | 396 | 305 | 187 |
| mRNA expressed in osteoblast | 5 | 8 | 132 | 201 | 240 | 226 | 128 | 114 | 139 | 133 | 80 | 91 | 60 |
| ISGF-3 components (p91/p84) | 6 | 36 | 230 | 291 | 325 | 303 | 302 | 296 | 208 | 229 | 286 | 171 | 165 |
| ISGF-3 gamma (p48) | 7 | 45 | 213 | 175 | 179 | 196 | 255 | 210 | 145 | 155 | 227 | 109 | 126 |
| Hepatitis C-associated p44 | 8 | 11 | 93 | 111 | 126 | 102 | 93 | 65 | 89 | 69 | 69 | 57 | 54 |
| Interferon-induced 56 kDa protein (IFIT-1) | 9 | 9 | 93 | 120 | 171 | 162 | 70 | 75 | 100 | 84 | 77 | 65 | 39 |
| Interferon-inducible protein 9-27 | 10 | 8 | 74 | 134 | 220 | 200 | 112 | 89 | 66 | 69 | 53 | 49 | 25 |
| 2'-5'-oligoadenylate synthetase 1 (1.6 Kb) | 11 | 2 | 67 | 95 | 164 | 148 | 73 | 78 | 68 | 97 | 60 | 62 | 46 |
| Wilms' tumor associated protein (WIT-1). | 12 | 6 | 57 | 38 | 66 | 21 | 52 | 75 | 41 | 33 | 25 | 51 | 17 |
| Interferon regulatory factor 7 (IRF-7). | 13 | 10 | 52 | 72 | 102 | 83 | 54 | 68 | 61 | 84 | 56 | 72 | 51 |
| Interferon-induced 60 kDa protein | 14 | 13 | 48 | 58 | 68 | 85 | 37 | 51 | 56 | 46 | 38 | 46 | 30 |
| Nuclear autoantigen Sp-100 | 15 | 31 | 72 | 66 | 96 | 73 | 44 | 52 | 55 | 53 | 45 | 56 | 51 |
| KIAA0793 protein | 16 | 44 | 99 | 71 | 66 | 59 | 162 | 119 | 63 | 101 | 133 | 85 | 61 |
| 2'-5'-oligoadenylate synthetase 2 (71 kDa) | 17 | 32 | 71 | 112 | 144 | 150 | 68 | 61 | 71 | 53 | 48 | 52 | 52 |
| Histone H2A.g (H2A/g) | 18 | 14 | 39 | 28 | 58 | 27 | 93 | 82 | 25 | 59 | 74 | 59 | 28 |
| Interferon-induced nuclear phosphoprotein | 29 | 14 | 37 | 44 | 88 | 76 | 48 | 38 | 45 | 53 | 35 | 40 | 41 |
| Probable G protein-coupled receptor GPR12 | 19 | 31 | 52 | 79 | 50 | 60 | 82 | 92 | 75 | 121 | 25 | 83 | 37 |
| Cytochrome P450 XXIB (Steroid 21-hydroxylase) | 20 | 34 | 56 | 60 | 102 | 48 | 63 | 50 | 75 | 68 | 45 | 53 | 51 |
| putative tumor suppressor protein (101F6) | 21 | 24 | 35 | 31 | 47 | 42 | 62 | 76 | 45 | 53 | 58 | 51 | 51 |
| Transcription factor E2-alpha (TCF-3) | 22 | 23 | 32 | 32 | 50 | 52 | 26 | 35 | 74 | 31 | 31 | 55 | 22 |
| KIAA0691 protein | 23 | 41 | 56 | 59 | 110 | 106 | 82 | 90 | 114 | 93 | 81 | 125 | 79 |
| 5-hydroxytryptamine 1B receptor (Serotonin) | 24 | 19 | 26 | 21 | 64 | 24 | 26 | 25 | 26 | 32 | 27 | 34 | 23 |
| Coagulation factor XII precursor (Hageman factor) | 25 | 22 | 27 | 45 | 35 | 41 | 66 | 47 | 16 | 31 | 51 | 44 | 37 |
| Proto-oncogene tyrosine-protein kinase ABL1 (p150) | 26 | 21 | 26 | 31 | 50 | 27 | 16 | 30 | 69 | 43 | 38 | 23 | 31 |
| Protein AF1q | 27 | 13 | 16 | 34 | 47 | 65 | 50 | 61 | 43 | 49 | 40 | 46 | 46 |
| Guanidinoacetate N-methyltransferase (GAMT) | 28 | 21 | 15 | 16 | 15 | 43 | 71 | 50 | 36 | 18 | 41 | 54 | 23 |

The invention claimed is:

1. A method for determining the biological activity of a pegylated IFN which can modulate gene transcription, comprising the steps of
 a) contacting a host with said pegylated IFN;
 b) determining the transcriptional gene response of the genes of SEQ ID NOS: 1-29 of the host; and
 c) quantitating the determined transcriptional gene response induced by said IFN.

2. The method of claim 1, wherein the transcriptional gene response is determined by a DNA array technology.

3. The method of claim 2, wherein the DNA array technology is an oligonucleotide array technology.

4. The method of claim 1, wherein the pegylated protein is a specific isolated isoform of a pegylated IFN.

* * * * *

SEQUENCE LISTING

<160> NUMBER OF SEQ ID NOS: 29

<210> SEQ ID NO 1
<211> LENGTH: 597
<212> TYPE: DNA
<213> ORGANISM: Homo sapiens
<220> FEATURE:
<221> NAME/KEY: interferon-alpha inducible gene; ISG12 gene
<222> LOCATION: (1)..(597)
<223> OTHER INFORMATION: GenBank accession No. X67325

<400> SEQUENCE: 1
agctgaagtt gaggatctct tactctctaa gccacggaat taacccgagc aggcatggag    60
gcctctgctc tcacctcatc agcagtgacc agtgtggcca aagtggtcag ggtggcctct   120
ggctctgccg tagttttgcc cctggccagg attgctacag ttgtgattgg aggagttgtg   180

-continued

| | |
|---|---|
| gccatggcgg ctgtgcccat ggtgctcagt gccatgggct tcactgcggc gggaatcgcc | 240 |
| tcgtcctcca tagcagccaa gatgatgtcc gcggcggcca ttgccaatgg gggtggagtt | 300 |
| gcctcgggca gccttgtggg tactctgcag tcactgggag caactggact ctccggattg | 360 |
| accaagttca tcctgggctc cattgggtct gccattgcgg ctgtcattgc gaggttctac | 420 |
| tagctccctg cccctcgccc tgcagagaag agaaccatgc caggggagaa ggcacccagc | 480 |
| catcctgacc cagcgaggag ccaactatcc caaatatacc tgggtgaaat ataccaaatt | 540 |
| ctgcatctcc agaggaaaat aagaaataaa gatgaattgt tgcaactctt aaaaaaa | 597 |

<210> SEQ ID NO 2
<211> LENGTH: 996
<212> TYPE: DNA
<213> ORGANISM: Homo sapiens
<220> FEATURE:
<221> NAME/KEY: BST-2
<222> LOCATION: (1)..(996)
<223> OTHER INFORMATION: GenBank accession No. D28137

<400> SEQUENCE: 2

| | |
|---|---|
| gtggaattca tggcatctac ttcgtatgac tattgcagag tgcccatgga agacggggat | 60 |
| aagcgctgta agcttctgct ggggatagga attctggtgc tcctgatcat cgtgattctg | 120 |
| ggggtgccct tgattatctt caccatcaag gccaacagcg aggcctgccg ggacggcctt | 180 |
| cgggcagtga tggagtgtcg caatgtcacc catctcctgc aacaagagct gaccgaggcc | 240 |
| cagaagggct ttcaggatgt ggaggcccag gccgccacct gcaaccacac tgtgatggcc | 300 |
| ctaatggctt ccctggatgc agagaaggcc caaggacaaa agaaagtgga ggagcttgag | 360 |
| ggagagatca ctacattaaa ccataagctt caggacgcgt ctgcagaggt ggagcgactg | 420 |
| agaagagaaa accaggtctt aagcgtgaga atcgcggaca agaagtacta ccccagctcc | 480 |
| caggactcca gctccgctgc ggcgccccag ctgctgattg tgctgctggg cctcagcgct | 540 |
| ctgctgcagt gagatcccag gaagctggca catcttggaa ggtccgtcct gctcggcttt | 600 |
| tcgcttgaac attcccttga tctcatcagt tctgagcggg tcatgggca acacggttag | 660 |
| cggggagagc acggggtagc cggagaaggg cctctggagc aggtctggag gggccatggg | 720 |
| gcagtcctgg gtgtggggac acagtcgggt tgacccaggg ctgtctccct ccagagcctc | 780 |
| cctccggaca atgagtcccc cctcttgtct cccacccctga gattgggcat ggggtgcggt | 840 |
| gtgggggggca tgtgctgcct gttgttatgg gtttttttg cgggggggt tgctttttc | 900 |
| tggggtcttt gagctccaaa aaataaacac ttcctttgag ggagagcaaa aaaaaaaaa | 960 |
| aaaaaaaaa aaaaaaaaa aaagaattcc accaca | 996 |

<210> SEQ ID NO 3
<211> LENGTH: 6803
<212> TYPE: DNA
<213> ORGANISM: Homo sapiens
<220> FEATURE:
<221> NAME/KEY: interferon-inducible peptide (6-16) gene
<222> LOCATION: (1)..(6803)
<223> OTHER INFORMATION: GenBank accession No. U22970

<400> SEQUENCE: 3

| | |
|---|---|
| agatctatca tgatggccac atgaacacag gcttcactgg tcttaccata tgcccatgac | 60 |
| ccagaagcag ccagcctgag agaacaatgg aacaaagtga cttaatttcc aaagttctgg | 120 |
| gggtttataa acagcatatg gtatgtcaca tgactactgt gggattggaa aaagatcatg | 180 |
| taaatagagc actttgcaca gaccctggca tgcagcaagt gctcaataaa tgataggtgt | 240 |

-continued

| | | | | | |
|---|---|---|---|---|---|
| tgtttactaa | ttggactgaa | tggtgaaagg | cctgtgtgcc | ccagggggag | ctggtgatca | 300 |
| ggcttcacta | agcccagtat | ggccgtggct | ctcatctcag | tgtgacatgc | tttgaatacc | 360 |
| cttagcggct | ccaaaagtcc | tcagcttgaa | gtgcattttt | ctgccagcag | gcagcacaca | 420 |
| aatgttccgc | tgggcggagc | tgggagagag | gggaaaatga | aactctgcag | agtgcaggag | 480 |
| ctggagaga | ggggaaaatg | aaactgcaga | gtgcagaaat | agaaactccg | acagggattg | 540 |
| gctgcctagg | gtgagacgtg | ggaggatcca | caagtgatga | taaaaagcca | gccttcagcc | 600 |
| ggagaaccgt | ttactcgctg | ctgtgcccat | ctatcagcag | gctccgggct | gaagattgct | 660 |
| tctcttctct | cctccaaggt | aaactcagga | gcttatgaag | tgtgggcatt | caagctgcca | 720 |
| ccctctgcca | ggctgcctgt | ctgcctgtaa | atctcatgtt | ctgagagcca | ggaggcccct | 780 |
| tctcctggga | ggcagcactc | ctgggtccct | tttagtgctc | tgggctggga | cttgtctaag | 840 |
| aggatgggtt | ggagattttt | agggagatgg | gatgcaaaac | cccaagtggc | atgagaccca | 900 |
| gcttacaggt | gcaatatcag | cgatctgtgg | ccttaacact | gtcacctctt | ggagccttaa | 960 |
| ttacttcctc | tgtaaaagga | aagttaagtt | gcctttgctg | ctcaaaggac | tggagtattt | 1020 |
| tagaatcccc | tttattatag | gatccaatgt | gacagtgagt | tcatctttaa | ggatagatga | 1080 |
| agccatctgg | agtggttgtt | aaaaatgtgg | gcttggtggc | caggcgtggt | ggttcacgcc | 1140 |
| tgtaatccca | gcactttggg | aggccgagac | ccacggatca | cgaggtcagg | agatcgagac | 1200 |
| catcctggct | aacacagtga | aaccctgtct | ctactaaaaa | tacaaaaaaa | attagccggg | 1260 |
| cttggtggtg | ggcgcctgta | gtctcagcta | ctcgggaggc | tgaggcaggc | aggagaatgg | 1320 |
| catgaacctg | ggaggtggag | cttgcagtga | gatgagattg | cgccactgca | ctccagcctg | 1380 |
| ggcgacagag | aaagactcca | tctcaaaaaa | aaaaaaaaaa | aaaatgtggg | cttgggtatt | 1440 |
| agccaattgt | gggtttaaac | cctgactttg | ccatgacctg | gctaggcagc | cttgggaata | 1500 |
| ttacttaacc | tctctgagct | tcagtttcct | tatctataac | atgtggttga | taacaatggt | 1560 |
| acctacttcg | tggtgttgtt | ataggtacaa | gtggactgcg | tgccataaag | tgctaagtac | 1620 |
| tcaatacatg | agaggagttt | cttgtttttc | tttttaactt | aagaaaatag | cattgatctg | 1680 |
| acaaagatca | tattagaggt | gagtctgagg | gcatatgcat | tttccagttt | tgtggtataa | 1740 |
| aggaaagagc | ataggttcat | gaattctgac | tgtcttgaat | gtgtacccat | gttgcacaat | 1800 |
| ttgctgtgtg | acctttatcc | cttgtgatat | tgtaaaatat | attttttcat | cccccagttc | 1860 |
| ctggcataca | actcctaaaa | tccttggaat | cttcaaagtg | ataaatatct | tttgagtgat | 1920 |
| aactgtctaa | taagttgact | gatggctggc | atttcctctg | ggagggggag | agggctgaa | 1980 |
| ggttaagctg | attaccaatg | ggcagtgatt | taatcagtca | tgcctatgta | atgaagcctc | 2040 |
| cataaaaaca | caaaaggaca | gggtttgaca | agcttccaga | tagccgaata | caggaggtct | 2100 |
| ccagtgggtg | gtgcttctgg | agaggaatgg | aaactccatg | ccctttctcc | catacccttgc | 2160 |
| cctatgcatc | tcttcatctg | gagcatttgt | aatatccata | aggaaccagt | aaatgtagct | 2220 |
| gggtatggtg | gctgatgcct | gtaatctcag | cactttggga | ggctgaggca | ggcagattgc | 2280 |
| gtgagttcag | gagttcaaga | tcagcctggg | caacatggtg | aaaccccatc | tcaaaaaaaa | 2340 |
| aaaaaaaaat | tagttgggcg | tggtggtgca | tacctgtagt | cccagctatc | tggaggctga | 2400 |
| ggtgggagga | tcacttgagc | ctgggaggcg | aaggtctcag | tgagctgaga | tggggccact | 2460 |
| gcactccagc | ctgagcaata | gagtgagacc | ctgtctcaaa | acaacaacaa | gatcaatttt | 2520 |
| tttttttaa | agaaagaaac | cagtatatgt | aagtaaagtg | tttccctgag | ttctgtgagc | 2580 |

-continued

```
tgctctagca aattagtaaa actgcaggag ggaattgtgg gaacccccagt ttatagtcag    2640 tcagaaacac aggtaaaaca acctagggct tcgattggca gtctggggga ctgaaccctc    2700
aacatgtggg atcggccact atctacccat agtggtgtca gaattgaatt tgggaccct    2760 cagctggtgt tcaccagagg actgattgtt tgcttgctgg tggggagaaa cccccacact    2820
tctgctgtca gaagcctctc gtacggtgag ggaaactgag tttcttttc cacacaccct     2880 tctgtgcttt ctttctgaaa aaaaattaa gttgatgtga ggccaacgtt tggtgccagt     2940
agatattcaa tgcattgtaa gaatgagttt gtcttaaaaa ttttttaaa gcaaattcta     3000 tgcgtcaggc actgttcaaa gtgcgggata cagcgtggac cagttattaa attaacaagt    3060
accctctgaa atagactcta ttaatacccc aattttagaa ataaacaaac tgaagcccag    3120
agaagcaaag taccctagta tcctgcccaa ggtcacttgg gtacaaggcc aagaacaacc    3180
acagtcatga tattgacatc tgcggacgtt accacgtgcc aaacaccgtg cgaatccgca    3240
cagaatccgc acacccaccg gttggggcag ggacatctct gccactgatg cggagaggaa    3300
acggattccc gaggctcctg agagggatcc tgggttccat tcaccacacc tcgctgcttt    3360
ttactgattc agttggaact ggaagggaaa acaacgagc tgatgagctc caaaaatgct     3420
ccggggacca tctccctctc gcccgttcgc aggtctagtg acggagcccg cgcgcggcgc    3480
caccatgcgg cagaaggcgg tatccgtttt cttgtgctac ctgctgctct tcacttgcag    3540
tggggtggag gcaggtgaga atgcgggtaa ggatgcaggt aaggggacag gtaagggtgc    3600
aggtaaggat gcaagtaagg gtgcaggtaa ggatgcgggt aaggatgcag gtaaagatgc    3660
gggtaaggat gcaggtaagg atgcgggtaa ggatgcaggt aagggtgcag gtaaggatgc    3720
gggtaaggat gcaggtaagg atgcaggtaa gggtgcaggt aaggatgcag gtaaggatgt    3780
gggtaaggat gcaggtaagg gtgcaggtaa gggaacagat aagggtgcag gtaaggggac    3840
aagtaaggag gcatataagg gtgctgggg atgggaggag tgtgggataa aggagagagt     3900
ttcagggtcc ggggtgtaga gggtctggcg tgcttctgta gagaccctgg cgtccattcc    3960
aatggacagc gcaggggttgg tgtcgccaga gtcccagatt caaatcccac tactctgttc   4020
attcctccat cctaccgaaa tttactcgat gctagttctg tgccagctcg gcgcctaggg    4080
gaaagtccct tcccctctgt gaggctctct gagtaggaga gtggtggccc ccgcctccag    4140
gagtggtcct gagcatcaga cacagagtag gggacccctg tgtcccaccc caacaacccc    4200
actacgcttt gtctgctctc ctgcaggtaa gaaaaagtgc tcggagagct cggacagcgg    4260
ctccgggttc tggaaggccc tgaccttcat ggccgtcgga ggaggtgggt ctggagggcg    4320
aggatctcgg gcaggcgggg cgggcctctg ccgcggacgc tccctcacct gctcctgttc    4380
ctccaggact cgcagtcgcc gggctgcccg cgctgggctt caccggcgcc ggcatcgcgg    4440
ccaactcggt ggctgcctcg ctgatgagct ggtctgcgat cctgaatggg ggcggcgtgc    4500
ccgccggggg gctagtggcc acgctgcaga gcctcggtga gtgcggggcc tgggcctggt    4560
gggacgttct ttactattat tttcatcata catctgggga aactgaggca ctcaggaatt    4620 aagtaatta ctcaagtaat taagtagttt accaggaatt aagtgattct ttattattt     4680 attttgagac agagtctggc tgtgtcaccc aggcaggctg aagtgcagtg gtgtgatctt    4740
ggctcactgc aacctctgcc tccctggctc aagcgatttt cctgccacag cctcccaagt    4800
agctgggatt acaggcacac gccaccacgc ccggctaatt tttgtatttt tagtagagat    4860 gggggtttcac catgttggcc aggctggctc aaactcctga cctcagctga tccgcccgcc    4920
tcggcgtccc atagtgctag gattacaggc gtgagtcacc gcgtccggcc agaaattaag    4980
```

-continued

```
taacttactc aagtctccct gctagtttag accagagcct agattctgac ccagtcagta    5040
caatgcgaga agccccattc tcagcctcaa aggctgggtg cctcactgat gctttggcca    5100
aatcacaagc tcagttccc  tcagcggtgc gtggggatga tcatcctcag tttaacattt    5160
tttgaatctg ctcaatctca gagaccacag tagcaaagaa acatagtaga gtaactcaaa    5220
tcaatctcac accaaactgg tcttgacttg cacttttga  acaccatgga gggaacagat    5280
aacagagctc acagtgactc ttctatcgat tgatcaatct attgatctat ttattataga    5340
taaaggtcaa acaaggtct  cacactgcca ggttggaatg cagtgcatga tcacagctca    5400
cagcagcctc gaactcccag gttcaagcta tcttcctgcc tcagattccc aagtagctgg    5460
gactataggc gcataccgcc acacactggc tttttttttt ttttttttt  tttttttgt     5520
agagacgggg tctcattgtg ttgcccagga tggtcttgaa ttcctgggct caagcaatcc    5580
tcccactttg gcctcccaaa gtgttgagac tgcaagcatg agccactgtg ctggcccaga    5640
gtgactcata aaaatggcc  ttacttccct ctctctcctc tctcccacc  cacccccacc    5700
tctctctcgc gctctgaggc ctccaaaatc ctggagaaaa cctgccctg  acaaacttcc    5760
ctctctgcct ttctgaacct cgcatctcct cttctctcaa ttctgaatgg caaaagccca    5820
aagaaccagc ccaaaagaag agagccctgc tcagacgggg ccacacccct gcaatgggag    5880
gggaagagtg tgggcgagcc cagggacacc tctgggctat cagctagttg tcctctcaca    5940
tggcacatag ctgtgacaag atgaaatgat ccctggcttg tgaaccccc  acacccacac    6000
agggctccat gaaggtggct gttagcatga ttaataacat ggcgtttcca tgcagacat     6060
caggtgaagg agccattatt tttgcctttt tcatcactga aacacatctc tgatttggga    6120
tgtcaaggca agtaaaaat  gggactcact ttgtagtagt gccatcccct ctcagggcct    6180
ctgtttctcc atctagacat aaggggttgg actcaaccaa tggtttccag acatttggat    6240
tcccaggcct ggcacttggg cccagtgact catctgtgtt tgctttacag gggctggtgg    6300
cagcagcgtc gtcataggta atattggtgc cctgatgcgg tacgccaccc acaagtatct    6360
cgatagtgag gaggatgagg agtagccagc agctcccaga acctcttctt ccttcttggc    6420
ctaactcttc cagttaggat ctagaacttt gcctttttt  tttttttt   tttttttga     6480
gatgggttct cactatattg tccaggctag agtgcagtgg ctattcacag atgcgaacat    6540
agtacactgc agcctccaac tcctagcctc aagtgatcct cctgtctcaa cctcccaagt    6600
aggattacaa gcatgcgccg acgatgccca gaatccagaa ctttgtctat cactctcccc    6660
aacaacctag atgtgaaaac agaataaact tcacccagaa aacactttgt cctgctgtca    6720
atcatgtttg cagtgagaag cccaaaacaa tctggctctg gcctgcacca tccacacacc    6780
cccattccca ttttccctc  gag                                           6803
```

```
<210> SEQ ID NO 4
<211> LENGTH: 634
<212> TYPE: DNA
<213> ORGANISM: Homo sapiens
<220> FEATURE:
<221> NAME/KEY: interferon-induced 17-kDa/15-kDa protein
<222> LOCATION: (1)..(634)
<223> OTHER INFORMATION: GenBank accession No. M13755

<400> SEQUENCE: 4
cggctgagag gcagcgaact catctttgcc agtacaggag cttgtgccgt ggcccacagc      60
ccacagccca cagccatggg ctgggacctg acggtgaaga tgctggcggg caacgaattc     120
```

-continued

```
caggtgtccc tgagcagctc catgtcggtg tcagagctga aggcgcagat cacccagaag      180
attggcgtgc acgccttcca gcagcgtctg gctgtccacc cgagcggtgt ggcgctgcag      240
gacagggtcc cccttgccag ccagggcctg ggccctggca gcacggtcct gctggtggtg      300
gacaaatgcg acgaacctct gagcatcctg gtgaggaata caagggccg cagcagcacc       360 tacgaggtcc ggctgacgca gaccgtggcc cacctgaagc agcaagtgag cgggctggag      420
ggtgtgcagg acgacctgtt ctggctgacc ttcgagggga agcccctgga ggaccagctc      480
ccgctggggg agtacggcct caagcccctg agcaccgtgt tcatgaatct gcgcctgcgg      540
ggaggcggca cagagcctgg cgggcggagc taagggcctc caccagcatc cgagcaggat      600
caagggccgg aaataaaggc tgttgtaaga gaat                                  634
```

```
<210> SEQ ID NO 5
<211> LENGTH: 2058
<212> TYPE: DNA
<213> ORGANISM: Homo sapiens
<220> FEATURE:
<221> NAME/KEY: mRNA expressed in osteoblast
<222> LOCATION: (1)..(2058)
<223> OTHER INFORMATION: GenBank accession No. AB000115

<400> SEQUENCE: 5
```

```
gcacgaggaa gccacagatc tcttaagaac tttctgtctc caaaccgtgg ctgctcgata       60
aatcagacag aacagttaat cctcaattta agcctgatct aaccctaga aacagatata      120 gaacaatgga agtgacaaca agattgacat ggaatgatga aaatcatctg cgcaactgct      180
tggaaatgtt tctttgagtc ttctctataa gtctagtgtt catggaggta gcattgaaga      240
tatggttgaa agatgcagcc gtcagggatg tactataaca atggcttaca ttgattacaa      300
tatgattgta gcctttatgc ttggaaatta tattaattta cgtgaaagtt ctacagagcc      360
aaatgattcc ctatggtttt cacttcaaaa gaaaaatgac accactgaaa tagaaacttt      420
actcttaaat acagcaccaa aaattattga tgagcaactg gtgtgtcgtt atcgaaaac       480 ggatattttc attatatgtc gagataataa aatttatcta gataaaatga taacaagaaa      540
cttgaaacta aggtttttatg ccaccgtca gtatttggaa tgtgaagttt ttcgagttga      600
aggaattaag gataacctag acgacataaa gaggataatt aaagccagag agcacagaaa      660
taggcttcta gcagacatca gagactatag gccctatgca gacttggttt cagaaattcg      720
tattcttttg gtgggtccag ttgggtctgg aaagtccagt ttttcaatt cagtcaagtc       780 tattttttcat ggccatgtga ctggccaagc cgtagtgggg tctgataccca ccagcataac     840 cgagcggtat aggatatatt ctgttaaaga tggaaaaaat ggaaaatctc tgccatttat      900
gttgtgtgac actatgggc tagatggggc agaaggagca ggactgtgca tggatgacat      960
tccccacatc ttaaaaggtt gtatgccaga cagatatcag tttaattccc gtaaaccaat     1020
tacacctgag cattctactt ttatcacctc tccatctctg aaggacagga ttcactgtgt     1080
ggcttatgtc ttagacatca actctattga caatctctac tctaaaatgt ggcaaaagt     1140 gaagcaagtt cacaaagaag tattaaactg tggtatagca tatgtggcct tgcttactaa     1200
agtggatgat tgcagtgagg ttcttcaaga caacttttta aacatgagta gatctatgac     1260
ttctcaaagc cgggtcatga atgtccataa aatgctaggc attcctattt ccaatatttt     1320
gatggttgga aattatgctt cagatttgga actggacccc atgaaggata ttctcatcct     1380
ctctgcactg aggcagatgc tgcgggctgc agatgatttt ttagaagatt tgcctcttga     1440
ggaaactggt gcaattgaga gagcgttaca gccctgcatt tgagataagt tgcccttgatt    1500
```

```
ctgacatttg gcccagcctg tactggtgtg ccgcaatgag agtcaatctc tattgacagc    1560
ctgcttcaga ttttgctttt gttcgttttg ccttctgtcc ttggaacagt catatctcaa    1620
gttcaaaggc caaaacctga gaagcggtgg gctaagatag gtcctactgc aaaccacccc    1680
tccatatttc cgtaccattt acaattcagt ttctgtgaca tctttttaaa ccactggagg    1740
aaaaatgaga tattctctaa tttattcttc tataacactc tatatagagc tatgtgagta    1800
ctaatcacat tgaataatag ttataaaatt attgtataga catctgcttc ttaaacagat    1860
tgtgagttct ttgagaaaca gcgtggattt tacttatctg tgtattcaca gagcttagca    1920
cagtgcctgg taatgagcaa gcatacttgc cattactttt ccttcccact ctctccaaca    1980
tcacattcac tttaaatttt tctgtatata gaaaggaaaa ctagcctggg caacatgatg    2040 aaacccatc tccactgc                                                   2058

<210> SEQ ID NO 6
<211> LENGTH: 2607
<212> TYPE: DNA
<213> ORGANISM: Homo sapiens
<220> FEATURE:
<221> NAME/KEY: transcription factor ISGF-3
<222> LOCATION: (1)..(2607)
<223> OTHER INFORMATION: GenBank accession No. M97936

<400> SEQUENCE: 6
attaaacctc tcgccgagcc cctccgcaga ctctgcgccg gaaagtttca tttgctgtat      60
gccatcctcg agagctgtct aggttaacgt tcgcactctg tgtatataac ctcgacagtc     120
ttggcaccta acgtgctgtg cgtagctgct ccttttggttg aatccccagg cccttgttgg    180
ggcacaaggt ggcaggatgt ctcagtggta cgaacttcag cagcttgact caaaattcct     240
ggagcaggtt caccagcttt atgatgacag ttttcccatg gaaatcagac agtacctggc     300
acagtggtta gaaaagcaag actgggagca cgctgccaat gatgtttcat ttgccaccat     360
ccgttttcat gacctcctgt cacagctgga tgatcaatat agtcgctttt ctttggagaa     420
taacttcttg ctacagcata acataaggaa aagcaagcgt aatcttcagg ataattttca     480
ggaagaccca atccagatgt ctatgatcat ttacagctgt ctgaaggaag aaaggaaaat     540
tctggaaaac gcccagagat ttaatcaggc tcagtcgggg aatattcaga gcacagtgat     600
gttagacaaa cagaaagagc ttgacagtaa agtcagaaat gtgaaggaca aggttatgtg     660
tatagagcat gaaatcaaga gcctggaaga tttacaagat gaatatgact tcaaatgcaa     720
aaccttgcag aacagagaac acgagaccaa tggtgtggca aagagtgatc agaaacaaga     780
acagctgtta ctcaagaaga tgtatttaat gcttgacaat aagagaaagg aagtagttca     840
caaaataata gagttgctga atgtcactga acttacccag aatgccctga ttaatgatga     900
actagtggag tggaagcgga gacagcagag cgcctgtatt gggggccgc ccaatgcttg      960 cttggatcag ctgcagaact ggttcactat agttcgggag agtctgcagc aagttcggca    1020
gcagcttaaa aagttggagg aattggaaca gaaatacacc tacgaacatg accctatcac    1080
aaaaaacaaa caagtgttat gggaccgcac cttcagtctt ttccagcagc tcattcagag    1140
ctcgtttgtg gtggaaagac agcccctgca tgccaacgcac cctcagaggc cgctggtctt    1200
gaagacaggg gtccagttca ctgtgaagtt gagactgttg gtgaaattgc aagagctgaa    1260 ttataattg aaagtcaaag tcttatttga taaagatgtg aatgagagaa atacagtaaa    1320
aggatttagg aagttcaaca ttttgggcac gcacacaaaa gtgatgaaca tggaggagtc    1380
```

-continued

```
caccaatggc agtctggcgg ctgaatttcg gcacctgcaa ttgaaagaac agaaaaatgc      1440
tggcaccaga acgaatgagg gtcctctcat cgttactgaa gagcttcact cccttagttt      1500
tgaaacccaa ttgtgccagc ctggtttggt aattgacctc gagacgacct ctctgcccgt      1560
tgtggtgatc tccaacgtca gccagctccc gagcggttgg gcctccatcc tttggtacaa      1620
catgctggtg gcggaaccca ggaatctgtc cttcttcctg actccaccat gtgcacgatg      1680
ggctcagctt tcagaagtgc tgagttggca gttttcttct gtcaccaaaa gaggtctcaa      1740
tgtggaccag ctgaacatgt tgggagagaa gcttcttggt cctaacgcca gccccgatgg      1800
tctcattccg tggacgaggt tttgtaagga aaatataaat gataaaaatt ttcccttctg      1860
gctttggatt gaaagcatcc tagaactcat taaaaaacac ctgctccctc tctggaatga      1920
tgggtgcatc atgggcttca tcagcaagga gcgagagcgt gccctgttga aggaccagca      1980 gccgggacc ttcctgctgc ggttcagtga gagctcccgg aaggggcca tcacattcac        2040 atgggtggag cggtcccaga acggaggcga acctgacttc catgcggttg aaccctacac      2100
gaagaaagaa ctttctgctg ttactttccc tgacatcatt cgcaattaca aagtcatggc      2160
tgctgagaat attcctgaga atccctgaa gtatctgtat ccaaatattg acaaagacca       2220
tgcctttgga aagtattact ccaggccaaa ggaagcacca gagccaatgg aacttgatgg      2280
ccctaaagga actggatata tcaagactga gttgatttct gtgtctgaag tgtaagtgaa      2340
cacagaagag tgacatgttt acaaacctca agccagcctt gctcctggct ggggcctgtt      2400
gaagatgctt gtattttact tttccattgt aattgctatc gccatcacag ctgaacttgt      2460
tgagatcccc gtgttactgc ctatcagcat tttactactt taaaaaaaaa aaaaaaagcc      2520
aaaaaccaaa tttgtattta aggtatataa attttcccaa aactgatacc ctttgaaaaa      2580
gtataaataa aatgagcaaa agttgaa                                         2607
```

<210> SEQ ID NO 7
<211> LENGTH: 1584
<212> TYPE: DNA
<213> ORGANISM: Homo sapiens
<220> FEATURE:
<221> NAME/KEY: ISGF3-gamma
<222> LOCATION: (1)..(1584)
<223> OTHER INFORMATION: GenBank accession No. M87503

<400> SEQUENCE: 7

```
gatcagaggg cgatcagctg gacagcaact caggatggca tcaggcaggg cacgctgcac       60
ccgaaaactc cggaactggg tggtggagca agtggagagt gggcagtttc ccggagtgtg      120 ctggatgat acagctaaga ccatgttccg gattccctgg aaacatgcag gcaagcagga      180
cttccgggag gaccaggatg ctgccttctt caaggcctgg gcaatattta agggaaagta      240
taaggagggg gacacaggag gtccagctgt ctggaagact cgcctgcgct gtgcactcaa      300
caagagttct gaatttaagg aggttcctga gggggccgc atggatgttg ctgagcccta      360
caaggtgtat cagttgctgc caccaggaat cgtctctggc cagccaggga ctcagaaagt      420
accatcaaag cgacagcaca gttctgtgtc tctgagagg aaggaggaag aggatgccat      480
gcagaactgc acactcagtc cctctgtgct ccaggactcc ctcaataatg aggaggaggg      540
ggccagtggg ggagcagtcc attcagacat tgggagcagc agcagcagca gcagccctga      600
gccacaggaa gttacagaca caactgaggc cccctttcaa ggggatcaga ggtccctgga      660
gtttctgctt cctccagagc cagactactc actgctgctc accttcatct acaacgggcg      720
cgtggtgggc gaggcccagg tgcaaagcct ggattgccgc cttgtggctg agccctcagg      780
```

```
ctctgagagc agcatggagc aggtgctgtt ccccaagcct ggcccactgg agcccacgca      840
gcgcctgctg agccagcttg agaggggcat cctagtggcc agcaaccccc gaggcctctt      900
cgtgcagcgc ctttgcccca tccccatctc ctggaatgca cccaggctc cacctgggcc       960 aggcccgcat ctgctgccca gcaacgagtg cgtggagctc ttcagaaccg cctacttctg     1020
cagagacttg gtcaggtact tcagggcct gggcccccca ccgaagttcc aggtaacact      1080
gaatttctgg gaagagagcc atggctccag ccatactcca cagaatctta tcacagtgaa     1140
gatggagcag gcctttgccc gatacttgct ggagcagact ccagagcagc aggcagccat     1200
tctgtccctg gtgtagagcc tgggggaccc atcttccacc tcacctcttt gttcttcctg     1260
tctcctttga gtagactca ttcttcacac gattgacctg tcctctttgt gataattctc      1320
agtagttgtc cgtgataatc gtgtcctgaa atcctcgca cacactggct ggtggagaac      1380
tcaaggctaa ttttttatcc tttttttttt tttattttg agatatacgc cctctttcat      1440
ctgtaaggga ctaggaaatt ccaaatggtg tgaacccagg gggcctttcc ctcttccctg     1500
acctcccaac tctaaagcca agcactttat attttctct tagatattca ctaaggactt      1560
aaaataaaat ttttttgaaa gagg                                             1584

<210> SEQ ID NO 8
<211> LENGTH: 483
<212> TYPE: DNA
<213> ORGANISM: Homo sapiens
<220> FEATURE:
<221> NAME/KEY: hepatitis C-associated microtubular aggregate
<222> LOCATION: (1)..(483)
<223> OTHER INFORMATION: GenBank accession No. D28915

<400> SEQUENCE: 8
cctctggttg cctttcctga gataatccac taagaatatt ttgtgtttct tttctcaggg       60
aatctaaggg aggaaattat caactgtgca caaggaaaaa aatagatatg tgaaaggttc      120
acgtaaattt cctcacatca cagaagatta aaattcagaa aggagaaaac acagaccaaa      180
gagaagtatc taagaccaaa gggatgtgtt ttattaatgt ctaggatgaa gaaatgcata      240
gaacattgta gtacttgtaa ataactagaa ataacatgat ttagtcataa ttgtgaaaaa      300
taataataat ttttcttgga tttatgttct gtatctgtga aaaataaat tcttataaa       360 actcgggtct aacttgagag tgtgtgtgat tttggaaaaa ttatgatttg tcagcatctt      420
ctgatattca ctgctttcat cttaattttg ccttctgatt ttatttctaa agtatgtgat      480
ttt                                                                    483

<210> SEQ ID NO 9
<211> LENGTH: 1642
<212> TYPE: DNA
<213> ORGANISM: Homo sapiens
<220> FEATURE:
<221> NAME/KEY: interferon-inducible 56 Kd protein_(IFIT-1)
<222> LOCATION: (1)..(1642)
<223> OTHER INFORMATION: GenBank accession No. M24594

<400> SEQUENCE: 9
ccagatctca gaggagcctg gctaagcaaa ccctgcaga acggctgcct aatttacagc       60
aaccatgagt acaaatggtg atgatcatca ggtcaaggat agtctggagc aattgagatg      120
tcactttaca tggagttat ccattgatga cgatgaaatg cctgattag aaaacagagt       180 cttggatcag attgaattcc tagacaccaa atacagtgtg gaatacaca acctactagc       240
```

```
ctatgtgaaa cacctgaaag gccagaatga ggaagccctg aagagcttaa aagaagctga      300
aaacttaatg caggaagaac atgacaacca agcaaatgtg aggagtctgg tgacctgggg      360
caactttgcc tggatgtatt accacatggg cagactggca gaagcccaga cttacctgga      420
caaggtggag aacatttgca agaagctttc aaatcccttc cgctatagaa tggagtgtcc      480
agaaatagac tgtgaggaag gatgggcctt gctgaagtgt ggaggaaaga attatgaacg      540
ggccaaggcc tgctttgaaa aggtgcttga agtggaccct gaaaaccctg aatccagcgc      600
tgggtatgcg atctctgcct atcgcctgga tggctttaaa ttagccacaa aaaatcacaa      660 gccatttttct ttgcttcccc taaggcaggc tgtccgctta aatccagaca atggatatat      720
taaggttctc cttgccctga agcttcagga tgaaggacag gaagctgaag gagaaaagta      780
cattgaagaa gctctagcca acatgtcctc acagacctat gtctttcgat atgcagccaa      840
gttttaccga agaaaaggct ctgtggataa agctcttgag ttattaaaaa aggccttgca      900
ggaaacaccc acttctgtct tactgcatca ccagataggg ctttgctaca aggcacaaat      960
gatccaaatc aaggaggcta caaaagggca gcctagaggg cagaacagag aaaagctaga     1020
caaaatgata agatcagcca tatttcattt tgaatctgca gtggaaaaaa agcccacatt     1080
tgaggtggct catctagacc tggcaagaat gtatatagaa gcaggcaatc acagaaaagc     1140
tgaagagaat tttcaaaaat tgttatgcat gaaaccagtg gtagaagaaa caatgcaaga     1200
catacatttc tactatggtc ggtttcagga atttcaaaag aaatctgacg tcaatgcaat     1260
tatccattat ttaaaagcta taaaaataga acaggcatca ttaacaaggg ataaaagtat     1320
caattctttg aagaaattgg ttttaaggaa acttcggaga aaggcattag atctggaaag     1380
cttgagcctc cttgggttcg tctataaatt ggaaggaaat atgaatgaag ccctggagta     1440
ctatgagcgg gccctgagac tggctgctga ctttgagaac tctgtgagac aaggtcctta     1500
ggcacccaga tatcagccac tttcacattt catttcattt tatgctaaca tttactaatc     1560 atctttctg cttactgttt tcagaaacat tataattcac tgtaatgatg taattcttga     1620
ataataaatc tgacaaaata tt                                             1642
```

<210> SEQ ID NO 10
<211> LENGTH: 853
<212> TYPE: DNA
<213> ORGANISM: Homo sapiens
<220> FEATURE:
<221> NAME/KEY: interferon-inducible protein 9-27
<222> LOCATION: (1)..(853)
<223> OTHER INFORMATION: GenBank accession No. J04164

<400> SEQUENCE: 10

```
ctagtcctga cttcacttct gatgaggaag cctctctcct tagccttcag cctttcctcc       60
caccctgcca taagtaattt gatcctcaag aagttaaacc acacctcatt ggtccctggc      120
taattcacca atttacaaac agcaggaaat agaaacttaa gagaaataca cacttctgag      180
aaactgaaac gacaggggaa aggaggtctc actgagcacc gtcccagcat ccggacacca      240
cagcggccct tcgctccacg cagaaaacca cacttctcaa accttcactc aacacttcct      300
tccccaaagc cagaagatgc acaaggagga acatgaggtg gctgtgctgg ggcacccccc      360
cagcaccatc cttccaaggt ccaccgtgat caacatccac agcgagacct ccgtgcccga      420
ccatgtcgtc tggtccctgt tcaacaccct cttcttgaac tggtgctgtc tgggcttcat      480
agcattcgcc tactccgtga agtctaggga caggaagatg gttggcgacg tgaccggggc      540
ccaggcctat gcctccaccg ccaagtgcct gaacatctgg gccctgattc tgggcatcct      600
```

-continued

```
catgaccatt ggattcatcc tgtcactggt attcggctct gtgacagtct accatattat    660
gttacagata atacaggaaa aacggggtta ctagtagccg cccatagcct gcaacctttg    720
cactccactg tgcaatgctg gccctgcacg ctggggctgt tgcccctgcc ccttggtcc     780 tgcccctaga tacagcagtt tatacccaca cacctgtcta cagtgtcatt caataaagtg    840
cacgtgcttg tga                                                       853
```

<210> SEQ ID NO 11
<211> LENGTH: 1377
<212> TYPE: DNA
<213> ORGANISM: Homo sapiens
<220> FEATURE:
<221> NAME/KEY: 2-5A synthetase induced by interferon
<222> LOCATION: (1)..(1377)
<223> OTHER INFORMATION: X04371

<400> SEQUENCE: 11

```
aacgaaacca acagcagtcc aagctcagtc agcagaagag ataaaagcaa acaggtctgg     60
gaggcagttc tgttgccact ctctctcctg tcaatgatgg atctcagaaa tacccccagcc   120 aaatctctgg acaagttcat tgaagactat ctcttgccag acacgtgttt ccgcatgcaa    180
atcaaccatg ccattgacat catctgtggg ttcctgaagg aaaggtgctt ccgaggtagc    240
tcctaccctg tgtgtgtgtc caaggtggta aagggtggct cctcaggcaa gggcaccacc    300
ctcagaggcc gatctgacgc tgacctggtt gtcttcctca gtcctctcac cacttttcag    360
gatcagttaa atcgccgggg agagttcatc aggaaaatta ggagacagct ggaagcctgt    420
caaagagaga gagcattttc cgtgaagttt gaggtccagg ctccacgctg ggcaaccccc    480
cgtgcgctca gcttcgtact gagttcgctc cagctcgggg aggggtggag gttcgatgtg    540
ctgcctgcct ttgatgccct gggtcagttg actggcagct ataaacctaa cccccaaatc    600
tatgtcaagc tcatcgagga gtgcaccgac ctgcagaaag agggcgagtt ctccacctgc    660
ttcacagaac tacagagaga cttcctgaag cagcgcccca ccaagctcaa gagcctcatc    720
cgcctagtca agcactggta ccaaaattgt aagaagaagc ttgggaagct gccacctcag    780
tatgccctgg agctcctgac ggtctatgct tgggagcgag ggagcatgaa aacacatttc    840
aacacagccc agggatttcg gacggtcttg gaattagtca taaactacca gcaactctgc    900
atctactgga caaagtatta tgactttaaa accccatta ttgaaaagta cctgagaagg    960
cagctcacga aacccacgcc tgtgatcctg gaccggcgg accctacagg aaacttgggt    1020
ggtggagacc caaagcgttg gaggcagctg gcacaagagg ctgaggcctg gctgaattac   1080
ccatgcttta agaattggga tgggtcccca gtgagctcct ggattctgct ggtgagacct   1140
cctgcttcct ccctgccatt catccctgcc cctctccatg aagcttgaga catatagctg   1200
gagaccattt ttccaaaga acttacctct tgccaaaggc catttatatt catatagtga   1260
caggctgtgc tccatatttt acagtcattt tggtcacaat cgagggtttc tggaattttc   1320
acatcccttg tccagaattc attcccctaa gagtaataat aaataatctc taacacc     1377
```

<210> SEQ ID NO 12
<211> LENGTH: 5503
<212> TYPE: DNA
<213> ORGANISM: Homo sapiens
<220> FEATURE:
<221> NAME/KEY: Wilms' tumor gene
<222> LOCATION: (1)..(5503)
<223> OTHER INFORMATION: GenBank accession No. X69950
<220> FEATURE:

```
<221> NAME/KEY: misc_feature
<222> LOCATION: (2041)..(2041)
<223> OTHER INFORMATION: undefined nucleotide
<220> FEATURE:
<221> NAME/KEY: misc_feature
<222> LOCATION: (2083)..(2083)
<223> OTHER INFORMATION: undefined nucleotide
<220> FEATURE:
<221> NAME/KEY: misc_feature
<222> LOCATION: (2186)..(2186)
<223> OTHER INFORMATION: undefined nucleotide
<220> FEATURE:
<221> NAME/KEY: misc_feature
<222> LOCATION: (2187)..(2187)
<223> OTHER INFORMATION: undefined nucleotide
<220> FEATURE:
<221> NAME/KEY: misc_feature
<222> LOCATION: (2488)..(2488)
<223> OTHER INFORMATION: undefined nucleotide
<220> FEATURE:
<221> NAME/KEY: misc_feature
<222> LOCATION: (3386)..(3386)
<223> OTHER INFORMATION: undefined nucleotide
<220> FEATURE:
<221> NAME/KEY: misc_feature
<222> LOCATION: (3718)..(3718)
<223> OTHER INFORMATION: undefined nucleotide
<220> FEATURE:
<221> NAME/KEY: misc_feature
<222> LOCATION: (3720)..(3720)
<223> OTHER INFORMATION: undefined nucleotide
<220> FEATURE:
<221> NAME/KEY: misc_feature
<222> LOCATION: (3938)..(3938)
<223> OTHER INFORMATION: undefined nucleotide

<400> SEQUENCE: 12
ggtgcgctca ggactggaag caactctcag ttcatcaatt tcatgggcct acgtatctgc    60
tctggccacg gcctggcctc catccccact gtggcattaa tgcagaacaa attgagacat   120
atcctctata taattagttc cagaatttaa aaagatttac ggtataataa tagaggcagt   180
gccgcggaat cctttcactg aggactctcg gggagctcgg ggaccatctc gcggtggcat   240
cagaacagac gagtaacccc agcggctcca ggcactgcga actgggggag aggggggaaat  300 tttgcaccgc attcggcagt acctaacggt tccgggctcc cagataggggt cagcgaggag   360 agttaggaca gtaagtgggg actggttaaa aaaaatcgac ttaattttga aatgatcaga   420
agaagctggg agtagttatc acaaagcccc tcccttgccc ccccttttt ttaattgaag    480 gaatgacgtt gaaatttca ccgccagcgc ggggctggga accatcctaa acacttgccc    540
tgcagccccg agtgggcaga ttccgaagag ttggagtcgg cggggagggg aggaacagct   600
gttgggctgt cttgcgcgtg gggctcgggg cgcgggcccc ggggagaggc gctagtcgaa    660
agcttgttcc tctcccgcga caggcagcag cgaggtcgag ccactcttta ttacggcctg   720
cgggccccgc gcgcagtgtg gctgtccccg cccttgaccg accgcagcgc tttggggtgt   780
ttattcagtt gtccgcggcc gctgggtgac tcccggaggc ggcccaggcg tgcgcactgg   840
tccctggggt tgcggctgta gcagcccagc tccgcgctct gtcagatgca gtggacagcg   900
ccggggtgaa agtaagggtt gagaaatcct cactgccctg ctcctaccca gcctcgattt   960
tttcatattg caataattat gcaccttcga ggccgggatg cctgcgcttt gccagtgtat  1020
caacgccaca tggttttcca ggggctgtcc tcgcctctgc atcccattag ctctgaagag  1080 gtagagggggt ggtgggtaaa acctccaact ggacgttgag agacccgggt ttcagctcgg  1140
cgttgccact aacttgtttc ctgtccttaa acagtagtag taacaaaaac tgtaaagttg  1200
attgagtcaa aggcccacac tgctctccta tctaatcctc agaacaactc tatgaggtgg  1260
```

-continued

```
gcgctagtat cccattatcc cgtttgacca gtaaggaaac tgaggctcag agagactgcg    1320
gaactcgtct agggtcacac agctgttggt tacctggcag agctgaggtt ccattctggg    1380
gccaccaacc ccttgctctt tacgtgcgct ccatagactg cctctccttc ggctgtctgg    1440
gcctcagttt ccttctctgt aaaacgagaa gtttaatctg cagctttctt tgccaatcgg    1500
tggttcagac caggaacctc tgctacagat ctcggcgctg acaggggtaa aaggtgggt    1560 gaaagaaggg ggcgcccagt tttccacagc ctgcttttct ctgggacctc gcgaagggcg    1620
ggcctcgcga gctaaaggag gtacaggaga gcgcctatcg tccgcggcgg gtgaaggtgc    1680
tacctgcctt cgtgctaggc tgtgagtcct ggtgcttagc tcagggcgcc aaggccagtg    1740
tagctggcat gtccccttg gaaaacctca ggtctcccgc agagaacgtt acccacaaca    1800
aagaagagga cagagaggca tggagcgccc tgcgactgca ggagtacgtc agttccccag    1860
cgctggctta gtgtcgcctg gcttccgggg catgtggatc cgttgggtc gtacggagac    1920 ttcctgtcgg gtccctgggg tcctccgact gcggctcctc agcttagcac tttcttcttg    1980
gccccgcagg ctgcagggaa ctcctcccac ctctttagtc ggagaagtcc aagtcgggcg    2040
agggggcacc ccggggttcg caccggtgct cttcccctcc ccncccccac aaggattctg    2100
agaaaataaa tggcagagga gagaggagtt ctacatttgc ttggctctcc tttcctccta    2160 tccacccta catccctcac cccggnncaa aaacttattt ttgaaaaatg ttggcagaga    2220
tttacgtgtc tttgccttac ctgggtttca caaacacaac gactcacatt caagccagcc    2280
tcccttcaga taacctcctc tcccccgct aaaagtgcca aggatggtaa aagaagaaac    2340
aatctcaatc ttttcgtttg gaaatgaaag tccccggctt ttcataaagg gctcctcgcc    2400
cctcacagtt gagtcctagt taagaaaaac gacttccaag tagaaataat aggcggggag    2460
aaggaaggga gatacaggga tctggggngt tcttagggca actggcagtg aattttgtct    2520
cgagagtcct ttctccactc aaaaaaaccaa acgcgcgagc cccgcgaaag gtttagggat    2580
agatcgtgtg ggagaggact gagcagagag cgtgggggca gtgtcttgta gaatctttct    2640
tttcttaata ataattttaa aagcttctga gtggagacga cgcaaagtca agcagcaaag    2700
gtggcctggg aggcaagcgg agggctcaag tgccgcatct ttaccctcag ggtctcctgc    2760
gcctacggga tgcgcattcc caagaagtgc gcccttcgag taagtcctgg gcccgcacac    2820
acttcgggtc cgcagccaga atttaatggc gacaacgttt atgcaatgca agctaaaaac    2880
caaagcgtaa aaaattacta tgtcatttat tgaaacgcca ttctttgtca aactgcaact    2940
actttgcttc acataagttt ggctggaaag cttgcagccc cagcccgggc cagccaggta    3000
caggaggccg gactgcaacc ggttgcttcc ctcccgtcgc gcctggccgt cccacgctgc    3060
gccgtcgctg ctgcctcctg gcgcccctgg gattttatac gcacctctga aacacgctcc    3120
gctccggccc ccggttcttc tccttgccta ggggttgttt cccaatagat actgactcct    3180
ttagaagatc caaaaaccaa accaaaacac ccctacccg ccccaaacac ctgctctggg    3240 gcgcggggc tgccaaacag agactagacg aagggagtca gatttagcga agctcttcga    3300
gctcccaaag attcgaacac taactcgcgc ccgtgggccg atggaggttc tccctactcc    3360
actccttggt cccttaact ggcttncgcc tcctggtcaa tcactgagca accagaatgg    3420
tatcctcgac cagggccaca ggcagtgctc ggcggagtgg ctccaggagt tacccgctcc    3480
ctgccgggct tcgtatccaa accctcccct tcacccctcc tccccaaact gggcgccagg    3540
atgctccggc cggaatatac gcaggctttg ggcgtttgcc caagggtttt cttccctcct    3600
```

-continued

```
aaactagccg ctgttttccc ggcttaaccg tagaagaatt agatattcct cactggaaag    3660
ggaaactaag tgctgctgac tccaatttta ggtaggcggc aaccgccttc cgcctggngn    3720
aaacctcacc aagtaaacaa ctactagccg atcgaaatac gcccggctta taactggtgc    3780
aactcccggc cacccaactg agggacgttc gctttcagtc ccgacctctg gaacccacaa    3840
agggccacct ctttccccag tgaccccaag atcatggcca ctcccctacc cgacagttct    3900
agaagcaaga gccagactca agggtgcaaa gcaagggnat acgcttcttt gaagcttgac    3960
tgagttcttt ctgcgctttc ctgaagttcc cgccctcttg gagcctacct gcccctccct    4020
ccaaaccact cttttagatt aacaacccca tctctactcc caccgcattc gaccctgccc    4080
ggactcactg cttacctgaa cgactctcca gtgagacgag gctcccacac tggcgaaggc    4140
caagaagggg aggtggggg agggttgtgc cacaccggcc agctgagagc gcgtgttggg    4200
ttgaagagga gggtgtctcc gagagggacg ctccctcgga cccgccctca ccccagctgc    4260
gagggcgccc ccaaggagca gcgcgcgctg cctggccggg cttgggctgc tgagtgaatg    4320
gagcggccga gcctcctggc tcctcctctt ccccgcgccg ccggccccctc ttatttgagc    4380 tttgggaagc tgagggcagc caggcagctg gggtaaggag ttcaaggcag cgcccacacc    4440
cgggggctct ccgcaacccg accgcctgtc cgctccccca cttcccgccc tccctcccac    4500
ctactcattc acccacccac ccacccagag ccgggacggc agcccaggcg cccgggcccc    4560
gccgtctcct cgccgcgatc ctggacttcc tcttgctgca ggacccggct tccacgtgtg    4620
tcccggagcc ggcgtctcag cacacgctcc gctccgggcc tgggtgccta cagcagccag    4680
agcagcaggg agtccgggac ccgggcggca tctgggccaa gttaggcgcc gccgaggcca    4740
gcgctgaacg tctccaggc cggaggagcc gcggggcgtc cgggtctgag cctcagcaaa    4800
tgggctccga cgtgcgggac ctgaacgcgc tgctgcccgc cgtcccctcc ctgggtggcg    4860
gcggcggctg tgccctgcct gtgagcgcg cggcgcagtg ggcgccggtg ctggactttg    4920
cgcccccggg cgcttcggct tacgggtcgt tgggcggccc cgcgccgcca ccggctccgc    4980
cgccaccccc gccgccgccg cctcactcct tcatcaaaca ggagccgagc tgggcggcg    5040 cggagccgca cgaggagcag tgcctgagcg ccttcactgt ccactttttcc ggccagttca    5100 ctggcacagc cggagcctgt cgctacgggc ccttcggtcc tcctccgccc agccaggcgt    5160
catccggcca ggccaggatg tttcctaacg cgccctacct gcccagctgc ctcgagagcc    5220
agcccgctat tcgcaatcag ggtaagtagg ccggggagcg cccccctacgc gcggggcagt    5280 ggcgccaggg actctccgct ctaggacacc ccctctcct accccttttg accgcagctc    5340
ttacccagct gcttcccaag ggccgtgagg atagcggaag cggcggctgg ggaggaggcc    5400
ggagagtggg agtgcacgca ggcactggcc cccgacatcc tccaaagcca ggcagagcta    5460
ggagcctgac tgttcgcaag agccgggagg gcgtctgggg ccc                      5503
```

<210> SEQ ID NO 13
<211> LENGTH: 1816
<212> TYPE: DNA
<213> ORGANISM: Homo sapiens
<220> FEATURE:
<221> NAME/KEY: interferon regulatory factor 7B_IRF-7
<222> LOCATION: (1)..(1816)
<223> OTHER INFORMATION: GenBank accession No. U53831

<400> SEQUENCE: 13

```
ggcacccagg gtccggcctg cgccttcccg ccaggcctgg acactggttc aacacctgtg      60
acttcatgtg tgcgcgccgg ccacacctgc agtcacacct gtagccccct ctgccaagag     120
```

-continued

```
atccataccg aggcagcgtc ggtggctaca agccctcagt ccacacctgt ggacacctgt      180
gacacctggc cacacgacct gtggccgcgg cctggcgtct gctgcgacag gagcccttac      240
ctcccctgtt ataacacctg accgccacct aactgcccct gcagaaggag caatggcctt      300
ggctcctgag agggcagccc acgcgtgctg ttcggagag tggctccttg gagagatcag       360
cagcggctgc tatgagggc tgcagtggct ggacgaggcc cgcacctgtt tccgcgtgcc       420
ctggaagcac ttcgcgcgca aggacctgag cgaggccgac gcgcgcatct tcaaggcctg     480
ggctgtggcc cgcggcaggt ggccgcctag cagcagggga ggtggcccgc ccccgaggc      540 tgagactgcg gagcgcgccg gctggaaaac caacttccgc tgcgcactgc gcagcacgcg      600
tcgcttcgtg atgctgcggg ataactcggg ggacccggcc gacccgcaca aggtgtacgc      660
gctcagccgg gagctgtgct ggcgagaagg cccaggcacg gaccagactg aggcagaggc      720
ccccgcagct gtcccaccac acagggtgg ccccccaggg ccattcttgg cacacacaca     780
tgctggactc caagcccccag gccccctccc tgccccagct ggtgacaagg ggacctcct     840 gctccaggca gtgcaacaga gctgcctggc agaccatctg ctgacagcgt catgggggc     900 agatccagtc ccaaccaagg ctcctggaga gggacaagaa gggcttcccc tgactggggc     960
ctgtgctgga ggcgaggccg cggcccagaa gtccccgcac caggcagagc cgtacctgtc    1020
accctcccca agcgcctgca ccgcggtgca agagcccagc ccagggggcgc tggacgtgac    1080 catcatgtac aagggccgca cggtgctgca aaggtggtg ggacacccga gctgcacgtt     1140
cctatacggc cccccagacc cagctgtccg gccacagac cccagcagg tagcattccc      1200 cagccctgcc gagctcccgg accagaagca gctgcgctac acggaggaac tgctgcggca    1260
cgtggcccct gggttgcacc tggagcttcg ggggccacac ctgtgggccc ggcgcatggg    1320
caagtgcaag gtgtactggg aggtgggcgg accccaggc tccgccagcc cctccacccc    1380
agcctgcctg ctgcctcgga actgtgacac ccccatcttc gacttcagag tcttcttcca     1440
agagctggtg gaattccggg cacggcagcg ccgtggctcc ccacgctata ccatctacct    1500
gggcttcggg caggacctgt cagctgggag gcccaaggaa aagagcctgg tcctggtgaa    1560
gctggaaccc tggctgtgcc gagtgcacct agagggcacg cagcgtgagg gtgtgtcttc   1620
cctggatagc agcagcctca gcctctgcct gtccagcgcc aacagcctct atgacgacat    1680
cgagtgcttc cttatggagc tggagcagcc cgcctagaac ccagtctaat gagaactcca    1740
gaaagctgga gcagcccacc tagagctggc cgcggccgcc cagtctaata aaagaactc    1800 cagaacaaaa aaaaaa                                                   1816
```

<210> SEQ ID NO 14
<211> LENGTH: 2056
<212> TYPE: DNA
<213> ORGANISM: Homo sapiens
<220> FEATURE:
<221> NAME/KEY: Interferon-induced 60 kDa protein (CIG49)
<222> LOCATION: (1)..(2056)
<223> OTHER INFORMATION: GenBank accession No. AF026939

<400> SEQUENCE: 14

```
gtggaaacct cttcagcatt tgcttggaat cagtaagcta aaaacaaaat caaccgggac       60
cccagctttt cagaactgca gggaaacagc catcatgagt gaggtcacca agaattccct     120
ggagaaaatc ctcccacagc tgaaatgcca tttcacctgg aacttattca aggaagacag    180
tgtctcaagg gatctagaag atagagtgtg taaccagatt gaattttaa acactgagtt      240
```

```
caaagctaca atgtacaact tgttggccta cataaaacac ctagatggta acaacgaggc    300
agccctggaa tgcttacggc aagctgaaga gttaatccag caagaacatg ctgaccaagc    360
agaaatcaga agtctagtca cttggggaaa ctacgcctgg gtctactatc acttgggcag    420
actctcagat gctcagattt atgtagataa ggtgaaacaa acctgcaaga aattttcaaa    480
tccatacagt attgagtatt ctgaacttga ctgtgaggaa gggtggacac aactgaagtg    540
tggaagaaat gaaagggcga aggtgtgttt tgagaaggct ctggaagaaa agcccaacaa    600
cccagaattc tcctctggac tggcaattgc gatgtaccat ctggataatc acccagagaa    660
acagttctct actgatgttt tgaagcaggc cattgagctg agtcctgata accaatacgt    720
caaggttctc ttgggcctga aactgcagaa gatgaataaa gaagctgaag gagagcagtt    780
tgttgaagaa gccttggaaa agtctccttg ccaaacagat gtcctccgca gtgcagccaa    840
attttacaga agaaaaggtg acctagacaa agctattgaa ctgtttcaac gggtgttgga    900
atccacacca acaatggct acctctatca ccagattggg tgctgctaca aggcaaaagt    960
aagacaaatg cagaatacag gagaatctga agctagtgga aataaagaga tgattgaagc   1020
actaaagcaa tatgctatgg actattcgaa taaagctctt gagaagggac tgaatcctct   1080
gaatgcatac tccgatctcg ctgagttcct ggagacggaa tgttatcaga caccattcaa   1140
taaggaagtc cctgatgctg aaaagcaaca atcccatcag cgctactgca accttcagaa   1200
atataatggg aagtctgaag cactgctgt gcaacatggt ttagagggtt tgtccataag   1260
caaaaaatca actgacaagg aagagatcaa agaccaacca cagaatgtat ccgaaaatct   1320
gcttccacaa aatgcaccaa attattggta tcttcaagga ttaattcata gcagaatgg   1380 agatctgctg caagcagcca aatgttatga gaaggaactg ggccgcctgc taagggatgc   1440
cccttcaggc ataggcagta ttttcctgtc agcatctgag cttgaggatg gtagtgagga   1500
aatgggccag gcgcagtca gctccagtcc cagagagctc ctctctaact cagagcaact   1560
gaactgagac agaggaggaa aacagagcat cagaagcctg cagtggtggt tgtgacgggt   1620
aggaggatag gaagacaggg ggccccaacc tgggattgct gagcagggaa gctttgcatg   1680
ttgctctaag gtacatttt aaagagttgt tttttggccg ggcgcagtgg ctcatgcctg   1740
taatcccagc actttgggag gccgaggtgg gcggatcacg aggtctggag tttgagacca   1800
tcctggctaa cacagtgaaa tcccgtctct actaaaaata caaaaaatta gccaggcgtg   1860
gtggctggca cctgtagtcc cagctacttg ggaggctgag gcaggagaat ggcgtgaacc   1920
tggaaggaag aggttgcagt gagccaagat tgcgccctg cactccagcc tgggcaacag   1980
agcaagactc ggaattcctg cagcccgggg gatccactat tctagagcgc gcaacggcc    2040 gtggagtcca gagatg                                                   2056
```

<210> SEQ ID NO 15
<211> LENGTH: 1879
<212> TYPE: DNA
<213> ORGANISM: Homo sapiens
<220> FEATURE:
<221> NAME/KEY: nuclear autoantigen (SP-100)
<222> LOCATION: (1)..(1879)
<223> OTHER INFORMATION: GenBank accession No. M60618

<400> SEQUENCE: 15

```
ctgaggccca cgcagggcct agggtgggaa gatggcaggt gggggcggcg acctgagcac     60
caggaggctg aatgaatgta tttcaccagt agcaaatgag atgaaccatc ttcctgcaca    120
cagccacgat ttgcaaagga tgttcacgga agaccaggt gtagatgaca ggctgctcta    180
```

```
tgacattgta ttcaagcact tcaaaagaaa taaggtggag atttcaaatg caataaaaaa      240
gacatttcca ttcctcgagg gcctccgtga tcgtgatctc atcacaaata aaatgtttga      300
agattctcaa gattcttgta gaaacctggt ccctgtacag agagtggtgt acaatgttct      360
tagtgaactg gagaagacat ttaacctgcc agttctggaa gcactgttca gcgatgtcaa      420
catgcaggaa tacccccgatt taattcacat ttataaaggc tttgaaaatg taatccatga     480
caaattgcct ctccaagaaa gtgaagaaga agagagggag gagaggtctg gcctccaact      540
aagtcttgaa caaggaactg gtgaaaactc ttttcgaagc ctgacttggc caccttcggg      600
ttccccatct catgctggta caaccccacc tgaaaatgga ctctcagagc accctgtga      660 aacagaacag ataaatgcaa agagaaaaga tacaaccagt gacaaagatg attcgctagg      720
aagccaacaa acaaatgaac aatgtgctca aaaggctgag ccaacagagt cctgcgaaca      780
aattgctgtc caagtgaata atgggggatgc tggaagggaa atgccctgcc cgttgccctg      840
tgatgaagaa agcccagagg cagagctaca caaccatgga atccaaatta attcctgttc      900
tgtgcgactg gtggatataa aaaaggaaaa gccattttct aattcaaaag ttgagtgcca      960
agcccaagca agaactcatc ataaccaggc atctgacata atagtcatca gcagtgagga     1020
ctctgaagga tccactgacg ttgatgagcc cttagaagtc ttcatctcag caccgagaag     1080
tgagcctgtg atcaataatg acaacccttt agaatcaaat gatgaaaagg agggccaaga     1140
agccacttgc tcacgacccc agattgtacc agagcccatg gatttcagaa aattatctac     1200
attcagagaa agttttaaga aaagagtgat aggacaagac cacgactttt cagaatccag     1260
tgaggaggag gcgcccgcag aagcctcaag cggggcactg agaagcaagc atggtgagaa     1320 ggctccctatg acttctagaa gtacatctac ttggagaata cccagcagga agagacgttt     1380
cagcagtagt gacttttcag acctgagtaa tggagaagag cttcaggaaa cctgcagctc     1440
atccctaaga agagggtcag gtaaagaaga ttaggatgcc aagacttggc ctgcagaatg     1500
tcaggaatgt gaattaaaag ctgctgtttc cagacgcttt ttattctgag caccttcact     1560
accttgtatc cagttcatct gggaactcct ttttgcattt tagaaaatgg aaagaggcag     1620
gaaattatga taaactcatg tttaacagaa agagtttcac tgactaaatg tatgtaatta     1680
tattttgttg ttgtagaaga aataaatagc aaatttgtgg tattcttttt tttaaacctg     1740
ctctcattcc tattaacact aagatcttag atttttatag tgataaatgg gttgacatca     1800
ttgtcgtttg taattgtaaa gcctcaaaag acaactgttc ctactatgta attatagaca     1860
gaaataaaaa cttcagatc                                                  1879
```

<210> SEQ ID NO 16
<211> LENGTH: 3997
<212> TYPE: DNA
<213> ORGANISM: Homo sapiens
<220> FEATURE:
<221> NAME/KEY: KIAA0793
<222> LOCATION: (1)..(3997)
<223> OTHER INFORMATION: GenBank accession No. AB018336

<400> SEQUENCE: 16

```
ggcgacgccg acgcgagtct ggcggctgct gcttgcgact gcggaggccg ggcgaggccg       60
gtgaggacgc ggcgggcgag cgagaggccg aggtgttttc ttcactcatg gtgaagaatg      120
ggggagatag aaggaacata cagagtcctg cagactgcag ggatgcgctt gggtgcccag      180
acccctgtgg gagttagcac ccttgagcct gggcagactc tcttgcccag aatgcaagag      240
```

```
aagcacctgc acctcagagt aaagctgctg acaacacaca tggaaatatt tgacattgag     300
cctaaatgcg atggccaggt attactgaca caagtgtgga agcgtttaaa cctggtagaa     360
tgtgactact tcgggatgga gtttcaaaat actcagtcct actggatttg gcttgaacct     420
atgaaaccca tcattaggca aatacgaagg ccaaagaatg tggtgcttcg cctagctgta     480
aaattttttc cacctgatcc tggtcagcta caagaagaat atacaagata cttgtttgcc     540
ttgcaactta agagagacct gctggaagag cgtttgacct gtgctgacac cacagcggcc     600
cttctcacgt cccatctcct gcagtcggaa ataggagatt acgatgaaac gctggaccga     660
gagcacctca aagtgaacga gtatttgcct ggccagcagc actgccttga aagatacta      720 gaattccatc agaagcacgt gggccagaca cctgctgagt cggatttcca ggtgctcgaa     780
attgctcgaa agttggaaat gtacggcatc agatttcaca tggcttctga cagggaagga     840
accaagattc aactggcagt tcccacatg ggtgtactcg tgttccaggg caccaccaaa      900
atcaacactt tcaactggtc caaggtccgt aaactaagct tcaagaggaa aagatttctt     960
atcaaacttc atccagaggt tcatggacct taccaggaca cattagaatt tttgttgggt    1020
agtagagatg aatgtaagaa cttctggaag atttgtgtgg agtatcacac cttttttaga    1080
cttttggacc aacctaagcc aaaagcaaaa gccgtcttct tcagccgggg ctcctccttc    1140
agatacagtg gaagaactca gaaacaacta gtagattatt tcaaagacag tggaatgaag    1200
agaattccat atgaaagaag gcacagcaag acccacacgt ccgttcgagc tctgactgca    1260
gacctaccaa aacagagcat ctcattcccc gagggattga ggactcctgc ctccccatct    1320
tcagcgaatg ccttttactc gctctctccc tccactctgg tcccctctgg cctgccagag    1380
tttaaggaca gcagcagctc cctcacagat ccccaggttt cctacgtcaa gagtccagct    1440
gcagagaggc gcagtggagc agtggctgga ggccccgaca caccatcggc ccagccctc     1500 gggccccccg cactccagcc tggtccagc ctttccacga agagtcctca gccttctccc     1560
tccagccgga agagccccct gagtctgagc cctgcatttc aggtgccttt gggcccagct    1620
gaacagggct catccccact cctgagccct gtcctcagtg atgctggcgg agccgggatg    1680
gactgcgagg agcccagaca caagcgcgtg cctgcagacg aggcctactt catagtcaaa    1740
gagattctcg ctacagaacg aacatacctc aaggatttag aagttattac cgtgtggttc    1800
cgcagcgcag tggtgaagga ggacgccatg cctgcgactc tgatgacgct gctcttctcc    1860
aacatcgatc ccatctatga gttccacaga ggcttcctgc gcgaggtgga gcagaggctg    1920
gcactctggg aagggccctc caaagcccac acaaaaggca gtcatcaacg aatcggggac    1980
atcctgctca ggaacatgcg ccagttaaag gagtttacca gctacttcca aagacatgac    2040
gaggtcctaa cagaactgga aaaggctacc aaacgctgta agaagttgga ggcagtgtac    2100
aaggagtttg agctgcagaa ggtctgctac ttgcctctca cacgttcct gctgaagccc     2160 atccagcggc tgctgcacta ccgcctgctg ctgcgccgcc tatgcggaca ttacagcccc    2220
gggcaccatg actacgctga ctgccatgac gccctgaaag ccatcacaga ggtgaccacc    2280
acactacagc acattctcat ccggctggag aacctgcaga agctaacgga gctgcagcgg    2340
gacctggtgg gcatagagaa cctcattgct cctggcaggg agttcatccg tgagggctgc    2400
cttcacaagc tcaccaagaa gggcctgcag cagaggatgt ttttctgtt ctcagatatg     2460 ttgctgtaca caagcaaagg agttgcaggg accagccact tccggatccg gggcctcctt    2520
cccctccaag gcatgctggt ggaagaaagt gataacgagt ggtctgttcc acactgtttc    2580
accatctacg cggctcagaa acaatcgtg gtggcagcca gcactcggct ggagaaagag     2640
```

-continued

```
aagtggatgc tggacctgaa ctccgcgatc caagcagcca agagtggcgg tgacacggcc    2700
cctgcactgc caggccgcac tgtgtgcact cgtcccccca gatcccccaa cgaggtatct    2760
ctggagcagg agtcagaaga tgatgctcgg ggtgtccgca gctccctgga ggggcatggc    2820
cagcaccggg ccaacaccac aatgcacgtg tgctggtacc ggaacaccag cgtgtccagg    2880
gcagaccaca gtgcagctgt cgagaaccag ctttcaggat atctgctaag aaagttcaaa    2940
aacagtcatg gctggcagaa gctctgggtc gtctttacca acttctgttt gttcttctac    3000
aaaactcatc aggatgacta cccactggcc agcctcccgc tgctgggcta cagcgtgagc    3060
atccccaggg aggccgatgg catacacaaa gactatgttt tcaagctcca gttcaaatcc    3120
cacgtctact tcttccgggc tgagagcaag tacacatttg aaaggtggat ggaggtgatc    3180 caggggggcca gcagctcagc cgggagggcc ccaagcatcg tgcaggatgg cccccaaccc    3240
tcctcagggc tggaggggat ggtcaggggg aaggaggaat gacgctcaac ctgcccaggt    3300
ttggacacaa ctacaaagaa cagcaggaca cagaggtgac ctctgtcctg aggcttctca    3360
acagatggga agtggctgtg gtctcactgg atccccactg gcaccagcag tgtgggtggg    3420
cctcatgtaa catctgggag gggcttcatc cccccaccca ggacctagtg catgccagca    3480
gctatctggg gccctgggaa aaatgtgcga gtcttgagcg cggagccgct caagccacag    3540
ctcccaggcc cctggctcaa agacgcagac aaggcctgag cagtgctctc ggcatcggac    3600
caaagcctgg gcacccctg cctctctccc cagagcaggg tccctgccga ggactggcct    3660
agagcaagca ctggaaaaga ggccctgcca tacaccctgc gtaccactg ccaggaccct     3720 ctcagacaag cgtggcacag ccatgctgac cttccatctg gtgaaccaag tggcagcccc    3780 agggggcctgc cctgcaggtc acagctaaac aagtctggca gaagccacgc ttgttcccca    3840
tgtacctcta gagaagcaga aaccaaagtc cccctgtgcc ctgggagggt ggggccgtct    3900
aatttattac tgcccagcat tccttccaac gggaagtaga tgggcgactg ctttgttcac    3960
acacatttga ttaaaaataa acaaacagca tctcccc                             3997
```

<210> SEQ ID NO 17
<211> LENGTH: 2905
<212> TYPE: DNA
<213> ORGANISM: Homo sapiens
<220> FEATURE:
<221> NAME/KEY: 2'5' oligoadenylate synthetase (p69 2-5A synthetase)
<222> LOCATION: (1)..(2905)
<223> OTHER INFORMATION: GenBank accession No. M87434

<400> SEQUENCE: 17

```
cggcagccag ctgagagcaa tgggaaatgg ggagtcccag ctgtcctcgg tgcctgctca      60
gaagctgggt tggtttatcc aggaatacct gaagccctac gaagaatgtc agacactgat     120
cgacgagatg gtgaacacca tctgtgacgt ctgcaggaac cccgaacagt tccccctggt     180
gcagggagtg gccataggtg gctcctatgg acggaaaaca gtcttaagag gcaactccga     240
tggtaccctt gtccttttct tcagtgactt aaaacaattc caggatcaga agagaagcca     300
acgtgacatc ctcgataaaa ctgggggataa gctgaagttc tgtctgttca cgaagtggtt    360
gaaaaacaat ttcgagatcc agaagtccct tgatgggtcc accatccagg tgttcacaaa    420
aaatcagaga atctctttcg aggtgctggc cgccttcaac gctctgagct taaatgataa    480
tcccagcccc tggatctatc gagagctcaa aagatccttg gataagacaa atgccagtcc    540
tggtgagttt gcagtctgct tcactgaact ccagcagaag ttttttgaca accgtcctgg    600
```

```
aaaactaaag gatttgatcc tcttgataaa gcactggcat caacagtgcc agaaaaaaat    660
caaggattta ccctcgctgt ctccgtatgc cctggagctg cttacggtgt atgcctggga    720 acagggtgc agaaaagaca actttgacat tgctgaaggc gtcagaacgg ttctggagct    780
gatcaaatgc caggagaagc tgtgtatcta ttggatggtc aactacaact ttgaagatga    840
gaccatcagg aacatcctgc tgcaccagct ccaatcagcg aggccagtaa tcttggatcc    900
agttgaccca accaataatg tgagtggaga taaaatatgc tggcaatggc tgaaaaaaga    960
agctcaaacc tggttgactt ctcccaacct ggataatgag ttacctgcac catcttggaa   1020
tgtcctgcct gcaccactct tcacgacccc aggccacctt ctggataagt tcatcaagga   1080
gtttctccag cccaacaaat gcttcctaga gcagattgac agtgctgtta acatcatccg   1140
tacattcctt aaagaaaact gcttccgaca atcaacagcc aagatccaga ttgtccgggg   1200
aggatcaacc gccaaaggca cagctctgaa gactggctct gatgccgatc tcgtcgtgtt   1260
ccataactca cttaaaagct cacctcccca aaaaacgag cggcacaaaa tcgtcaagga   1320
aatccatgaa cagctgaaag ccttttggag ggagaaggag gaggagcttg aagtcagctt   1380
tgagcctccc aagtggaagg ctcccagggt gctgagcttc tctctgaaat ccaaagtcct   1440
caacgaaagt gtcagctttg atgtgcttcc tgcctttaat gcactgggtc agctgagttc   1500
tggctccaca cccagccccg aggtttatgc agggctcatt gatctgtata atcctcgga   1560 cctcccggga ggagagtttt ctacctgttt cacagtcctg cagcgaaact tcattcgctc   1620
ccggcccacc aaactaaagg atttaattcg cctggtgaag cactggtaca agagtgtga   1680 aaggaaactg aagccaaagg ggtctttgcc cccaaagtat gccttggagc tgctcaccat   1740
ctatgcctgg gagcagggga gtggagtgcc ggatttgac actgcagaag gtttccggac   1800
agtcctggag ctggtcacac aatatcagca gctcggcatc ttctggaagg tcaattacaa   1860 cttttgaagat gagaccgtga ggaagttct actgagccag ttgcagaaaa ccaggcctgt   1920
gatcttggac ccaggcgaac ccacaggtga cgtgggtgga ggggaccgtt ggtgttggca   1980
tcttctggac aaagaagcaa aggttaggtt atcctctccc tgcttcaagg atgggactgg   2040
aaacccaata ccaccttgga aagtgccgac aatgcagaca ccaggaagtt gtggagctag   2100
gatccatcct attgtcaatg agatgttctc atccagaagc catagaatcc tgaataataa   2160
ttctaaaaga aacttctgga gatcatctgg caatcgcttt taaagactcg gctcaccgtg   2220
agaaagagtc actcacatcc attcttccct tgatggtccc tattcctcct tcccttgcct   2280
tcttggactt cttgaaatca atcaagactg caaacccttt cataaagctg ccttgctgaa   2340
ctcctctctg caggagccct gcttaaaata gttgatgtca tcactttatg tgcatcttat   2400
ttctgtcaac ttgtattttt ttttcttgta tttttccaat tagctcctcc ttttcccttc   2460
cagtctaaaa aaggaatcct ctgtgtcttc aaagcaaagc tctttacttt cccctttggtt   2520 ctcataactc tgtgatcttg ctctcggtgc ttccaactca tccacgtcct gtctgtttcc   2580
tctgtataca aaacccctttc tgccctgct gacacagaca tcctctatgc cagcagccag   2640
gccaaccctt tcattagaac ttcaagctct ccaaaggctc agattataac tgttgtcata   2700
tttatatgag gctgttgtct tttccttctg agcctgcctt tatcccccca cccaggagta   2760
tcctcttgcc aaagcaaaag acttttttcct tggcttagc cttaaagata cttgaaggtc   2820
taggtgcttt aacctcacat accctcactt aaacttttat cactgttgca tataccagtt   2880
gtgatacaat aaagaatgta tctgg                                         2905
```

<210> SEQ ID NO 18
<211> LENGTH: 840
<212> TYPE: DNA
<213> ORGANISM: Homo sapiens
<220> FEATURE:
<221> NAME/KEY: histone H2A
<222> LOCATION: (1)..(840)
<223> OTHER INFORMATION: GenBank accession No. Z80776

<400> SEQUENCE: 18

```
ggatgaattg tctctgtgtg ccctgtggta tgcaaattag gtgattctag cgtttctttg      60
caattggttg gttgttctag ccaatcaaat agcgttattt acaattcgac ctccaagtat     120
aatagtttct cacttgctaa caaaactcac ttttacattt ttgtcttcat tgcttaacat     180
cgttttaag aattcaaaat gtccggacgc ggcaagcaag gcggaaaggc ccgagctaag      240
gctaagaccc gctcttcgcg ggccggactc cagttccctg tgggccgcgt acaccgcttg     300
ctccgcaagg gcaactactc cgagcgagtc ggggccggcg cgccagtgta tctggcggcg     360
gtgttggagt acctgaccgc cgagatcctg gagctggcgg gcaacgccgc ccgcgacaac     420
aagaagaccc gcatcatccc ccgacacctg cagctggcca tccgcaacga cgaggagcta     480
aacaagttgc tgggtaaagt cacaattgct cagggcggtg ttctgcccaa catccaggct     540
gtactgctcc ccaagaagac tgagagtcac cacaaggcca aggcaagta aaacgagaac      600
tcttatattg gctttttaag gaagcagtct taacaaaggc tcttttcaga gccacccatg     660
tattccttaa aagggctcac attttctgtg taaatagcta ttttgcagtt ttctttaata     720
attttttccat ttataagtgg gtgttcttaa cactgaatcg tgaaactaac cgtccatttt    780
aaagatgcca taaaaataca taagcaaatt ggcggggcgc ggttgcttac gcctgtaatc     840
```

<210> SEQ ID NO 19
<211> LENGTH: 1230
<212> TYPE: DNA
<213> ORGANISM: Homo sapiens
<220> FEATURE:
<221> NAME/KEY: GPR12 G protein coupled-receptor
<222> LOCATION: (1)..(1230)
<223> OTHER INFORMATION: GenBank accession No. U18548

<400> SEQUENCE: 19

```
aagcttgtgg catttggtac tggtatctga gcaggggctg gctttctgtt tgtctgtgtg      60
tttttttgcat gatcttggat tgtcaccctg ctgtatttaa acattaaaaa gcctgtcttt    120
tcgttgaaga ggacaggggt taaaatgaat gaagacctga aggtcaattt aagcgggctg     180
cctcgggatt atttagatgc cgctgctgcg gagaacatct cggctgctgt ctcctcccgg     240
gttcctgccg tagagccaga gcctgagctc gtagtcaacc cctgggacat tgtcttgtgt     300
acctcgggaa ccctcatctc ctgtgaaaat gccattgtgg tccttatcat cttccacaac     360
cccagcctgc gagcacccat gttcctgcta ataggcagcc tggctcttgc agacctgctg     420
gccggcattg gactcatcac caattttgtt tttgcctacc tgcttcagtc agaagccacc     480
aagctggtca cgatcggcct cattgtcgcc tctttctctg cctctgtctg cagcttgctg     540
gctatcactg ttgaccgcta cctctcactg tactacgctc tgacgtacca ttcggagagg     600
acggtcacgt ttacctatgt catgctcgtc atgctctggg ggacctccat ctgcctgggg     660
ctgctgcccg tcatgggctg gaactgcctc cgagacgagt ccacctgcag cgtggtcaga     720
ccgctcacca gaacaacgc ggccatcctc tcggtgtcct tcctcttcat gtttgcgctc     780
atgcttcagc tctacatcca gatctgtaag attgtgatga ggcacgccca tcagatagcc     840
```

-continued

| | |
|---|---|
| ctgcagcacc acttcctggc cacgtcgcac tatgtgacca cccggaaagg ggtctccacc | 900 |
| ctggctatca tcctggggac gtttgctgct tgctggatgc ctttcaccct ctattccttg | 960 |
| atagcggatt acacctaccc ctccatctat acctacgcca ccctcctgcc cgccacctac | 1020 |
| aattccatca tcaaccctgt catatatgct ttcagaaacc aagagatcca gaaagcgctc | 1080 |
| tgtctcattt gctgcggctg catcccgtcc agtctcgccc agagagcgcg ctcgcccagt | 1140 |
| gatgtgtagc acccttgcac ccaggaggac tctgcattta ccaagcactt ccactgcctg | 1200 |
| gccaaggttt gagatgcttc ccttgaattc | 1230 |

<210> SEQ ID NO 20
<211> LENGTH: 5141
<212> TYPE: DNA
<213> ORGANISM: Homo sapiens
<220> FEATURE:
<221> NAME/KEY: steroid 21-hydroxylase (CYP21)
<222> LOCATION: (1)..(5141)
<223> OTHER INFORMATION: GenBank accession No. M12792

<400> SEQUENCE: 20

| | |
|---|---|
| agatctttct cccagtagct gctcagcatg gtggtggcat aagcccattt tccggagcca | 60 |
| gggattcagt tgcagcaaga catggcccgg tctggaggt caaccatgaa gaaggcagta | 120 |
| gctgtcattg cccaaccca gaaatcccaa tcctgttttc tccctctcag tcctgatcat | 180 |
| ggattcagca gcagcgaact cgccaatgta gtgggtggca cagccagggt cttgactctg | 240 |
| gctctgcagt agcacagtct ggaaaagctc tgaggggaga gagaccccca ctggtccgag | 300 |
| ggtctggcac agagccagaa atggggggga aggtatgagg ctgggtcgcc tctgacctct | 360 |
| caggtaccat ccaggaggcc ctggcctctc actgaacccg ccactcctc tttggcatgg | 420 |
| cctcttccca aatccccaaa ctgcctcctt acccacaaaa gtggtctctg agtgtcagtc | 480 |
| cagtgggacc cccacccctt atggcttcag ttccccaaat agggctggac ccttgatcct | 540 |
| gatccagctg tggctatcca gccccttcct ggggactttg actttgagg ggggcatgcc | 600 |
| acttgtgctg ggaatccata ctttccctgg ctggagtaga acctgtggac tgtagtcctg | 660 |
| agggcagtca tgttctgcct gtgcctggaa agacaagaaa cttgactgca gagagaagaa | 720 |
| agaggagaga ggaacagagc gaggaaaccg cccgtctccg gggcttttc tgttccctat | 780 |
| ccttgacttt ctaagaccag tggggtcccc tcctctgctt ctttttcctg agttctgtga | 840 |
| aattccccaa ttcttatttt ttatctcaaa ccagctcaag gtgggctgtt ttccttcaa | 900 |
| ccaaagaaag gtgctcctgg tggctaaagg tacatattcg acagctagat ttccaggctg | 960 |
| gaatcctgcc ctccacaaca tgcgaacaat accgtgttg catatagagc atggctgtga | 1020 |
| agagttgagt gagtgcccac aaagcactta gagcagtgtc tggtacatgc tattactccg | 1080 |
| cagcgggaaa ccacttcctc ctttgtcttc tgggcacttt tgtgagtgaa aggaggcact | 1140 |
| aataacaatc acactgggat acctgtatat actggaatgc cccaggcaaa ccaggcttaa | 1200 |
| actgtattac tctatctgta gcttaaacta acaaacaacc cacacaaatc acattttgtt | 1260 |
| cttcaggcga ttcaggaagg cctattaggc agggactgcc atttctctc tgagacaaac | 1320 |
| atcattccat aaactggccc acggtgggtg gcagagggag agggcccagg tggggcgga | 1380 |
| cactattgcc tgcacagtga tgtggaacca gaaagctgac tctggatgca ggaaaaaggt | 1440 |
| cagggttgca tttcccttcc ttgcttcttg atgggtgatc aattttttg aaatacggac | 1500 |
| gtcccaaggc caatgagact ggtgtcattc cagaaaaggg ccactctgtg ggcgggtcgg | 1560 |
| tgggagggta cctgaaggtg gggtcaaggg aggcccccaaa acagtctaca cagcaggagg | 1620 |

-continued

```
gatggctggg gctcttgagc tataagtggc acctcagggc cctgacgggc gtctcgccat      1680
gctgctcctg ggcctgctgc tgctgcccct gctggctggc gcccgcctgc tgtggaactg      1740
gtggaagctc cggagcctcc acctcccgcc tcttgccccg ggcttcttgc acttgctgca      1800
gcccgacctc ccaatctatc tgcttggcct gactcagaaa ttcgggccca tctacaggct      1860
ccaccttggg ctgcaaggtg agaggctgat ctcgctctgg ccctcaccat aggaggggc       1920 ggaggtgacg gagagggtcc tctctccgct gacgctgctt tggctgtctc ccagatgtgg      1980
tggtgctgaa ctccaagagg accattgagg aagccatggt caaaaagtgg gcagactttg      2040
ctggcagacc tgagccactt acctgtaagg ctgggggca ttttttcttt cttaaacaaa       2100
ttttttttta agagatgggt tcttgctatg ttgcccaggc tggtcttaaa ttcctagtct      2160
caaatgatcc tcccacctca gcctcaagtg tgagccacct ttgggcatc cccaatccag       2220 gtccctggaa gctcttgggg ggcatatctg tggggagaa agcaggggtt ggggaggccg       2280
aagaaggtca ggccctcagc tgccttcatc agttcccacc ctccagcccc cacctcctcc      2340
tgcagacaag ctggtgtcta agaactaccg ggacctgtcc ttgggagact actccctgct      2400
ctggaaagcc cacaagaagc tcacccgctc agccctgctg ctgggcatcc gtgactccat      2460
ggagccagtg gtggagcagc tgacccagga gttctgtgag gtaaggctgg gctcctgagg      2520
ccacctcggg tcagcctcgc ctctcacagt agcccccgcc ctgccgctgc acagcggcct      2580
gctgaactca cactgtttct ccacagcgca tgagagccca gcccggcacc cctgtggcca      2640
ttgaggagga attctctctc ctcacctgca gcatcatctg ttacctcacc ttcggagaca      2700
agatcaaggt gcctcacagc ccctcaggcc caccccagc ccctccctga gcctctcctt       2760
gtcctgaact gaaagtactc cctccttttc tggcaggacg acaacttaat gcctgcctat      2820
tacaaatgta tccaggaggt gttaaaaacc tggagccact ggtccatcca aattgtggac      2880
gtgattccct ttctcagggt gaggacctgg agcctagaca cccctgggtt gtaggggaga      2940
ggctggggtg gagggagagg ctccttccca cagctgcatt ctcatgcttc ctgccgcagt      3000
tcttccccaa tccaggtctc cggaggctga agcaggccat agagaagagg gatcacatcg      3060
tggagatgca gctgaggcag cacaaggtgg ggactgtacg tggacggcct ccctcggcc       3120 cacagccagt gatgctaccg gcctcagcat tgctatgagg cgggttcttt tgcatacccc      3180
agttatgggc ctgttgccac tctgtactcc tctccccagg ccagccgctc agcccgctcc      3240
tttcaccctc tgcaggagag cctcgtggca ggccagtgga gggacatgat ggactacatg      3300
ctccaagggg tggcgcagcc gagcatggaa gagggctctg acagctcct ggaagggcac       3360 gtgcacatgg ctgcagtgga cctcctgatc ggtggcactg agaccacagc aaacaccctc      3420
tcctgggccg tggttttttt gcttcaccac cctgaggtgc gtcctgggga caagcaaaag      3480
gctccttccc agcaacctgg ccagggcggt gggcaccctc actcagctct gagcactgtg      3540
cggctggggc tgtgcttgcc tcaccggcac tcaggctcac tgggttgctg agggagcggc      3600
tggaggctgg gcagctgtgg gctgctgggg caggactcca cccgatcatt ccccagattc      3660
agcagcgact gcaggaggag ctagaccacg aactgggccc tggtgcctcc agctcccggg      3720 tccccctacaa ggaccgtgca cggctgccct tgctcaatgc caccatcgcc gaggtgctgc     3780
gcctgcggcc cgttgtgccc ttagccttgc cccaccgcac cacacggccc agcaggtgac     3840
tcccgagggt tggggatgag tgaggaaagc ccgagcccag ggaggtcctg gccagcctct     3900
aactccagcc cccttcagca tctccggcta cgacatccct gagggcacag tcatcattcc     3960
```

-continued

```
gaacctccaa ggcgcccacc tggatgagac ggtctgggag aggccacatg agttctggcc      4020
tggtatgtgg gggccggggg cctgccgtca aatgtggtg gaggctggtc cccgctgccg       4080
ctgaacgcct ccccacccac ctgtccaccc gcccgcagat cgcttcctgg agccaggcaa      4140
gaactccaga gctctggcct tcggctgcgg tgccccggtg tgcctgggcg agccgctggc      4200
gcgcctggac ctcttcgtgg tgctgacccg actgctgcag gccttcacgc tgctgccctc      4260
cggggacgcc ctgccctccc tgcagcccct gccccactgc agtgtcatcc tcaagatgca      4320
gcctttccaa gtgcggctgc agccccgggg gatgggggcc cacagcccag gccagaacca      4380
gtgatggggc aggaccgatg ccagccgggt acctcagttt ctcctttatt gctcccgtac      4440
gaacccctcc cctcccccct gtaaacacag tgctgcgaga tcgctggcag agaaggcttc      4500
ctccagcggc tgggtggtga aggaccctgg ctcttctctc ggggcgaccc ctcagtgctc      4560
ggcagtcata ctggggtgcg agagaggtgg gcagcagctc agcctccccc cgctggggag      4620
cgaaagtttc ttggtctcag cttcatttcc gtgaagggca ccgagaactc gaagcccttc      4680
cagtggtacc agctcactcc ctgggaaagg ggttgtcaag agagagtcaa agccggatgt      4740
cccatctgct cttcccgttc cccttaagga ggtagctccc agcactcaac caacctcccc      4800
gcagagctcc cttcctgacc ctccgctgca gaggattgag gcttaattct gagctggccc      4860
tttccagcca ataaatcaac tccagctccc tctgcgaggc tggcatgatt gttccatttc      4920
acccagccgc tcagtccctt gcctgttaca ctgtggggct gaaacctagg caggccgagc      4980
cccagccacc ccagctctga gccggcctcc ccaccccctca cctgatggtc cactgtgctc      5040
ccgtagagcc cgttgaggtt ggcgtagtgg cagttcctgt accaccaggc ccctcggtag      5100
gagacagcgc aggagatgag caagctgttg gggtcccgat c                         5141
```

<210> SEQ ID NO 21
<211> LENGTH: 1117
<212> TYPE: DNA
<213> ORGANISM: Homo sapiens
<220> FEATURE:
<221> NAME/KEY: putative tumor suppressor protein (101F6)
<222> LOCATION: (1)..(1117)
<223> OTHER INFORMATION: GenBank accession No. AF040704

<400> SEQUENCE: 21

```
tccggaagta aagcggctcc gtgacggagc ggcggtgcgc gcggcagggc ccggagtatc       60
ccgctttctt tggaggaaac caccgcatca gatctgcgct gcggcagagg caggctacaa      120
ccactagcac ggctgacgat ggccctttct gcggagaccg agtcacacat ctaccgagct      180
ctgcgtactg cttctggcgc tgccgcccac cttgtggccc tgggctttac catctttgtg      240
gctgtgcttg ccaggcctgg ctccagcctg ttctcctggc acccgtgct tatgtctttg      300 gctttctcct tcctgatgac cgaggcacta ctggtgtttt ctcctgagag ttcgctgctg      360
cactccctct cacggaaagg ccgagcacgc tgccactggg tgctgcagct gctggccctg      420
ctgtgtgcac tgctgggcct cggccttgtc atcctccaca agagcagct tggcaaagcc       480 cacctggtta cgcggcatgg gcaggcaggg ctgctggctg tgctgtgggc agggctgcag      540
tgctcaggtg gggtggggct gctctacccc aagctgctgc ccgatggcc cctggcgaag      600 ctcaagctat accatgctac ttctgggctg gtgggctacc tgctgggtag tgccagcctc      660
ttgctgggca tgtgctcact ctggttcact gcctctgtca ctggtgcagc tggtacctg      720 gctgtattat gccctgtcct caccagcttg gtcattatga accaggtgag caatgcctac      780
ctataccgca agaggatcca accatgagct cttcccagcc taggggaagc ctggatttgc      840
```

```
ccctccatgt aggagctggg cctagggacc tgttgaactc tctcagctga gtcagggggac    900
acctcaggca ctgggacagt tgggcatttg gaggcccgtg tgtgaattcc tgctcctcat    960
gctggagtgc ctcccatttc cttcccctttc tctgtcatc ccagaggaac ataggcatca   1020
tgtgtctgga tgaagctggg gctgcaagac tgcctctcct gcaaggcagc tcatacttgt   1080
actgtatgtt cagaaatttt aggagagaaa aaagtaa                             1117
```

<210> SEQ ID NO 22
<211> LENGTH: 4396
<212> TYPE: DNA
<213> ORGANISM: Homo sapiens
<220> FEATURE:
<221> NAME/KEY: transcription factor E2A
<222> LOCATION: (1)..(4396)
<223> OTHER INFORMATION: GenBank accession No. M31523

<400> SEQUENCE: 22

```
gcctgaggtg cccgccctgg ccccaggaga atgaaccagc cgcagaggat ggcgcctgtg     60
ggcacagaca aggagctcag tgacctcctg gacttcagca tgatgttccc gctgcctgtc    120
accaacggga agggccggcc cgcctccctg gccggggcgc agttcggagg ttcaggtctt    180
gaggaccggc ccagctcagg ctcctggggc agcggcgacc agagcagctc ctcctttgac    240
cccagccgga ccttcagcga gggcacccac ttcactgagt cgcacagcag cctctcttca    300
tccacattcc tgggaccggg actcggaggc aagagcggtg agcggggcgc ctatgcctcc    360
ttcgggagag acgcaggcgt gggcggcctg actcaggctg gcttcctgtc aggcgagctg    420
gccctcaaca gccccgggcc cctgtcccct tcgggcatga agggacctc ccagtactac    480
ccctcctact ccggcagctc ccggcggaga gcggcagacg gcagcctaga cacgcagccc    540
aagaaggtcc ggaaggtccc gccgggtctt ccatcctcgg tgtacccacc cagctcaggt    600
gaggactacg gcagggatgc caccgcctac ccgtccgcca agaccccag cagcacctat    660
cccgcccct tctacgtggc agatggcagc ctgcacccct cagccgagct ctggagtccc    720
ccgggccagg cgggcttcgg gcccatgctg gtgggggct catccccgct gcccctcccg    780
cccggtagcg gcccggtggg cagcagtgga agcagcagca cgtttggtgg cctgcaccag    840
cacgagcgta tgggctacca gctgcatgga gcagaggtga acgtgggct cccatctgca    900
tcctccttct cctcagcccc cggagccacg tacgcggcg tctccagcca cacgccgcct    960
gtcagcgggg ccgacagcct cctgggctcc gagggacca cagctggcag ctccggggat   1020
gccctcggca aagcactggc ctcgatctac tccccggatc actcaagcaa taacttctcg   1080
tccagccctt ctacccccgt gggctccccc caggcctgg caggaacgtc acagtggcct   1140
cgagcaggag ccccgggtgc cttatcgccc agctacgacg gggtctccca cggcctgcag   1200
agtaagatag aagaccacct ggacgaggcc atccacgtgc tccgcagcca cgccgtgggc   1260
acagccggcg acatgcacac gctgctgcct ggccacgggg cgctggcctc aggttcacc   1320
ggccccatgt cgctgggtgg gcggcacgca ggctggttg aggcagcca ccccgaggac   1380
ggcctcgcag gcagcaccag cctcatgcac aaccacgcgg ccctccccag ccagccaggc   1440
accctccctg acctgtctcg gcctcccgac tcctacagtg gctagggcg agcaggtgcc   1500
acggcggccg ccagcgagat caagcggag gagaaggag acgaggagaa cgtcagcg   1560
gctgaccact cggaggagga gaagaaggag ctgaaggccc ccggccccg gaccagccca   1620
gacgaggacg aggacgacct tctccccca gagcagaagg ccgagcggga gaaggagcgc   1680
```

-continued

```
cgggtggcca ataacgcccg ggagcggctg cgggtccgtg acatcaacga ggcctttaag      1740
gagctggggc gcatgtgcca actgcacctc aacagcgaga agccccagac caaactgctc      1800
atcctgcacc aggctgtctc ggtcatcctg aacttggagc agcaagtgcg agagcggaac      1860
ctgaatccca aagcagcctg tttgaaacgg cgagaagagg aaaaggtgtc aggtgtggtt      1920 ggagacccccc agatggtgct ttcagctccc cacccaggcc tgagcgaagc ccacaaccccc    1980 gccgggcaca tgtgaaaggt atgcctccgt gggacgagcc acccgctttc agccctgtgc      2040
tctggcccca aagccggac tcgagacccc gggcttcatc cacatccaca cctcacacac      2100
ctgttgtcag catcgagcca acaccaacct gacaaggttc ggagtgatgg gggcggccaa     2160
ggtgacactg ggtccaggag ctccctgggg ccctggccta ccactcactg gcctcgctcc      2220
ccctgtcccc gaatctcagc caccgtgtca ctctgtgacc tgtcccatgg atcctgaaac      2280
tgcatcttgg ccctgttgcc tgggctgaca ggagcatttt ttttttttcc agtaaacaaa      2340
acctgaaagc aagcaacaaa acatacactt tgtcagagaa gaaaaaaatg ccttaactat      2400
aaaaagcgga gaaatggaaa catatcactc aaggggggatg ctgtggaaac ctggcttatt    2460
cttctaaagc caccagcaaa ttgtgcctaa gcgaaatatt tttttttaagg aaaataaaaa     2520 cattagttac aagatttttt ttttcttaag gtagatgaaa attagcaagg atgctgcctt      2580
tggtctctgg tttttttaag cttttttttgc atatgtttttg taagcaacaa atttttttgt   2640
ataaaagtcc cgtgtctctc gctatttctg ctgctgttcc tagactgagc attgcatttc     2700
ttgatcaacc agatgattaa acgttgtatt aaaaagaccc cgtgtaaacc tgagcccccc     2760
ccgtcccccc ccccggaagc cactgcacac agacagacgg ggacaggcgg cgggtctttt    2820 gttttttttga tgttgggggt tctcttggtt ttgtcatgtg gaaagtgatg cgtgggcgtt    2880
ccctgatgaa ggcaccttgg ggcttccctg ccgcatcctc tccctcagg aagggactg       2940 acctgggctt gggggaaggg acgtcagcaa ggtggctctg accctcccag gtgactctgc     3000
caagcagctg tggccccagc ggtaccctac acaacgcccct cccaggcccc ccctaagctg    3060
ctctcccttg gaacctgcac agctctctga aatggggcat tttgttggga ccagtgacccc    3120 ctggcatggg gaccacaccc tggagcccgg tgctggggac ctcctggaca ccctgtcctt     3180
cactccttgc cccagggacc caggctcatg ctctgaactc tggctgagag gagtctgctc     3240
aggagccagc acaggacacc ccccacccca cccccaccatg tccccattac accagagggc    3300
catcgtgacg tagacaggat gccaggggcc tgaccagcct cccccaatgct ggggagcatc    3360 cctggcctgg ggccacacct gctgccctcc ctctgtgtgg tccaagggca agagtggctg    3420
gagccggggg actgtgctgg tctgagcccc acgaaggcct tgggctgtgg ctccgaccct    3480
gctgcagaac cagcagggtg tccccctcggg cccatctgtg tcccatgtcc cagcacccag    3540
gcctctctcc aggtctccctt ttctggtctt ttgccatgag ggtaaccagc tcttcccagc    3600
tggctgggac tgtcttgggt ttaaaactgc aagtctccta ccctgggatc ccatccagtt     3660
ccacacgaac tagggcagtg gtcactgtgg cacccaggtg tgggcctggc tagctggggg    3720
ccttcatgtg cccttcatgc ccctccctgc attgaggcct tgtggacccc tgggctggct    3780
gtgttcatcc ccgctgcagg tcgggcgtct ccccccgtgc cactcctgag actccaccgt    3840
tacccccagg agatcctgga ctgcctgact cccctcccca gactggcttg ggagcctggg   3900
ccccatggta gatgcaaggg aaacctcaag gccagctcaa tgcctggtat ctgccccag     3960 tccaggccag gcgagggga ggggctgtcc ggctgcctct cccttctcgg tggcttcccc     4020
tgcgccctgg gagtttgatc tcttaaggga acttgcctct ccctcttgtt ttgctcctgc    4080
```

-continued

| | |
|---|---|
| cctgcccta ggtctgggtg gcagtggccc catagcctct ggaactgtgc gttctgcata | 4140 |
| gaattcaaac gagattcacc cagcgcgagg aggaagaaac agcagttcct gggaaccaca | 4200 |
| attatggggg gtgggggggtg tgatctgagt gcctcaagat ggttttcaaa aaatttttt | 4260 |
| taaagaaaat aattgtatac gtgtcaacac agctggctgg atgattggga ctttaaaacg | 4320 |
| accctctttc aggtggattc agagacctgt cctgtatata acagcactgt agcaataaac | 4380 |
| gtgacatttt ataaag | 4396 |

<210> SEQ ID NO 23
<211> LENGTH: 4133
<212> TYPE: DNA
<213> ORGANISM: Homo sapiens
<220> FEATURE:
<221> NAME/KEY: KIAA0691
<222> LOCATION: (1)..(4133)
<223> OTHER INFORMATION: GenBank accession No. AB014591

<400> SEQUENCE: 23

| | |
|---|---|
| aaattctccc tgggggtaag gtaccagccc tgtcctttat gggcttcttg ttctaaagca | 60 |
| tatccgtccc atatggttgc tgctagtcac atgtggtgat tagtaactag ttaaaaatga | 120 |
| aaaattcagt tcctccatta cacttgccac atttcagatg ttcagtggcc aacagatatg | 180 |
| cgcaaataga gtgtttccag cattgcaaag ttctgttgga tagcactgtt tgccagatgt | 240 |
| tcccttcttt gtgggtgagg actcttttgg tgtgacttcc ctctgtattg aggctcttgt | 300 |
| tcctcagtat ggggctgttt ctgtctttac agtaagtgac tactccaggg ttccctgccc | 360 |
| tgcacacgta gagtgggagc ggcccgtgga tcccagggaa ctgtgctttt cattgtaggc | 420 |
| cccctccctg gaggggaaga gggcaatctc cgctggtatc tcagaagtct tcttctgagg | 480 |
| cataagcctc tcttcccagg gctcccctgg tctcgctgtc aggccctaag gtatgtcttc | 540 |
| ccttggacta aagctccttg gaactccctt ttgacctcag tcttctctgg gttccaggta | 600 |
| acttccttta aaataaagac gctcctctct tgaagttttg ggttcctgcc ctgatggtct | 660 |
| atgtctccct gactctaaat taccaatcca cttgctatgg gattcctcca tgagtgcaga | 720 |
| ttggctccct cacagctgcg gtaccttttgc accctcttat cttagtaaga tttctgtctt | 780 |
| ctcccaggtc tctcttgggt actgccttct gcccccaaat ctctaagcct tcttggtatt | 840 |
| agcttctttg ggttaggagt gttatttcct tttggtttaa ggatcctgct ctggaataaa | 900 |
| tgtcttggtg gtttgagtcc cttctacttg gcattcagcc ctgtctgcat gagcgggttc | 960 |
| agctcttcac agctttcggc atctctgctc gccgtcgttt tcccccaccc ccaatctttc | 1020 |
| ttctcctacc tacagcttac acacacacac acacacacac acacacacac acgcccttct | 1080 |
| ctgtgagctg ccagtttcat ttgtctcctg acttgtctga gggatgacct ctcctagcca | 1140 |
| cctctgccca gccctctga gtaggaagtg tgatttccag ggctaatgcc tccatcccag | 1200 |
| tcatcagctg tgtgcagcat gactgtcctg ctctgaaaaa cctttttgag tgtattctgg | 1260 |
| gggaaggtac tccatgctct aggaatttt cacttcctga gtcagaggca cacaaaaaag | 1320 |
| tatgtaactt ttcttgtttc aacaaactta tggggtcccc tgttggccag acactatgct | 1380 |
| gggcagtcaa gcgagcatca ggagaactgg ggctggtctc ttgtcagata gcaaatgctt | 1440 |
| cttctctttta ccagtcccac ctacctcact atgctgacta ggtccatgtc tctgggtttt | 1500 |
| taccagccag ggaatacgtg ttaattcctc tccaatctct cctagcagcg tccgtctcca | 1560 |
| agagagtatg aagagagtgc gtctgtaggg cagggaagat ggcggacaag cgcaaactcc | 1620 |

```
aaggtgagat tgatcgctgc ctcaagaagg tgtccgaggg cgtggagcag tttgaagata    1680
tttggcagaa gctccacaat gcagccaacg cgaaccagaa agaaaagtat gaggctgacc    1740
taaagaagga gattaagaag ctacaacggc tgagggacca aatcaagaca tgggtagcgt    1800
ccaacgagat caaggacaag aggcagctta tagacaaccg caagctcatt gagacgcaaa    1860
tggaacggtt caaagttgtg gaacgagaga ccaaaaccaa agcttacagc aaagagggcc    1920
tgggcctggc ccagaaggta gatcctgccc agaaggagaa ggaagaggtt ggccagtggc    1980
tcacgaatac catcgacacg ctcaacatgc aggtggacca gtttgagagt gaagtggagt    2040
cactgtcagt gcagacacgc aagaagaagg gcgacaagga taagcaggac cggattgagg    2100
gcttgaagcg gcacatcgag aagcaccgct accacgtgcg catgctagag accatcctgc    2160
gcatgctgga caatgactcc atcctcgttg acgccatccg caagatcaag gacgacgttg    2220
agtactatgt tgactcatcc caggaccccg acttcgagga gaacgagttt ctctacgatg    2280
acctggacct cgaggacatt ccacaggcgc tggtcgccac ctccccccc agccacagcc    2340 acatggagga tgagatcttc aaccagtcca gcagcacgcc cacctcaacc acctccagct    2400
ctcccatccc gcccagccca gccaactgta ccacggaaaa ctctgaagat gataagaaga    2460
ggggacgttc cacagacagt gaagtcagcc agtctccagc caaaaacggc tccaagcctg    2520
tccacagcaa ccagcaccct cagtcccag ctgtgccgcc cacctacccc tccggccccc    2580
cgcctgctgc ctctgccttg agcaccactc ctggcaacaa tggggtcccc gcccccgcag    2640
cacccccaag tgccctgggc cccaaggcca gtccagctcc cagccacaac tcgggcaccc    2700
ctgctcccta tgcccaggct gtggccccac cagctcccag tgggcccagc acgacccagc    2760
cccggccccc cagcgtccag cctagcggag gcggaggcgg cggcagcgga ggcggaggga    2820
gcagcagcag tagtaacagc agtgccggtg gagggctgg caagcagaat ggcgccacca    2880
gttacagctc agttgtggca gacagcccgg cagaggtggc tttgagcagc agtgggggca    2940
acaatgccag cagccaggcc ttgggccccc cttccggccc ccacaaccca cctcccagca    3000
cctcgaagga acccagtgcg gcagcccaa cggggggctgg gggcgtggcc ccaggctcag    3060
ggaacaactc aggggaccc agcctcctgg tgccactgcc tgtgaatcct cccagctccc    3120
caacgcccag cttcagtgat gccaaggcag ccggtgccct gctcaatggg cctccacagt    3180
tcagcaccgc cccagaaatc aaggcccctg agcctctgag ctccttgaag tccatggcgg    3240
aacgggcagc catcagctct ggcattgagg accctgtgcc aacgctgcac ctgaccgagc    3300
gagacatcat cctgagcagt acatcagcac ctccggcctc agcccagccg cccctgcagc    3360
tgtcagaggt gaacataccg ctgtcgctgg gtgtctgtcc actgggccct gtgccctca    3420 ccaaggagca gctctatcag caggccatgg aagaggccgc ctggcaccac atgcctcacc    3480
cctctgactc tgagcgtatt cggcagtacc tccccccggaa cccctgtccg acgcccccct    3540
accaccacca gatgccaccc ccacactcgg acactgtgga attctaccag cgcctgtcga    3600
ccgagacact cttcttcatc ttctactatc tggagggcac taaggcacag tatctggcag    3660 ccaaggcccct aaagaagcag tcatggcgat ccacaccaa gtacatgatg tggttccaga    3720
ggcacgagga gcccaagacc atcactgacg agtttgagca gggcacctac atctactttg    3780
actacgagaa gtggggccag cggaagaagg aaggcttcac cttgagtac cgctacctgg    3840 aggaccggga cctccagtga caccggcccc tccctctacc cacccccttc cccgcatgc    3900 tgatccccct gcccaggtga gggccctgcc ctggaagact ggaggagggc cccaagccac    3960
ggggcatccc cctctcccag gaagcaggga ggggccgggg aggttttcct ctcagcccca    4020
```

```
cctgggggc cggggcgcga gggctgcccc ctcctcccct ccccagtgag ggacattttt    4080
tggtaaacct attttcattt tggaaaatat ttatgaataa atagttttat atg          4133
```

<210> SEQ ID NO 24
<211> LENGTH: 1260
<212> TYPE: DNA
<213> ORGANISM: Homo sapiens
<220> FEATURE:
<221> NAME/KEY: serotonin 1D receptor 5-HT1D
<222> LOCATION: (1)..(1260)
<223> OTHER INFORMATION: Genank accession No. M81590

<400> SEQUENCE: 24

```
ccctctcctt cgtccgctcc atgcccaaga gctgcgctcc ggagctgggg cgaggagagc    60
catggaggaa ccgggtgctc agtgcgctcc accgccgccc gcgggctccg agacctgggt   120
tcctcaagcc aacttatcct ctgctccctc ccaaaactgc agcgccaagg actacattta   180
ccaggactcc atctccctac cctggaaagt actgctggtt atgctattgg cgctcatcac   240
cttggccacc acgtctctcca atgcctttgt gattgccaca gtgtaccgga cccggaaact   300 gcacacccg gctaactacc tgatcgcctc tctggcagtc accgacctgc ttgtgtccat   360
cctggtgatg cccatcagca ccatgtacac tgtcaccggc cgctggacac tgggccaggt   420
ggtctgtgac ttctggctgt cgtcggacat cacttgttgc actgcctcca tcctgcacct   480
ctgtgtcatc gccctggacc gctactgggc catcacggac gccgtggagt actcagctaa   540
aaggactccc aagagggcgg cggtcatgat cgcgctggtg tgggtcttct ccatctctat   600
ctcgctgccg cccttcttct ggcgtcaggc taaggccgaa aggaggtgt cggaatgcgt   660 ggtgaacacc gaccacatcc tctacacggt ctactccacg gtgggtgctt tctacttccc   720
caccctgctc ctcatcgccc tctatggccg catctacgta aagcccgct cccggatttt   780 gaaacagacg cccaacagga ccggcaagcg cttgaccccga gcccagctga taaccgactc   840
ccccgggtcc acgtcctcgg tcacctctat taactcgcgg gttccgacg tgcccagcga   900 atccggatct cctgtgtatg tgaaccaagt caaagtgcga gtctccgacg ccctgctgga   960
aaagaagaaa ctcatggccg ctagggagcg caaagccacc aagaccctag ggatcatttt  1020
gggagccttt attgtgtgtt ggctacccctt cttcatcatc tccctagtga tgcctatctg  1080
caaagatgcc tgctggttcc acctagccat ctttgacttc ttcacatggc tgggctatct  1140
caactccctc atcaacccca taatctatac catgtccaat gaggacttta aacaagcatt  1200
ccataaactg atacgttta agtgcacaag ttgacttgcc gtttgcagtg gggtcgccta  1260
```

<210> SEQ ID NO 25
<211> LENGTH: 1990
<212> TYPE: DNA
<213> ORGANISM: Homo sapiens
<220> FEATURE:
<221> NAME/KEY: coagulation factor XII (Hageman factor)
<222> LOCATION: (1)..(1990)
<223> OTHER INFORMATION: GenBank accession No. M31315

<400> SEQUENCE: 25

```
ctgctgctcc tggggttcct gctggtgagc ttggagtcaa cactttcgat tccaccttgg    60
gaagccccca aggagcataa gtacaaagct gaagagcaca cagtcgttct cactgtcacc   120 ggggagcct gccacttccc cttccagtac caccggcagc tgtaccacaa atgtacccac   180
aagggccgcc aggccctca gcctggtgt gctaccaccc caactttga tcaggaccag   240
```

-continued

```
cgatggggat actgtttgga gcccaagaaa gtgaaagacc actgcagcaa acacagcccc      300
tgccagaaag gagggacctg tgtgaacatg ccaagcggcc cccactgtct ctgtccacaa      360
cacctcactg gaaaccactg ccagaaagag aagtgctttg agcctcagct tctccggttt      420
ttccacaaga atgagatatg gtatagaact gagcaagcag ctgtggccag atgccagtgc      480
aagggtcctg atgccactg ccagcggctg ccagccagg cctgccgcac caacccgtgc        540
ctccatgggg gtcgctgcct agaggtggag ggccaccgcc tgtgccactg cccggtgggc      600
tacaccggac ccttctgcga cgtggacacc aaggcaagct gctatgatgg ccgcgggctc      660
agctaccgcg gcctggccag gaccacgctc tcgggtgcgc cctgtcagcc gtgggcctcg      720
gaggccacct accggaacgt gactgccgag caagcgcgga actggggact gggcggccac      780
gccttctgcc ggaacccgga caacgacatc cgcccgtggt gcttcgtgct gaaccgcgac      840
cggctgagct gggagtactg cgacctggca cagtgccaga ccccaaccca ggcggcgcct      900 ccgacccegg tgtcccctag gcttcatgtc ccactcatgc ccgcgcagcc ggcaccgccg      960
aagcctcagc ccacgacccg accccgcct cagtcccaga cccgggagc cttgccggcg       1020 aagcgggagc agccgccttc cctgaccagg aacggcccac tgagctgcgg gcagcggctc      1080
cgcaagagtc tgtcttcgat gacccgcgtc gttggcgggc tggtggcgct acgcggggcg      1140 caccctaca tcgccgcgct gtactgggc cacagtttct cgccggcag cctcatcgcc         1200 ccctgctggg tgctgacggc cgctcactgc ctgcaggacc ggcccgcacc cgaggatctg      1260
acggtggtgc tcggccagga acgccgtaac cacagctgtg agccgtgcca gacgttggcc      1320
gtgcgctcct accgcttgca cgaggccttc tcgcccgtca gctaccagca cgacctggct      1380
ctgttgcgcc ttcaggagga tgcggacggc agctgcgcgc tcctgtcgcc ttacgttcag      1440
ccggtgtgcc tgccaagcgg cgccgcgcga ccctccgaga ccacgctctg ccaggtggcc      1500
ggctggggcc accagttcga gggggcggag gaatatgcca gcttcctgca ggaggcgcag      1560
gtaccgttcc tctccctgga gcgctgctca gccccggacg tgcacggatc ctccatcctc      1620
cccggcatgc tctgcgcagg gttcctcgag ggcggcaccg atgcgtgcca gggtgattcc      1680
ggaggcccgc tggtgtgtga ggaccaagct gcagagcgcc ggctcaccct gcaaggcatc      1740
atcagctggg gatcgggctg tggtgaccgc aacaagccag cgtctacac cgatgtggcc       1800 tactacctgg cctggatccg ggagcacacc gtttcctgat tgctcaggga ctcatctttc      1860
cctccttggt gattccgcag tgagagagtg gctggggcat ggaaggcaag attgtgtccc      1920 attccccag tgcggccagc tccgcgccag gatggcgagg aactcaataa agtgctttga     1980
aaatgctgag                                                            1990
```

<210> SEQ ID NO 26
<211> LENGTH: 3840
<212> TYPE: DNA
<213> ORGANISM: Homo sapiens
<220> FEATURE:
<221> NAME/KEY: proto-oncogene tyrosine-protein kinase c-abl
<222> LOCATION: (1)..(3840)
<223> OTHER INFORMATION: GenBank accession No. M14752

<400> SEQUENCE: 26

```
ggccttcccc ctgcgaggat cgccgttggc ccgggttggc tttggaaagc ggcggtggct        60
ttgggccggg ctcggcctcg ggaacgccag ggcccctgg gtgcggacgg gcgcggccag        120 gaggggggtta aggcgcaggc ggcggcgggg cggggggggg cctggcgggc gccctctccg      180 ggcccttttgt taacaggcgc gtcccggcca gcggagacgc ggccgccctg ggcgggcgcg      240
```

-continued

```
ggcggcgggc ggcggtgagg gcggcctgcg gggcggcgcc cggggggcgg gccgagccgg    300
gcctgagccg ggcccggacc gagctgggag aggggctccg gcccgatcgt tcgcttggcg    360
caaaatgttg gagatctgcc tgaagctggt gggctgcaaa tccaagaagg ggctgtcctc    420
gtcctccagc tgttatctgg aagaagccct tcagcggcca gtagcatctg actttgagcc    480
tcagggtctg agtgaagccg ctcgttggaa ctccaaggaa aaccttctcg ctggacccag    540
tgaaaatgac cccaacctt t cgttgcact gtatgatttt gtggccagtg agataacac    600 tctaagcata actaaaggtg aaaagctccg ggtcttaggc tataatcaca atggggaatg    660
gtgtgaagcc caaaccaaaa atggccaagg ctgggtccca agcaactaca tcacgccagt    720
caacagtctg gagaaacact cctggtacca tgggcctgtg tcccgcaatg ccgctgagta    780
tccgctgagc agcgggatca atggcagctt cttggtgcgt gagagtgaga gcagtcctag    840
ccagaggtcc atctcgctga gatacgaagg gagggtgtac cattacagga tcaacactgc    900
ttctgatggc aagctctacg tctcctccga gagccgcttc aacaccctgg ccgagttggt    960
tcatcatcat tcaacggtgg ccgacgggct catcaccacg ctccattatc cagccccaaa    1020
gcgcaacaag cccactgtct atggtgtgtc ccccaactac gacaagtggg agatggaacg    1080
cacggacatc accatgaagc acaagctggg cgggggccag tacggggagg tgtacgaggg    1140
cgtgtggaag aaatacagcc tgacggtggc cgtgaagacc ttgaaggagg acaccatgga    1200
ggtggaagag ttcttgaaag aagctgcagt catgaaagag atcaaacacc ctaacctagt    1260
gcagctcctt ggggtctgca cccggggagcc cccgttctat atcatcactg agttcatgac    1320
ctacgggaac ctcctggact acctgaggga gtgcaaccgg caggaggtga acgccgtggt    1380
gctgctgtac atggccactc agatctcgtc agccatggag tacctagaga agaaaaactt    1440
catccacaga gatcttgctg cccgaaactg cctggtaggg gagaaccact tggtgaaggt    1500
agctgatttt ggcctgagca ggttgatgac aggggacacc tacacagccc atgctggagc    1560
caagttcccc atcaaatgga ctgcacccga gagcctggcc tacaacaagt tctccatcaa    1620
gtccgacgtc tgggcatttg gagtattgct ttgggaaatt gctacctatg gcatgtcccc    1680
ttacccggga attgaccgtt cccaggtgta tgagctgcta gagaaggact accgcatgaa    1740
gcgcccagaa ggctgcccag agaaggtcta tgaactcatg cgagcatgtt ggcagtggaa    1800
tccctctgac cggccctcct ttgctgaaat ccaccaagcc tttgaaacaa tgttccagga    1860
atccagtatc tcagacgaag tggaaaagga gctggggaaa caaggcgtcc gtggggctgt    1920
gactaccttg ctgcaggccc cagagctgcc caccaagacg aggacctcca ggagagctgc    1980
agagcacaga gacaccactg acgtgcctga gatgcctcac tccaagggcc agggagagag    2040
cgatcctctg gaccatgagc ctgccgtgtc tccattgctc cctcgaaaag agcgaggtcc    2100
cccggagggc ggcctgaatg aagatgagcg ccttctcccc aaagacaaaa agaccaactt    2160
gttcagcgcc ttgatcaaga aagaagaaga gacagcccca ccccctccca acgcagcag    2220 ctccttccgg gagatggacg gccagccgga gcgcagaggg gccggcgagg aagagggccg    2280
agacatcagc aacggggcac tggctttcac ccccttggac acagctgacc cagccaagtc    2340
cccaaagccc agcaatgggg gctgggtccc caatggagcc ctcgggagt ccgggggctc    2400 aggcttccgg tctccccacc tgtggaagaa gtccagcacg ctgaccagca gccgcctagc    2460
caccggcgag gaggagggcg gtgggcagctc cagcaagcgc ttcctgcgct cttgctccgt    2520
ctcctgcgtt cccatggggg ccaaggacac ggagtggagg tcagtcacgc tgcctcggga    2580
```

-continued

```
cttgcagtcc acggaagac agtttgactc gtccacattt ggagggcaca aaagtgagaa      2640
gccggctctg cctcggaaga gggcagggga gaacaggtct gaccaggtga cccgaggcac      2700
agtaacgcct ccccccaggc tggtgaaaaa gaatgaggaa gctgctgatg aggtcttcaa      2760
agacatcatg gagtccagcc cgggctccag cccgcccaac ctgactccaa aacccctccg      2820
gcggcaggtc accgtggccc ctgcctcggg cctcccccac aaggaagaag cctggaaagg      2880
cagtgcctta gggacccctg ctgcagctga gccagtgacc cccaccagca aagcaggctc      2940
aggtgcacca aggggcacca gcaagggccc cgccgaggag tccagagtga ggaggcacaa      3000
gcactcctct gagtcgccag ggaggacaa ggggaaattg tccaagctca aacctgcccc      3060
gccgccccca ccagcagcct ctgcagggaa ggctggagga agccctcgc agaggcccgg      3120 ccaggaggct gccggggagg cagtcttggg cgcaaagaca aaagccacga gtctggttga      3180
tgctgtgaac agtgacgctg ccaagcccag ccagccggca gagggcctca aaaagcccgt      3240
gctcccggcc actccaaagc cacccccgc caagccgtcg ggacccccca tcagcccagc      3300
ccccgttccc ctttccacgt tgccatcagc atcctcggcc ttggcagggg accagccgtc      3360
ttccactgcc ttcatccctc tcatatcaac ccgagtgtct cttcggaaaa cccgccagcc      3420
tccagagcgg gccagcggcg ccatcaccaa gggcgtggtc ttggacagca ccgaggcgct      3480
gtgcctcgcc atctctggga actccgagca gatggccagc cacagcgcag tgctggaggc      3540
cggcaaaaac ctctacacgt tctgcgtgag ctatgtggat tccatccagc aaatgaggaa      3600
caagtttgcc ttccgagagg ccatcaacaa actggagaat aatctccggg agcttcagat      3660
ctgcccggcg tcagcaggca gtggtccggc ggccactcag gacttcagca agctcctcag      3720
ttcggtgaag gaaatcagtg acatagtgca gaggtagcag cagtcagggg tcaggtgtca      3780
ggcccgtcgg agctgcctgc agcacatgcg ggctcgccca tacccatgac agtggctgag      3840
```

<210> SEQ ID NO 27
<211> LENGTH: 1628
<212> TYPE: DNA
<213> ORGANISM: Homo sapiens
<220> FEATURE:
<221> NAME/KEY: AF1q
<222> LOCATION: (1)..(1628)
<223> OTHER INFORMATION: GenBank accession No. U16954
<220> FEATURE:
<221> NAME/KEY: misc_feature
<222> LOCATION: (114)..(114)
<223> OTHER INFORMATION: undefined  nucleotide

<400> SEQUENCE: 27

```
agtcagcacg ggggtgctgg aagagatcgg gaataatagc gcagaccaat gagcctaggg       60
agatgctttc atcgtctctc cttccctcaa gtgttctgga acctatcatt tganttagcc      120
gagtcaggca ggaggggggcg gggaatcctt ccgcccttct taggaggggc tgcattgcag      180
ggggagagtg aactgacaga ctcagtcact gaagagggaa aaggagtgag aagacaaagc      240
cgtcaaagcc ccaacagctt tgtatttctc cagcccggcc ggcagacccc ggagctcccg      300
aggcactccc tccatctttg gaacgcgcca gtaattgaat tgataacagg aagctatgag      360
ggaccctgtg agtagccagt acagttcctt tcttttctgg aggatgccca tcccagaact      420
ggatctgtcg gagctggaag gcctgggtct gtcagataca gccacctaca aggtcaaaga      480
cagcagcgtt ggcaaaatga tcgggcaagc aactgcagca gaccaggaga aaaaccctga      540
aggtgatggc ctccttgagt acagcacctt caacttctgg agagctccca ttgccagcat      600
ccactccttc gaactggact tgctctaagg ccaagacttc tctctcccat caccttgccc      660
```

-continued

| | | |
|---|---|---|
| tcattgtctt ccctctcaag cccttcctt tccactcctt tcccatttta atcttgttct | 720 |
| ctccctactg tgttggtggt gctgatgaat ctgccagagt tgagttctat gtatttattt | 780 |
| atctatctgt ctactccatt tctctcaaaa gccctcaagt cacaaagtaa atggttcaag | 840 |
| caatggagta ctgggtcaca gggattcctc ctttcccccc caaatattaa ctccagaaac | 900 |
| taggcctgac tggggacacc ctgagagtag tatagtagtg caaaatggaa gactgatttt | 960 |
| tgactctatt ataatcagct tcagagattc cttaaaccct cctaatttcc tgctccaggg | 1020 |
| cagtgaaaca caaatatttc ttcaaggggt gatgaaaacc tcggaagttt taatttgagg | 1080 |
| ttatctgcta cgaaacagta tttctaaaag gctaaagtga taagtctctt gcttttttt | 1140 |
| gatcctgctc ttatattctt ttttttcctc agagaaatca ggagggtagt tagaggtata | 1200 |
| aaacaggagg aaatattatg gaaatgaaa atagggaaaa taattgaatc attttagaag | 1260 |
| tagctaattt cttttctcaa aagagtgtcc cttcttcaca cctactcact ttacaacttt | 1320 |
| gctcctaact gtgggttgaa aactctagct aaagaaagtt atcaaatctt aacatgcatt | 1380 |
| cctactatta tgatagtttt taaggtttca attcaatctt ctgaacggca taagtccctat | 1440 |
| tttagcctta cctcctgcat ttgcaatacg taatactgat cagtgggcac agttcttcag | 1500 |
| ctacattgag accctgaaat gaacaattat attctgactc gacatcttgt ccccaatcct | 1560 |
| tccaaaaata ttgatggtga tttgtgctac catttactcg tttatttaat aaagacattc | 1620 |
| aattccca | 1628 |

<210> SEQ ID NO 28
<211> LENGTH: 993
<212> TYPE: DNA
<213> ORGANISM: Homo sapiens
<220> FEATURE:
<221> NAME/KEY: guanidinoacetate N-methyltransferase
<222> LOCATION: (1)..(993)
<223> OTHER INFORMATION: GenBank accession No. Z49878

<400> SEQUENCE: 28

| | | |
|---|---|---|
| cggcggcgcg cgatcgaggt cgggtcgccg tccagcctgc agcatgagcg cccccagcgc | 60 |
| gaccccatc ttcgcgcccg gcgagaactg cagccccgcg tgggggggcgg cgcccgcggc | 120 |
| ctacgacgca gcggacacgc acctgcgcat cctgggcaag ccggtgatgg agcgctggga | 180 |
| gaccccctat atgcacgcgc tggccgccgc cgcctcctcc aaaggggggcc gggtcctgga | 240 |
| ggtgggcttg gcatggcca tcgcagcgtc aaaggtgcag gaggcgccca ttgatgagca | 300 |
| ttggatcatc gagtgcaatg acggcgtctt ccagcggctc cgggactggg ccccacggca | 360 |
| gacacacaag gtcatcccct tgaaaggcct gtgggaggat gtggcaccca ccctgcctga | 420 |
| cggtcacttt gatgggatcc tgtacgacac gtacccactc tcggaggaga cctggcacac | 480 |
| acaccagttc aacttcatca gaaccacgc ctttcgcctg ctgaagccgg ggggcgtcct | 540 |
| cacctactgc aacctcacct cctggggggga gctgatgaag tccaagtact cagacatcac | 600 |
| catcatgttt gaggagacgc aggtgccgc gctgctggag gccggcttcc ggagggagaa | 660 |
| catccgtacg gaggtgatgg cgctggtccc accggccgac tgccgctact acgccttccc | 720 |
| acagatgatc acgcccctgg tgaccaaagg ctgagccccc accccggccc ggccacaccc | 780 |
| atgccctccg ccgtgccttc ctggccggga gtccagggtg tcgcaccagc cctgggctga | 840 |
| tcccagctgt gtgtcaccag aagctttccc ggcttctctg tgaggggtcc caccagccca | 900 |
| gggctgatcc cagctgtgtg tcaccagcag ctttcccagc ttgctctgtg agggtcactg | 960 |

```
ctgcccactg cagggtgccc tgaggtgaag ccg                                  993
```

<210> SEQ ID NO 29
<211> LENGTH: 835
<212> TYPE: DNA
<213> ORGANISM: Homo sapiens
<220> FEATURE:
<221> NAME/KEY: interferon-induced nuclear phosphoprotein
<222> LOCATION: (1)..(835)
<223> OTHER INFORMATION: Genbank accession No. as of 09 Dec 2002: L22342

<400> SEQUENCE: 29

```
atggcgagca gcggagtcaa gaacacacca cgatggcgga gaaaagcccc tcatgggagg        60
gaaaggaaag agaaaggaaa gaaaagaaaa agatgtatct ggtcaactcc aaaaaggaga      120
cataagaaaa aaagcctccc aagagagatc attgatggca cttcagaaat gaatgaagga      180
aagaggtccc agaagatgcc tagtacacca cgaagggtca cacaaggggc agcctcacct      240
gggcatggca tccaagagaa gctccaagtg gtggataagg tgactcaaag gaaagacgac      300
tcaacctgga actcagaggt catgatgagg gtccaaaagg caagaactaa atgtgcccga      360
aagtccagat cgaaagaaaa gaaaaaggag aaagatatct gttcaagctc aaaaaggaga      420
tttcagaaaa atattcaccg aagaggaaaa cccaaaagtg acactgtgga ttttcactgt      480
tctaagtccc ccgtgacctg tggtgaggcg aaagggattt tatataagaa gaaaatgaaa      540
cacggatcct cagtgaagtg cattcggaat gaggatggaa cttggttaac accaaatgaa      600
tttgaagtcg aaggaaaagg aaggaacgca aagaactgga aacggaatat acgttgtgaa      660
ggaatgaccc taggagagct gctgaagagt ggactttttgc tctgtcctcc aagaataaat      720
ctcaagagag agttaaatag caagtgaatt tctactaccc tctcagtcac catgttgcag      780
actttccctg tctggaggct caccttagag cttctgagtt tccaagcccg gaatt           835
```